US011730135B2

(12) United States Patent
Ashkenazi et al.

(10) Patent No.: US 11,730,135 B2
(45) Date of Patent: *Aug. 22, 2023

(54) **RESISTANCE IN PLANTS OF *SOLANUM LYCOPERSICUM* TO THE TOBAMOVIRUS TOMATO BROWN RUGOSE FRUIT VIRUS**

(71) Applicant: VILMORIN & CIE, Paris (FR)

(72) Inventors: Varda Ashkenazi, Berurim (IL); Yaniv Rotem, Berurim (IL); Ron Ecker, Berurim (IL); Shai Nashilevitz, Berurim (IL); Naama Barom, Berurim (IL)

(73) Assignee: VILMORIN & CIE., Paris (FR)

( * ) Notice: Subject to any disclaimer, the term of this patent is extended or adjusted under 35 U.S.C. 154(b) by 169 days.

This patent is subject to a terminal disclaimer.

(21) Appl. No.: 16/694,089

(22) Filed: Nov. 25, 2019

(65) Prior Publication Data
US 2020/0077614 A1    Mar. 12, 2020

Related U.S. Application Data

(63) Continuation of application No. PCT/IB2019/000674, filed on Jun. 14, 2019, and a continuation-in-part of application No. PCT/EP2018/064055, filed on May 29, 2018.

(30) Foreign Application Priority Data

Jun. 1, 2017 (EP) .................................... 17305644

(51) Int. Cl.
| A01H 5/10 | (2018.01) |
| A01H 6/82 | (2018.01) |
| C12Q 1/6895 | (2018.01) |
| C12Q 1/6827 | (2018.01) |

(52) U.S. Cl.
CPC .............. *A01H 6/825* (2018.05); *A01H 5/10* (2013.01); *C12Q 1/6827* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

2016/0242376 A1    8/2016    Jiang

FOREIGN PATENT DOCUMENTS

| WO | WO 2013/064641 A1 | 5/2013 |
| WO | WO 2017/012951 A1 | 1/2017 |
| WO | WO 2018/219941 A1 | 12/2018 |
| WO | WO 2019/110130 A1 | 6/2019 |
| WO | WO 2019/110821 A1 | 6/2019 |

OTHER PUBLICATIONS

Johnson et al, Genes Genomes Genetics 2: 1145-1159, 2012 (Year: 2012).*
Bombarely A. et al, "The sol genomics network (solgenomics.net) : growing tomatoes using Perl", Nucleic Acids Research, 2011, vol. 39, D1149-D1155.
Ishibashi K et al, "An inhibitor of viral RNA replication is encoded by a plant resistance gene", PNAS, vol. 104, No. 34, Aug. 21, 2007, pp. 13833-13838.
Kadirvel P. et al, "Mapping of QTLs in tomato line FLA456 associated with resistance to a virus causing tomato yellow leaf curl disease", EUPHYTICA, vol. 190, No. 2, Dec. 5, 2012, 297-308.
Li J. et al., "Seedling salt tolerance in tomato", Euphytica (2011) 178: 403-414.
Luria et al., "A New Israeli Tobamovirus Isolate Infects Tomato Plants Harboring Tm-$2^2$ Resistance Genes", PLoS One, 2017; 12(1) : e0170429, pp. 1-19.
Pelham et al., "The establishment of a new strain of tobacco mosaic virus resulting from the use of resistance varieties of tomatos", Ann. Appl. Biol., 65: 293-297, 1970.
Salem N. et al., "A new tobamovirus infecting tomato crops in Jordan", Archives of virology, Springer Wien, AT, vol. 161, No. 2, Nov. 19, 2015, 503-506.
Seifi A. et al., "Genetics and molecular mechanisms of resistance to powdery mildews in tomato (*Solanum lycopersicum*) and its wild relatives", Eur J Plant Pathol (2014) 138: 641-665.
Shi A. et al., "Molecular markers for Tm-2 Alleles of tomato mosaic virus resistance in tomato", American Journal of plant sciences, vol. 02, No. 02, Jan. 1, 2011, 180-189.
Szczechura W. et al., "Tomato molecular markers", Vegetable crops research bulletin, vol. 74, Jun. 13, 2011, 5-23.
"Ctsb1h14 Tomato Seed Library [B] Solanum lycopersicum cDNA clone cTSB-1-H14 5' , mRNA sequence", XP002797385, EBI accession No. G0372341, Apr. 1, 2009.
Watanabe Y. et al., "Characterization of Tm-1 gene action on replication of common isolates and a resistance-breaking isolate of TMV", Virology, Elsevier, Amsterdam, NL, vol. 161, No. 2, Dec. 1, 1987, pp. 527-532.

(Continued)

*Primary Examiner* — Mykola V. Kovalenko
(74) *Attorney, Agent, or Firm* — John P. White

(57) ABSTRACT

The invention relates to a *Solanum lycopersicum* plant resistant to Tomato Brown Rugose Fruit virus comprising in its genome the combination of the Tm-1 resistance gene on chromosome 2, and at least one quantitative trait locus (QTL) chosen from QTL3 on chromosome 11, QTL1 on chromosome 6 and QTL2 on chromosome 9, that independently confer to the plant foliar and/or fruit tolerance to TBRFV, wherein said QTLs are present in the genome of a plant of the seeds HAZTBRFVRES1 NCIMB accession number 42758. The combination of at least one of these QTLs with the Tm-1 gene delays, reduces or inhibits the replication or multiplication of the virus in the plants of the invention. The invention is also directed to parts of these plants with TBRFV resistance phenotype, as well as progeny, to the use of these plants for introgressing the resistance in another genetic background, as well as to different methods for obtaining tomato plants or seeds with increased resistance to Tomato Brown Rugose Fruit virus.

20 Claims, 4 Drawing Sheets

Figure 1:
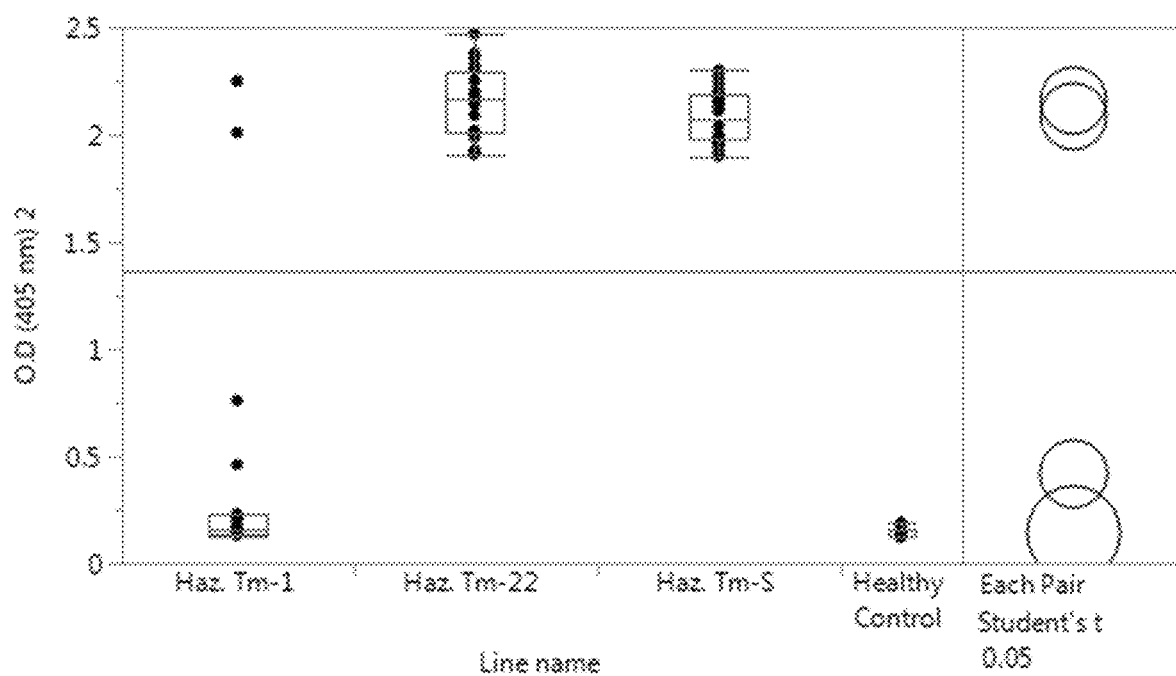

Specification includes a Sequence Listing.

(56) References Cited

OTHER PUBLICATIONS

International Search Report dated Feb. 21, 2020 in connection with PCT International Application No. PCT/IB2019/000674.
Written Opinion (form PCT/ISA/237) dated Feb. 21, 2020 in connection with PCT International Application No. PCT/IB2019/000674.

* cited by examiner

RESISTANCE IN PLANTS OF *SOLANUM LYCOPERSICUM* TO THE TOBAMOVIRUS TOMATO BROWN RUGOSE FRUIT VIRUS

CROSS-REFERENCE TO RELATED APPLICATIONS

This application is a continuation of PCT International Application No. PCT/IB2019/000674, filed Jun. 14, 2019, and a continuation-in-part of PCT International Application No. PCT/EP2018/064055, filed May 29, 2018, claiming priority of European Patent Application No. 17305644.1, filed Jun. 1, 2017, the contents of each of which are hereby incorporated by reference into the application.

REFERENCE TO A SEQUENCE LISTING

This application incorporates-by-reference nucleotide and/or amino acid sequences which are present in the file named "191125_91213_Sequence_Listing_CAS.txt", which is 33.6 bytes in size, and which was created Nov. 25, 2019 in the IBM-PC machine format, having an operating system compatibility with MS-Windows, which is contained in the text file which is being submitted as part of this application.

The present invention relates to resistance in plants of *Solanum lycopersicum*, also known as *Lycopersicum esculentum*, to the tobamovirus Tomato Brown Rugose Fruit virus (TBRFV, also known as ToBRFV). More specifically, the present invention relates to tomato plants and fruits comprising one or more genetic determinants, in combination with the Tm-1 resistance gene, that lead to resistance to the Tomato Brown Rugose Fruit virus. The invention further relates to markers linked to these one or more genetic determinant(s) and Tm-1 gene and to the use of such markers to identify or select plants carrying such resistance. The invention also relates to the seeds and progeny of such plants and to propagation material for obtaining such plants, and to different uses of these plants.

BACKGROUND OF THE INVENTION

All cultivated and commercial forms of tomato belong to a species most frequently referred to as *Lycopersicon esculentum* Miller. *Lycopersicon* is a relatively small genus within the extremely large and diverse family Solanaceae which is considered to consist of around 90 genera, including pepper, tobacco and eggplant. The genus *Lycopersicon* has been divided into two subgenera, the *esculentum* complex which contains those species that can easily be crossed with the commercial tomato and the *peruvianum* complex which contains those species which are crossed with considerable difficulty (Stevens, M., and Rick, C. M. 1986). Due to its value as a crop, *L. esculentum* Miller has become widely disseminated all over the world. Even if the precise origin of the cultivated tomato is still somewhat unclear, it seems to come from the Americas, being native to Ecuador, Peru and the Galapagos Island and initially cultivated by Aztecs and Incas as early as 700 AD. Mexico appears to have been the site of domestication and the source of the earliest introduction. It is supposed that the cherry tomato, *L. esculentum* var. *cerasiforme*, is the direct ancestor of modern cultivated forms.

Tomato is grown for its fruit, widely used as a fresh market or processed product. As a crop, tomato is grown commercially wherever environmental conditions permit the production of an economically viable yield. The majority of fresh market tomatoes are harvested by hand at vine ripe and mature green stage of ripeness. Fresh market tomatoes are available year round. Processing tomato are mostly mechanically harvested and used in many forms, as canned tomatoes, tomato juice, tomato sauce, puree, paste or even catsup.

Tomato is a normally simple diploid species with twelve pairs of differentiated chromosomes. However, polyploidy tomato is also part of the present invention. The cultivated tomato is self-fertile and almost exclusively self-pollinating. The tomato flowers are hermaphrodites. Commercial cultivars were initially open pollinated. As hybrid vigor has been identified in tomatoes, hybrids are replacing the open pollinated varieties by gaining more and more popularity amongst farmers with better yield and uniformity of plant characteristics. Due to its wide dissemination and high value, tomato has been intensively bred. This explains why such a wide array of tomato is now available. The shape may range from small to large, and there are cherry, plum, pear, blocky, round, and beefsteak types. Tomatoes may be grouped by the amount of time it takes for the plants to mature fruit for harvest and, in general the cultivars are considered to be early, midseason or late-maturing. Tomatoes can also be grouped by the plant's growth habit; determinate, semi-determinate or indeterminate. Determinate plants tend to grow their foliage first, then set flowers that mature into fruit if pollination is successful. All of the fruits tend to ripen on a plant at about the same time. Indeterminate tomatoes start out by growing some foliage, then continue to produce foliage and flowers throughout the growing season. These plants will tend to have tomato fruit in different stages of maturity at any given time. The semi-determinate tomatoes have a phenotype between determinate and indeterminate, they are typical determinate types except that grow larger than determinate varieties. More recent developments in tomato breeding have led to a wider array of fruit color. In addition to the standard red ripe color, tomatoes can be creamy white, lime green, pink, yellow, golden, orange or purple. Hybrid commercial tomato seed can be produced by hand pollination. Pollen of the male parent is harvested and manually applied to the stigmatic surface of the female inbred. Prior to and after hand pollination, flowers are covered so that insects do not bring foreign pollen and create a mix or impurity. Flowers are tagged to identify pollinated fruit from which seed will be harvested.

A variety of pathogens affect the productivity of tomato plants, including virus, fungi, bacteria, nematodes and insects. Tomatoes are inter alia susceptible to many viruses and virus resistance is therefore of major agricultural importance.

Tobamoviruses are among the most important plant viruses causing severe damages in agriculture, especially to vegetable and ornamental crops around the world. Tobamoviruses are easily transmitted by mechanical means while there is no evidence of a natural vector, as well as through seed transmission. Tobamoviruses are generally characterized by a rod-shaped particle of about 300 nm, their structure consists in a single stranded, positive RNA genome encoding four proteins, encapsidated by 17 KDa coat protein (CP) molecules.

In tomatoes, tobacco mosaic virus (TMV), tomato mosaic virus (ToMV) are feared by growers worldwide as they can severely damage crop production, for example through irregular ripening (fruits having yellowish patches on the surface and brownish spots beneath the surface). Several genes have however been identified by plants breeders over the years.

The first resistance gene identified was the Tm-1 gene, conferring resistance to TMV. This gene, introgressed from *S. habrochaites*, is incompletely dominant and homozygosis was generally required for the TMV resistance. The Tm-1 gene was however overcome within about one year of introduction to commercial horticulture, rendering the pursuing of its introduction into other commercial lines entirely useless (Pelham et al, 1970. "The establishment of a new strain of tobacco mosaic virus resulting from the use of resistant varieties of tomato"; Ann. Appl. Biol., 65:293-297). This gene was also identified as conferring resistance to ToMV, but today, the vast majority of the circulating TMV and ToMV strains are able to infect commercial plants harboring the Tm-1 gene, such that this gene is no longer considered as a resistance gene against TMV/ToMV infection in commercial plants. The use of this Tm-1 gene has now been almost completely abandoned in favor of alternative resistance genes.

For the last decades, all modern indeterminate tomato varieties and many of the determinate tomato varieties indeed contain the Tm-2 gene or preferably the Tm-$2^2$ allele of this gene, which give them immunity to almost all known races of Tobamoviruses which affected commercial tomatoes (ToMV and TMV) before 2014.

During 2014-2015, a severe outbreak of virus affected tomato productions areas in the middle east, such as in Jordan and in Israel. Most of the tomato varieties affected were considered TMV and/or ToMV resistant, but were still severely affected and showed typical TMV/ToMV like symptoms: while the foliar ones were quite similar to the TMV/ToMV symptoms, the fruit symptoms were much more frequent and severe than the usual symptoms from such viruses with fruits lesions and deformations. The fruit quality was very poor and rather unmarketable. Salem et al (Arch.Virol. 161 (2), 503-506. 2015) extracted RNA from fruit and leaves of symptomatic plants, infected in Jordan, and made various tests leading to the identification of a new Tobamovirus species, the sequence of which corresponds to GenBank accession no. KT383474 (SEQ ID No:25); Salem et al proposed to name this Jordanian virus: Tomato Brown Rugose Fruit virus (TBRFV or ToBRFV). The comparison to other Tobamoviruses sequences showed that it is indeed a Tobamovirus, but not TMV or ToMV. The resistance to TMV and/or ToMV does not confer resistance to this new virus TBRFV.

Luria et al (PLoS One. 2017; 12(1): e0170429) have concomitantly isolated and sequenced the complete genome of the Israeli tobamovirus infecting tomato in Israel, corresponding to GenBank accession no. KX619418 (SEQ ID No:26). They have thus shown a very high sequence identity between the Israeli and the Jordanian viruses (more than 99% sequence identity) and have concluded to two different isolates of tomato brown rugose fruit virus.

Recently, the virus was identified in Europe, especially in Sicily, Germany and the Netherlands, and in Mexico, and therefore now it is considered as a major global threat to tomato crop. The strain identified appears to be the Israeli strain, rather than the Jordanian strain.

In Israel, the present inventors collected isolates, and 7 representative isolates from all crop production areas (North, Center and South) were sequenced. Sequence comparison to the sequence of the Jordanian ToBRFV seems to indicate that all the Israeli isolates are essentially but not entirely identical to the Jordanian isolate, thus confirming they are probably to be considered as two different strains of the same virus in both countries.

In a previous application, the present inventors have first identified tomato plants which display tolerance to the Tomato Brown Rugose Fruit virus and they have been able to localize and identify genetic determinants, also referred to hereafter as QTLs (Quantitative Trait Locus) that lead to tolerance to the Tomato Brown Rugose Fruit virus. Two QTLs, namely QTL1 and QTL2, are to be found on chromosome 6 and 9 respectively, and confer independently or in combination an improved tolerance in the fruits of a tomato plant infected or likely to be infected by the TBRFV, when present homozygously into a *S. lycopersicum* background. A third QTL, QTL3, is to be found on chromosome 11, and confers an improved tolerance in the leaves of a tomato plant infected or likely to be infected by the TBRFV, when present homozygously. These QTLs are those referred to and described in PCT application WO2018/219941. These QTLs will be called tolerance QTLs in the following description.

Whereas these QTLs, either alone or in combination, provide tolerance to TBRFV, the inventors have now established that, most of the time, they cannot confer resistance to the tomato plants, especially they cannot confer a level of resistance sufficient to delay, reduce or inhibit the replication or multiplication of the virus. Indeed, infected plants bearing one or more of said tolerance QTLs are nevertheless propagating the virus, which remains a threat for all surrounding tomato plants not bearing these QTLs.

As Tobamoviruses are not easily controlled but through genetic improvement by the identification and use in breeding of resistance genes, and as the resistance genes currently available to control TMV and/or ToMV are useless against the damages and propagation from the new Tomato Brown Rugose Fruit virus, and the tolerance QTLs not able to stop or sufficiently reduce the viral propagation, there is an urgent need to identify resistance against this new Tobamovirus, failing that would result in entire regions in which tomato crop could not be produced anymore.

SUMMARY

The present inventors have identified tomato plants which display resistance to the Tomato Brown Rugose Fruit virus and they have been able to identify the combination of genetic determinants that leads to the resistance to the Tomato Brown Rugose Fruit virus, namely the combination of QTLs (Quantitative Trait Locus) and gene providing this resistance or enhanced tolerance.

The resistance according to the present invention is imparted by the Tm-1 resistance gene, when combined with genetic determinants or QTLs, wherein these QTLs confer only tolerance to the Tomato Brown Rugose Fruit virus (TBRFV) at the level of the leaves and/or the fruits of the tomato plants, when they are not combined with the Tm-1 resistance gene. These QTLs or genetic determinants are described as being of recessive nature, according to WO2018/219941. The presence of the Tm-1 resistance gene at the homozygous state is not necessary, contrary to the main mode of action of the Tm-1 gene with regard to past resistance to TMV/ToMV, although this resistance has now been overcome by the circulating strains of TMV/ToMV.

The fruit tolerance is imparted independently by QTL1 or QTL2, and the foliar tolerance by QTL3, their transfer to different genetic background, i.e. into various tomatoes can be easily carried out by a skilled artisan in plant breeding, especially given the information regarding suitable markers associated with the QTLs provided in WO2018/219941. The same is also true for the Tm-1 gene.

The present invention thus provides the combination of:
genetic determinants, also named here QTLs or tolerance QTLs, conferring, when present in the homozygous state, the phenotype of TBRFV tolerance at the level of the tomato leaves and/or fruits of the tomato plants infected by the TBRFV, and
the Tm-1 gene,
wherein this combination provides resistance to the TBRFV, in particular the ability to delay, reduce and/or inhibit the replication of the virus, whereas neither the QTLs alone or in combination, nor the Tm-1 gene alone, provides such a level of resistance or of enhanced tolerance.

The present invention also concerns commercial *S. lycopersicum* plants that display resistance to TBRFV as well as methods that produce or identify *S. lycopersicum* plants or populations (germplasm) that display resistance to TBRFV. The present invention also discloses molecular genetic markers, especially SNPs, linked to the tolerance QTLs and to the Tm-1 gene, which can be used in any selection method for obtaining the plant of the invention. Plants obtained through the methods and uses of such molecular markers are also provided.

The invention also provides several methods for improving the yield of tomato production in an environment infested by TBRFV and methods for protecting a tomato field from TBRFV infestation.

Definitions

The term "Resistance" is as defined by the ISF (International Seed Federation) Vegetable and Ornamental Crops Section for describing the reaction of plants to pests or pathogens, and abiotic stresses for the Vegetable Seed Industry. Specifically, by resistance, it is meant the ability of a plant variety to restrict the growth and development of a specified pest or pathogen and/or the damage they cause when compared to susceptible plant varieties under similar environmental conditions and pest or pathogen pressure. Resistant varieties may exhibit some disease symptoms or damage under heavy pest or pathogen pressure.

The term 'Tolerance' is used herein to indicate a phenotype of a plant wherein at least some of the disease-symptoms remain absent upon exposure of said plant to an infective dose of virus, whereby the presence of a systemic or local infection, virus multiplication, at least the presence of viral genomic sequences in cells of said plant and/or genomic integration thereof can be established, at least under some culture conditions. Tolerant plants are therefore resistant for symptom expression but symptomless carriers of the virus. Sometimes, viral sequences may be present or even multiply in plants without causing disease symptoms. It is to be understood that a tolerant plant, although it is infected by the virus, is generally able to restrict at least moderately the growth and development of the virus.

In case of TBRFV, by leave tolerance, or foliar tolerance, it is meant the phenotype of a plant wherein the disease symptoms on the leaves remain absent upon exposure of said plant to an infective dose of TBRFV. Disease symptoms on the fruits may however be present on infected plants.

By fruit tolerance, in case of TBRFV, it is meant the phenotype of a plant wherein the disease symptoms on the fruits remain absent upon exposure of said plant to an infective dose of TBRFV. Disease symptoms on the leaves may however be present on infected plants.

Symptoms on leaves of TBRFV infection generally include mosaic, distortion of the leaflets and in many cases also shoestrings like symptoms. Symptoms on fruits of TBRFV infection generally include typical yellow lesions and deformation of the fruits. In many cases there are also "chocolate spots" on the fruits.

Susceptibility: The inability of a plant variety to restrict the growth and development of a specified pest or pathogen; a susceptible plant displays the detrimental symptoms linked to the virus infection, namely the foliar damages and fruit damages in case of TBRFV infection.

A *S. lycopersicum* plant susceptible to Tomato Brown Rugose Fruit virus, is for example the commercially available variety Candela as mentioned in the 2015 Salem et al. publication. It can also be the Hazera N° 2 and Hazera N° 4 lines mentioned in the PCT application WO2018/219941. All commercially available varieties of tomato grown in TBRFV infected area are, to date, i.e. before the present invention, susceptible to TBRFV, or at best tolerant for those plants bearing the tolerance QTLs, such as the deposited seeds of HAZTBRFVRES1. A sample of this *S. lycopersicum* seed has been deposited by Hazera Seeds Ltd. Berurim, M.P. Shimim 79837, Israel, pursuant to and in satisfaction of the requirements of the Budapest treaty on the International Recognition of the deposit of Microorganisms for the Purpose of Patent procedure ("the Budapest Treaty" with the National collection of Industrial, Food and Marine bacteria (NCIMB) (NCIMB, Ltd, Ferguson Building, Craibstone Estate, Bucksburn, Aberdeen AB21 9YA, united Kingdom) on 16 May 2017 under accession number 42758.

A plant according to the invention has thus at least improved resistance or increased tolerance to Tomato Brown Rugose Fruit virus, with respect to the variety Candela, and more generally with respect to any commercial variety of tomato grown in Tomato Brown Rugose Fruit virus infected area, including tolerant plant, and with respect to HAZTBRFVRES1.

As used herein, the term "offspring" or "progeny" refers to any plant resulting as progeny from a vegetative or sexual reproduction from one or more parent plants or descendants thereof. For instance an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "genetic determinant" and/or "QTL" refers to any segment of DNA associated with a biological function. Thus, QTLs and/or genetic determinants include, but are not limited to, genes, coding sequences and/or the regulatory sequences required for their expression.

QTLs and/or genetic determinants can also include non-expressed DNA segments that, for example, form recognition sequences for other proteins.

As used herein, the term "genotype" refers to the genetic makeup of an individual cell, cell culture, tissue, organism (e.g., a plant), or group of organisms.

As used herein, the term "grafting" is the operation by which a rootstock is grafted with a scion. The primary motive for grafting is to avoid damages by soil-born pest and pathogens when genetic or chemical approaches for disease management are not available. Grafting a susceptible scion onto a resistant rootstock can provide a resistant cultivar without the need to breed the resistance into the cultivar. In addition, grafting may enhance tolerance to abiotic stress, increase yield and result in more efficient water and nutrient uses.

As used herein, the term "heterozygote" refers to a diploid or polyploid individual cell or plant having different alleles (forms of a given gene, genetic determinant or sequences) present at least at one locus.

As used herein, the term "heterozygous" refers to the presence of different alleles (forms of a given gene, genetic determinant or sequences) at a particular locus.

As used herein, "homologous chromosomes", or "homologs" (or homologues), refer to a set of one maternal and one paternal chromosomes that pair up with each other during meiosis. These copies have the same genes in the same loci and the same centromere location.

As used herein, the term "homozygote" refers to an individual cell or plant having the same alleles at one or more loci on all homologous chromosomes.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "locus" (plural: "loci") refers to any site that has been defined genetically, this can be a single position (nucleotide) or a chromosomal region. A locus may be a gene, a genetic determinant, or part of a gene, or a DNA sequence, and may be occupied by different sequences. A locus may also be defined by a SNP (Single Nucleotide Polymorphism), by several SNPs, or by two flanking SNPs.

As used herein, the term "rootstock" is the lower part of a plant capable of receiving a scion in a grafting process.

As used herein, the term "scion" is the higher part of a plant capable of being grafted onto a rootstock in a grafting process.

DETAILED DESCRIPTION OF THE INVENTION

The present inventors have demonstrated that the three QTLs disclosed in WO2018/219941, which, when present homozygously in a *S. lycopersicum* plant, alone or in combination, provide an improved tolerance in the fruits and/or leaves of a tomato plant infected or likely to be infected by the Tomato Brown Rugose Fruit virus (TBRFV or ToBRFV in the following), are nevertheless not entirely able to restrict the propagation of the virus. Indeed, they have discovered that multiplication of the virus generally occurs within these plants, as evidenced by the detection of viral genomic sequences in cells of said plants. Such plants are thus bearing the virus and are unable to limit the propagation of the virus from plants to plants.

The three QTLs disclosed in WO2018/219941, namely QTL1, QTL2 and QTL3, on chromosomes 6, 9 and 11 respectively, will be referred to in the following as the "tolerance QTLs". More specifically, the QTL1 and QTL2 will be referred to as the "fruit tolerance QTLs" and QTL3 on chromosome 11 as the "foliar tolerance QTL".

The present inventors have unexpectedly found that the combination of at least one of said tolerance QTLs, namely QTL1, QTL2 and/or QTL3, with the Tm-1 resistance gene, confers an improved tolerance or resistance in tomato, against TBRFV, especially against the Israeli isolate strain, reduces the virus titer in the tomato plants and/or inhibits the propagation of the virus. According to a preferred embodiment, at least one of the tolerance QTL is present homozygously, e.g. QTL3, especially if there is only one QTL.

Moreover, it is also preferred that at least two tolerance QTLs are combined with the Tm-1 gene; in such a case, at least one QTL is advantageously present heterozygously, e.g. QTL2. According to an embodiment, there are 2 or 3 of the tolerance QTLs, in combination with the Tm-1 gene, and at least one QTL is present homozygously and at least another one heterozygously.

It is noted that the Tm-1 resistance gene, although previously identified as a resistance gene against TMV and ToMV is no longer providing resistance to circulating ToMV/TMV strains, as the circulating ToMV and TMV strains have mutated in order to escape this resistance. The presence of the Tm-1 resistance gene in the plants of the invention therefore does not provide ToMV and/or TMV resistance to these plants, especially for commercial plants threatened specifically by the circulating ToMV/TMV strains.

As demonstrated in the examples, the phenotype of the plants according to the invention is resistance to TBRFV, namely foliar and/or fruit resistance, and the plants of the invention are capable of improved restriction of the viral propagation.

By improved restriction of the viral propagation, it is meant that the level of viral sequences (for example as detected by q-RT-PCR) or protein detected in a plant, as measured by ELISA technique at around 70-90 days post inoculation (DPI), is at least 50% inferior to the level of viral sequences detected in a susceptible plant or in a tolerant but not resistant plant, at the same time by the same technique, preferably at least 60% inferior, at least 70% or at least 80% inferior.

According to a first aspect, the invention is thus directed to a *Solanum lycopersicum* plant, resistant to Tomato Brown Rugose Fruit virus (TBRFV), comprising in its genome the combination of:

the Tm-1 resistance gene, homozygously or heterozygously, and at least one tolerance quantitative trait locus (QTL), present either homozygously or heterozygously.

Preferably, there are at least two QTLs, preferably one present homozygously and another one present heterozygously.

The invention is also directed to a cell of such plants, as well as seeds comprising said QTLs in combination with a Tm-1 gene.

The tolerance QTL is to be chosen in the group consisting of QTL3 on chromosome 11, QTL1 on chromosome 6 and QTL2 on chromosome 9. Each one of these tolerance QTLs, independently, confers to the plant foliar and/or fruit tolerance to TBRFV, and confers resistance or enhanced tolerance to TBRFV when combined with the Tm-1 gene. Said tolerance QTLs are present in the genome of a plant of the seeds HAZTBRFVRES1 NCIMB accession number 42758.

The Tm-1 gene is as defined inter alia in the publication Ishibashi et al, 2007 (An inhibitor of viral RNA replication is encoded by a plant resistance gene. PNAS Aug. 21, 2007

104 (34) 13833-13838); preferably 'Tm-1 gene' refers to a genetic sequence encoding a protein having the Tm-1 activity reported in the article, namely the ability to inhibit the viral replication of a wild-type ToMV strain Tm-1 sensitive, for example the strain ToMV-L disclosed in this article. According to a preferred embodiment, the Tm-1 gene according to the invention is a gene encoding a protein having the 754 amino acid sequence reported in Ishibashi et al, corresponding to SEQ ID No:19 (NCBI BAF75724), or a protein having at least 75%, preferably at least 80%, more preferably at least 85%, 90%, or 95% sequence identity with SEQ ID No:19 and exhibiting the Tm-1 activity reported in Ishibashi et al, 2007, namely the ability to inhibit viral RNA replication of a wild-type Tm-1 sensitive ToMV strain. According to a preferred embodiment, this gene has a sequence corresponding to the mRNA sequence referred to in Ishibashi et al, 2007, namely sequence NCIB AB287296 (SEQ ID No:20), or a sequence having at least 50%, preferably at least 60%, at least 70%, more preferably at least 75%, 80%, 85%, 90%, or 95% sequence identity with SEQ ID No:20. Irrespective of the degree of sequence identity with SEQ ID No:20, a Tm-1 gene according to the invention preferably encodes a protein exhibiting the Tm-1 activity reported in Ishibashi et al, 2007, namely the ability to inhibit viral RNA replication of wild-type ToMV.

It is preferred that, in the genome of a plant, seed or cell of the invention, the Tm-1 gene be present on chromosome 2. The present invention however also encompasses plant, seed or cell, comprising the Tm-1 gene at a locus which does not correspond to the locus mentioned in Ishibashi et al, 2007.

The invention thus encompasses S. lycopersicum plants, cells or seeds, comprising in their genome various combinations of QTL1, QTL2 and QTL3, preferably at least one QTL being at the homozygous state and/or at least one being at the heterozygous state, in association with Tm-1 gene. Preferably, there are at least 2 QTLs, and at least one is at the homozygous state and at least one at the heterozygous state. The invention thus encompasses plants comprising the combination of QTL3 and Tm-1, the combination of QTL1 and Tm-1, the combination of QTL2 and Tm-1, the combination of QTL3, QTL1 and Tm-1, the combination of QTL3, QTL2 and Tm-1, the combination of QTL1, QTL2 and Tm-1 and the combination of QTL1, QTL2, QTL3 and Tm-1. Particularly preferred combinations are QTL3 and Tm-1, and QTL2, QTL3 and Tm-1. Different alternative combinations are disclosed in Table 1 below; it is particularly preferred that QTL3 be present at the homozygous state and QTL2 at the heterozygous state.

It is to be understood that, in the context of the present invention, preferably at least one of the tolerance QTL is to be found homozygously in the genome of the plants, whereas the Tm-1 resistance gene can be found heterozygously or homozygously.

According to an embodiment, the QTL2 on chromosome 9 is present heterozygously in a plant according to the invention.

In another preferred embodiment, the plant comprises homozygously QTL3, in combination with Tm-1, either homozygously or heterozygously. Such a plant may advantageously also comprise QTL2, preferably heterozygously.

According to a preferred embodiment, the Tm-1 resistance gene is also to be found at the homozygous state.

The tolerance QTLs according to the invention, namely QTL1, QTL2 and QTL3, conferring the resistance to TBRFV when combined with the Tm-1 gene, and conferring tolerance to TBRFV in the absence of such a combination, are chosen from the ones present in the genome of seeds of HAZTBRFVRES1. A sample of this S. lycopersicum seed has been deposited by Hazera Seeds Ltd. Berurim, M.P. Shikmim 79837, Israel, pursuant to and in satisfaction of the requirements of the Budapest treaty on the International Recognition of the deposit of Microorganisms for the Purpose of Patent procedure ("the Budapest Treaty" with the National collection of Industrial, Food and Marine bacteria (NCIMB) (NCIMB, Ltd, Ferguson Building, Craibstone Estate, Bucksburn, Aberdeen AB21 9YA, united Kingdom) on 16 May 2017 under accession number 42758. A deposit of this tomato seed is maintained by Hazera Seeds Ltd. Berurim, M.P. Shikmim 79837, Israel.

The tolerance QTLs conferring the tolerance to TBRFV, and conferring the resistance when combined with Tm-1 gene, are located on chromosome 6 for QTL1, on chromosome 9 for QTL2 and on chromosome 11 for QTL3. They are more preferably located within a chromosomal interval of chromosome 6 which comprises the SNP TO-0005197 (SEQ ID No:1) and the SNP TO-0145581 (SEQ ID No:2) for QTL1, within a chromosomal interval of chromosome 9 which comprises the SNP TO-0180955 (SEQ ID No:3) and the SNP TO-0196109 (SEQ ID No:6) for QTL2 and within a chromosomal interval of chromosome 11 which comprises the SNP TO-0122252 (SEQ ID No:7) and the SNP TO-0162427 (SEQ ID No:18) for QTL3.

The specific polymorphisms corresponding to the SNPs (Single Nucleotide Polymorphism) referred to in this description, as well as the flanking sequences of these SNPs in the S. lycopersicum genome, are given in the experimental section (see tables 3 and 4) and the accompanying sequence listing. Their location with respect to the version 2.40 of the tomato genome, on chromosomes 6, 9 and 11, is indicated in table 3 and their flanking sequences are also illustrated in table 4, and in the sequence listing.

It is to be noted in this respect that, by definition, a SNP refers to a single nucleotide in the genome, which is variable depending on the allele which is present, whereas the flanking nucleotides are identical. For ease of clear identification of the position of the different SNPs, their position is given in tables 3 and 4, by reference to the tomato genome sequence in its version 2.40 and by reference to their flanking sequences, identified by SEQ ID number. In the sequence associated with a specific SNP in the present application, for example SEQ ID No:1 for the SNP TO-0005197, only one nucleotide within the sequence actually corresponds to the polymorphism, namely the $61^{st}$ nucleotide of SEQ ID No:1 corresponds to the polymorphic position of SNP TO-0005197, which can be T or C as indicated in table 4. The flanking sequences are given for positioning the SNP in the genome but are not part of the polymorphism as such.

The present inventors have identified that the tolerance QTLs responsible for the resistance or enhanced tolerance when combined with the Tm-1 gene, are to be found in the chromosomal regions mentioned above, by identifying the presence of sequences at different loci along said region, namely at 18 different loci defined by the 18 following SNPs: TO-0005197 (SEQ ID No:1) and TO-0145581 (SEQ ID No:2) for QTL1 on chromosome 6, TO-0180955 (SEQ ID No:3), TO-0196724 (SEQ ID No:4), TO-0145125 (SEQ ID No:5) and TO-0196109 (SEQ ID No:6) for QTL2 on chromosome 9 and TO-0122252 (SEQ ID No:7), TO-0144317 (SEQ ID No:8), TO-0142270 (SEQ ID No:9), TO-0142294 (SEQ ID No:10), TO-0142303 (SEQ ID No:11), TO-0142306 (SEQ ID No:12), TO-0182276 (SEQ ID No:13), TO-0181040 (SEQ ID No:14), TO-0123057

(SEQ ID No:15), TO-0125528 (SEQ ID No:16), TO-0162432 (SEQ ID No:17) and TO-0162427 (SEQ ID No:18) for QTL3 on chromosome 11.

These 18 SNPs are associated or genetically linked to at least one of the tolerance QTL. By association, or genetic association, and more specifically genetic linkage, it is to be understood that a genetic polymorphism of the marker (i.e. a specific allele of the SNP marker) and the phenotype of interest occur simultaneously, i.e. are inherited together, more often than would be expected by chance occurrence, i.e. there is a non-random association of the allele and of the genetic sequences responsible for the phenotype, as a result of their proximity on the same chromosome.

A molecular marker of the invention, either one of 18 markers disclosed above or alternative markers, are inherited with the phenotype of interest in preferably more than 90% of the meioses, preferably in more than 95%, 96%, 98% or 99% of the meioses.

According to another embodiment of the invention, the tolerance QTLs present in the genome of a plant, seed or cell of the invention are preferably to be found at least at one or more of the 18 loci encompassing said 18 SNPs mentioned above, namely the locus encompassing TO-0005197 (SEQ ID No:1), the locus encompassing TO-0145581 (SEQ ID No:2) for QTL1 on chromosome 6, the locus encompassing TO-0180955 (SEQ ID No:3), the locus encompassing TO-0196724 (SEQ ID No:4), the locus encompassing TO-0145125 (SEQ ID No:5), the locus encompassing TO-0196109 (SEQ ID No:6), for QTL2 on chromosome 9, the locus encompassing TO-0122252 (SEQ ID No:7), the locus encompassing TO-0144317 (SEQ ID No:8), the locus encompassing TO-0142270 (SEQ ID No:9), the locus encompassing TO-0142294 (SEQ ID No:10), the locus encompassing TO-0142303 (SEQ ID No:11), the locus encompassing TO-0142306 (SEQ ID No:12), the locus encompassing TO-0182276 (SEQ ID No:13), the locus encompassing TO-0181040 (SEQ ID No:14), the locus encompassing TO-0123057 (SEQ ID No:15), the locus encompassing TO-0125528 (SEQ ID No:16), the locus encompassing TO-0162432 (SEQ ID No:17) and the locus encompassing TO-0162427 (SEQ ID No:18) for QTL3 on chromosome 11.

In an embodiment, in a tomato plant according to the invention, the QTLs present in the genome of a plant, seed or cell of such tomato plant, and which are to be combined with the Tm-1 gene, are preferably to be found at least at one or more of the following loci: the locus encompassing TO-0005197, the locus encompassing TO-0145581 for QTL1 on chromosome 6, and/or the locus encompassing TO-0180955, the locus encompassing TO-0196724, the locus encompassing TO-0145125 and the locus encompassing TO-0196109 for QTL2 on chromosome 9.

In another embodiment of the invention, the QTLs present in the genome of a plant, seed or cell of the tomato plant, which are to be combined with the Tm-1 gene, are preferably to be found at least at one or more of the following loci: the locus encompassing TO-0122252, the locus encompassing TO-0144317, the locus encompassing TO-0142270, the locus encompassing TO-0142294, the locus encompassing TO-0142303, the locus encompassing TO-0142306, the locus encompassing TO-0182276, the locus encompassing TO-0181040, the locus encompassing TO-0123057, the locus encompassing TO-0125528, the locus encompassing TO-0162432 and the locus encompassing TO-0162427 for QTL3 on chromosome 11.

The alleles of the 18 SNPs linked to the tolerance QTLs conferring the TBRFV tolerance are allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and allele T of TO-0162427. The presence of the tolerance QTLs can be revealed by the presence of said specific alleles. The alleles of these SNPs can thus reflect the presence of the tolerance QTLs according to the invention, which are to be combined with the Tm-1 gene.

According to a preferred embodiment of the present invention, the QTLs conferring the tolerance to TBRFV, which are to be combined with the Tm-1 gene, are on one or more chromosomal intervals delimited by the SNPs as disclosed. According to this embodiment, the QTL1 is on a chromosomal interval of chromosome 6 delimited on one side by SNP TO-0005197 and on the other side by SNP TO-0145581.

According to another embodiment, the QTL2 is on a chromosomal interval of chromosome 9 delimited on one side by SNP TO-0180955 and on the other side by SNP TO-0196109.

According to another embodiment, the QTL3 is on a chromosomal interval of chromosome 11 delimited on one side by SNP TO-0122252 and on the other side by TO-0162427. More preferred chromosomal intervals of chromosome 11 within which QTL3 is to be found are the interval delimited by TO-0144317 and TO-0125528, the interval delimited by TO-0142270 and TO-0162432, the interval delimited by TO-0144317 and TO-0162432, and the interval delimited by TO-0142270 and TO-0125528. The even more preferred interval is the interval delimited by TO-0142270 and TO-0125528. Another preferred interval is the interval delimited by and comprising TO-0142294 and TO-0125528.

It is noted in this respect that specific positions in a chromosome can indeed be defined with respect to single nucleotide polymorphism, insofar as the flanking sequences of said SNPs are defined in order to unambiguously position them on the genome. The present inventors have used SNPs, identified by their flanking sequences, with different alleles, to identify and follow the QTLs of the present invention.

A chromosomal region delimited by two SNPs X and Y refers to the section of the chromosome lying between the positions of these two SNPs and comprising said SNPs, therefore the nucleotide sequence of this chromosomal region begins with the nucleotide corresponding to SNP X and ends with the nucleotide corresponding to SNP Y, i.e. the SNPs are comprised within the region they delimit, in the sense of the invention.

In a plant, seed or cell of the invention, the presence of the tolerance QTLs, which are to be combined with the Tm-1 resistance gene, is preferably characterized by TO-0005197 and/or TO-0145581 for the QTL1 on chromosome 6 and/or by TO-0180955, TO-0196724, TO-0145125 and/or TO-0196109 for the QTL2 on chromosome 9 and/or by TO-0122252, TO-0144317, TO-0142270, TO-0142294, TO-0142303, TO-0142306, TO-0182276, TO-0181040, TO-0123057, TO-0125528, TO-0162432 and TO-0162427, most preferably by TO-0142294, TO-0142303, TO-0142306, TO-0182276, TO-0181040, TO-0123057, TO-0125528, and even more preferably TO-0182276, for the QTL3 on chromosome 11.

When present homozygously in the genome of a tomato plant, QTL1 and/or QTL2 will confer independently and collectively fruit tolerance to TBRFV and QTL3 will confer leaf tolerance to TBRFV, unless combined with the Tm-1 resistance gene in order to confer resistance or enhanced tolerance to TBRFV according to the invention.

The tolerance QTLs as defined above are in combination with the Tm-1 gene, in the genome of a plant, seed or cell of the invention.

The Tm-1 gene may be present heterozygously or homozygously in the genome of a plant, seed or cell of the invention. It is however preferred that said gene be present homozygously.

The present inventors have also found suitable markers for detecting the presence of the Tm-1 gene in the genome of a plant, seed or cell of the invention. The presence of the Tm-1 resistance gene, which is to be combined with one or more tolerance QTLs, is preferably characterized by the SNP TO-0200838 (SEQ ID No: 21).

The allele of the SNP TO-0200838 corresponding to the Tm-1 gene is allele A of TO-0200838. The presence of the Tm-1 gene conferring the resistance to TBRFV when combined with at least one tolerance QTL can be revealed by the presence of said specific allele.

According to an embodiment, a *S. lycopersicum* plant, cell or seed according to the invention also comprises in its genome a Tm-2 resistance gene, especially Tm-2 or Tm-2² (also known as Tm-2a) allele. The Tm-2 and Tm-2² alleles are well-known to the skilled reader and described in detail in the literature. Such a Tm-2 or Tm-2² allele is either found homozygously or heterozygously in the genome of a plant, cell or seed according to the invention, but preferably heterozygously.

In a preferred embodiment, a plant of the invention comprises a Tm-2 gene, preferably a Tm-2² allele, on one of chromosome 9 homolog and QTL2 on the other homolog. Such a plant moreover comprises homozygously at least one of QTL1 and QTL3, more preferably QTL3. This plant also comprises the Tm-1 gene, either homozygously or heterozygously.

Alternatively, although less preferred, a plant, seed or cell according to the invention does not exhibit TMV or ToMV resistance insofar as the Tm-1 resistance gene does not provide TMV or ToMV resistance to most of the circulating TMV and ToMV strains, especially it does not comprise a Tm-2 resistance gene.

The invention encompasses tomato plants, comprising for example the genotype combinations according to table 1, wherein "Hom" means homozygous for the tolerance QTL or resistance gene, "Het" heterozygous for the tolerance QTL or resistance gene and "Ø" absence of the tolerance QTL or resistance gene.

TABLE 1 preferred genotypes according to the invention:

| # | QTL1 | QTL2 | QTL3 | Tm-1 |
|---|------|------|------|------|
| 1 | Hom | Ø | Ø | Het |
| 2 | Ø | Hom | Ø | Het |
| 3 | Ø | Ø | Hom | Het |
| 4 | Hom | Ø | Ø | Hom |
| 5 | Ø | Hom | Ø | Hom |
| 6 | Ø | Ø | Hom | Hom |
| 7 | Het | Ø | Hom | Het |
| 8 | Ø | Het | Hom | Het |
| 9 | Het | Het | Hom | Het |
| 10 | Het | Ø | Hom | Hom |

TABLE 1-continued preferred genotypes according to the invention:

| # | QTL1 | QTL2 | QTL3 | Tm-1 |
|---|------|------|------|------|
| 11 | Ø | Het | Hom | Hom |
| 12 | Het | Het | Hom | Hom |
| 13 | Hom | Ø | Hom | Het |
| 14 | Ø | Hom | Hom | Het |
| 15 | Hom | Ø | Hom | Hom |
| 16 | Ø | Hom | Hom | Hom |
| 17 | Hom | Het | Hom | Het |
| 18 | Hom | Het | Hom | Hom |
| 19 | Hom | Het | Ø | Het |
| 20 | Hom | Ø | Het | Het |
| 21 | Hom | Het | Het | Het |
| 22 | Hom | Het | Ø | Hom |
| 23 | Hom | Ø | Het | Hom |
| 24 | Hom | Het | Het | Hom |
| 25 | Het | Het | Het | Hom |
| 26 | Het | Het | Het | Het |

The presence at the homozygous or heterozygous state of the tolerance QTLs and Tm-1 gene can be detected with the different SNP markers disclosed in the present description.

Preferably, a *S. lycopersicum* plant according to the invention is a commercial plant or line. Such a commercial plant or line preferably also exhibits additional resistances such as nematode resistance trait (Mi-1 or Mi-j), as well as *Fusarium* and *Verticillium* resistances.

Other resistances or tolerances are also envisaged according to the invention.

According to a preferred embodiment, a plant of the invention is not resistant to Pepino Mosaic Virus (PepMV). According to another embodiment, a tomato plant of the invention is also resistant to PepMV.

According to still another embodiment, a plant of the invention is a determinate, indeterminate or semi-indeterminate plant, or seed or cell thereof, i.e. corresponding to determinate, indeterminate or semi-indeterminate growth habit.

By determinate, it is meant tomato plants which tend to grow their foliage first, then set flowers that mature into fruit if pollination is successful. All of the fruits tend to ripen on a plant at about the same time. Indeterminate tomatoes start out by growing some foliage, then continue to produce foliage and flowers throughout the growing season. These plants will tend to have tomato fruit in different stages of maturity at any given time. The semi-determinate tomatoes have a phenotype between determinate and indeterminate, they are typical determinate types except that grow larger than determinate varieties.

According to still another embodiment, a plant of the invention is used as a scion or as a rootstock in a grafting process. Grafting is a process that has been used for many years in crops such as cucurbitacea, but only more recently for tomato. Grafting may be used to provide a certain level of resistance to telluric pathogens or to certain nematodes. Grafting is therefore intended to prevent contact between the plant or variety to be cultivated and the infested soil. The variety of interest used as the graft or scion, optionally an F1 hybrid, is grafted onto the resistant plant used as the rootstock. The resistant rootstock remains healthy and provides, from the soils, the normal supply for the graft that it isolates from the diseases.

Moreover, the commercial plant of the invention gives rise to fruits in suitable conditions, which are at least 25 grams at full maturity, preferably at least 100 g at full maturity and or even more preferred at least 200 g at full maturity.

As detailed above, the invention is directed to *S. lycopersicum* plants, exhibiting the TBRFV resistance phenotype, as well as to seeds giving rise to those plants.

A plant or seed according to the invention may be a progeny or offspring of an hybrid between a plant grown from the deposited seeds HAZTBRFVRES1, deposited at the NCIMB under the accession number NCIMB 42758 and a *S. lycopersicum* plant bearing the Tm-1 gene. Plants grown from the deposited seeds are indeed homozygous for the tolerance QTLs, they thus bear in their genome the QTLs of interest on each of the homologues of chromosome 6, 9 and 11. They can be used to combine these QTLs with the Tm-1 gene, as illustrated in the examples of the present application, by crossing, selfing and/or backcrossing steps.

With regard to the deposited seeds of HAZTBRFVRES1 (NCIMB 42758), it is noted that these seeds do not correspond to a plant variety, they are not homozygous for most of the genes except the tolerance QTLs; their phenotype is thus not fixed during propagation, except for the foliar and fruit tolerance of the invention; such that their phenotypic traits segregate during propagation, with the exception of TBRFV foliar and fruit tolerance.

According to an embodiment of the invention, the plant, seed or cell is resistant more specifically to the Israeli strain of TBRFV. By Israeli strain of TBRFV, it is meant a strain of TBRFV as first identified and sequenced by Luria et al, namely a strain infecting tomatoes and having a sequence with a very high degree of sequence identity with KX619418 (SEQ ID No:26), namely a degree of sequence identity with SEQ ID No:26 which is higher than the degree of sequence identity with SEQ ID No:25, thus a sequence identity above 99%, preferably above 99.5% or even above. A plant, seed or cell of the invention is thus according to an embodiment more resistant to the Israeli strain than to the Jordanian strain, for example it is resistant only to the Israeli strain.

The invention is also directed to plants or seeds obtainable by transferring the tolerance QTLs from a *S. lycopersicum* plant comprising the tolerance QTLs, representative seeds thereof were deposited under NCIMB accession NCIMB-42758, into another *S. lycopersicum* genetic background comprising the Tm-1 gene, for example by crossing said plant with a tomato plant parent comprising the Tm-1 gene, and selection of plants bearing the tolerance QTLs, or at least one of them, and the Tm-1 gene. In such crossing, QTL1, QTL2 and/or QTL 3 or any combination thereof could be transferred. According to one embodiment, QTL1 only, or QTL2 only, or both QTLs 1 and 2 are transferred. According to another embodiment, QTL 3 is transferred. Alternatively, QTL1 and QTL3, QTL2 and QTL3 or QTL1, QTL2 and QTL3, preferably QTL2 and QTL3 are transferred from the deposited seeds of HAZTBRFVRES1 (NCIMB 42758) into a tomato genetic background comprising the Tm-1 gene. Preferably, the obtained progeny is selfed, such that at least one tolerance QTL is homozygously present in the obtained genome.

According to a preferred embodiment, the plant comprises at least two QTLs chosen from QTL1, QTL2 and QTL3, at least one being heterozygous; preferably at least one is homozygous.

It is noted that the seeds or plants of the invention may be obtained by different processes, and are not exclusively obtained by means of an essentially biological process.

According to such an aspect, the invention relates to a tomato plant or seed, preferably a non-naturally occurring tomato plant or seed, which may comprise two or more mutations in its genome, which provides the plant with a Tomato Brown Rugose Fruit virus resistance, wherein at least one mutation is, for example, as present in the genome of plants of which a representative sample was deposited with the NCIMB under deposit number NCIMB 42758, and at least another mutation is on chromosome 2 and corresponds to the sequence of a Tm-1 gene.

In another embodiment, the invention relates to a method for obtaining a tomato plant or seed carrying two or more mutations in its genome, which provides the plant with a resistance to Tomato Brown Rugose Fruit virus. Such a method is illustrated in example 4 and may comprise:

a) treating M0 seeds of a tomato plant to be modified with a mutagenic agent to obtain M1 seeds;
b) growing plants from the thus obtained M1 seeds to obtain M1 plants;
c) producing M2 seeds by self-fertilisation of M1 plants; and
d) optionally repeating step b) and c) n times to obtain M1+n seeds.

The M1+n seeds are grown into plants and submitted to Tomato Brown Rugose Fruit virus infection. The surviving plants, or those with the milder symptoms of TBRFV infection, are multiplied one or more further generations while continuing to be selected for their resistance to Tomato Brown Rugose Fruit virus. The M0 seeds are for example from a tomato plant bearing the Tm-1 gene.

In this method, the M1 seeds of step a) can be obtained via chemical mutagenesis such as EMS mutagenesis. Other chemical mutagenic agents include but are not limited to, diethyl sufate (des), ethyleneimine (ei), propane sultone, N-methyl-N-nitrosourethane (mnu), N-nitroso-N-methylurea (NMU), N-ethyl-N-nitrosourea(enu), and sodium azide.

Alternatively, the mutations are induced by means of irradiation, which is for example selected from x-rays, fast neutrons, UV radiation.

In another embodiment of the invention, the mutations are induced by means of genetic engineering. Such mutations also include the integration of sequences corresponding to the tolerance QTLs and the Tm-1 gene, as well as the substitution of residing sequences by alternative sequences conferring the TBRFV resistance. Preferably, the mutations are the integration of one or more of QTL1, QTL2 and QTL3 as described above, in replacement of the homologous sequences of a *S. lycopersicum* plants, and integration of the Tm-1 gene, preferably on chromosome 2. Even more preferably, the mutation includes the substitution of the sequence comprised within SNP TO-0122252 (SEQ ID No:7) and SNP TO-0162427 (SEQ ID No:18) on chromosome 11 of *S. lycopersicum* genome, or a fragment thereof, by the homologous sequence on chromosome 11 present in the genome of a plant of which a representative sample was deposited with the NCIMB under deposit number NCIMB 42758, and also includes the incorporation of the Tm-1 resistance gene, wherein the combination of the integrated sequences confer resistance to TBRFV. The substitution on chromosome 11 corresponding to QTL3 is preferably homozygous, the incorporation of Tm-1 gene can be homozygous or heterozygous.

The genetic engineering means which can be used include the use of all such techniques called New Breeding Techniques which are various new technologies developed and/or used to create new characteristics in plants through genetic variation, the aim being targeted mutagenesis, targeted introduction of new genes or gene silencing (RdDM). Example of such new breeding techniques are targeted sequence changes facilitated through the use of Zinc finger nuclease (ZFN) technology (ZFN-1, ZFN-2 and ZFN-3, see U.S. Pat. No. 9,145,565), Oligonucleotide directed mutagenesis (ODM), Cisgenesis and intragenesis, Grafting (on GM rootstock), Reverse breeding, Agro-infiltration (agro-infiltration "sensu stricto", agro-inoculation, floral dip), Transcription Activator-Like Effector Nucleases (TALENs, see U.S. Pat. Nos. 8,586,363 and 9,181,535), the CRISPR/Cas system (see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641), engineered meganuclease re-engineered homing endonucleases, DNA guided genome editing (Gao et al., Nature Biotechnology (2016)), and Synthetic genomics. A major part of targeted genome editing, another designation for New Breeding Techniques, is the applications to induce a DNA double strand break (DSB) at a selected location in the genome where the modification is intended. Directed repair of the DSB allows for targeted genome editing. Such applications can be utilized to generate mutations (e.g., targeted mutations or precise native gene editing) as well as precise insertion of genes (e.g., cisgenes, intragenes, ortransgenes). The applications leading to mutations are often identified as site-directed nuclease (SDN) technology, such as SDN1, SDN2 and SDN3. For SDN1, the outcome is a targeted, non-specific genetic deletion mutation: the position of the DNA DSB is precisely selected, but the DNA repair by the host cell is random and results in small nucleotide deletions, additions or substitutions. For SDN2, a SDN is used to generate a targeted DSB and a DNA repair template (a short DNA sequence identical to the targeted DSB DNA sequence except for one or a few nucleotide changes) is used to repair the DSB: this results in a targeted and predetermined point mutation in the desired gene of interest. As to the SDN3, the SDN is used along with a DNA repair template that contains new DNA sequence (e.g. gene). The outcome of the technology would be the integration of that DNA sequence into the plant genome. The most likely application illustrating the use of SDN3 would be the insertion of cisgenic, intragenic, or transgenic expression cassettes at a selected genome location. A complete description of each of these techniques can be found in the report made by the Joint Research Center (JRC) Institute for Prospective Technological Studies of the European Commission in 2011 and titled "New plant breeding techniques—State-of-the-art and prospects for commercial development".

The invention in another aspect also concerns any plant likely to be obtained from seed or plants of the invention as described above, and also plant parts of such a plant, and most preferably explant, scion, cutting, seed, fruit, root, rootstock, pollen, ovule, embryo, protoplast, leaf, anther, stem, petiole, and any other plants part, wherein said plant, explant, scion, cutting, seed, fruit, root, rootstock, pollen, ovule, embryo, protoplast, leaf, anther, stem, petiole, and/or plant part is obtainable from a seed or plant according to the first aspect of the invention, i.e. bearing one, two or three of the tolerance QTLs of interest, in combination with the Tm-1 gene. These plant parts, inter alia explant, scion, cutting, seed, fruit, root, rootstock, pollen, ovule, embryo, protoplast, leaf, anther, stem or petiole, comprise in their genome the tolerance QTLs conferring the phenotype of fruit and/or foliar tolerance to TBRFV when present homozygously in the absence of the Tm-1 gene, and which confer TBRFV resistance when present in combination with the Tm-1 gene.

The tolerance QTLs referred to in this aspect of the invention are those defined above in the context of plants of the invention. The different features of the tolerance QTLs defined in relation with the first aspect of the invention apply mutatis mutandis to this aspect of the invention. The tolerance QTLs are thus preferably chosen from those present in the genome of a plant corresponding to the deposited material HAZTBRFVRES1 (NCIMB accession number 42758). They are advantageously characterized by the presence of allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and/or allele T of TO-0162427, depending of the QTL of interest, and preferably by the presence of this or these alleles homozygously.

The presence of the Tm-1 resistance gene, which is to be combined with one or more tolerance QTLs, is preferably characterized by the SNP TO-0200838 (SEQ ID 21), more specifically by allele A of TO-0200838.

The TBRFV resistance is advantageously a resistance to the Israeli strain of TBRFV.

The invention is also directed to cells of S. lycopersicum plants, such that these cells comprise, in their genome, the combination of the Tm-1 gene, either homozygously or heterozygously, and at least one of the tolerance QTLs conferring the phenotype of fruit and/or foliar tolerance to TBRFV when present homozygously in the absence of the Tm-1 gene, and which confer TBRFV resistance when present in combination with the Tm-1 gene. The tolerance QTLs are those already defined in the description, they are characterized by the same features and preferred embodiments already disclosed with respect to the plants and seeds according to the preceding aspects of the invention. The presence of these tolerance QTLs can be revealed by the techniques disclosed above and well known to the skilled reader. It can inter alia be determined whether the QTLs are present homozygously or heterozygously in the genome of such a cell of the invention. They are advantageously characterized by the presence of allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and/or allele T of TO-0162427, depending of the tolerance QTL of interest, and preferably by the presence of this or these alleles simultaneously on each chromosome, i.e. homozygously. Preferably at least one QTL is present homozygously and at least one QTL is present heterozygously.

According to an embodiment, the QTL2 on chromosome 9 is present heterozygously in a cell according to the invention. The other homolog of chromosome 9 according to a specific embodiment comprises a Tm-2 or Tm-2$^2$ gene or allele. Such a cell thus exhibits resistance to TMV/ToMV.

Preferred genotypes for a cell of the invention are disclosed in table 1.

The presence of the Tm-1 resistance gene, which is to be combined with one or more tolerance QTLs, is preferably characterized by the SNP TO-0200838, more specifically by allele A of TO-0200838.

Cells according to the invention can be any type of S. lycopersicum cell, inter alia an isolated cell and/or a cell capable of regenerating a whole *S. lycopersicum* plant, bearing one or more of the tolerance QTLs of interest, preferably two tolerance QTLs, and the Tm-1 gene.

The present invention is also directed to a tissue culture of non-regenerable or regenerable cells of the plant as defined above according to the present invention; preferably, the regenerable cells are derived from embryos, protoplasts, meristematic cells, callus, pollen, leaves, anthers, stems, petioles, roots, root tips, fruits, seeds, flowers, cotyledons, and/or hypocotyls of the invention, and the cells contain the combination of the Tm-1 gene and one, two or three of the tolerance QTLs of interest, in whenever combination, homozygously or heterozygously in their genome, said QTLs conferring, when present homozygously fruit tolerance to TBRFV for QTL1 and/or QTL2, foliar tolerance to TBRFV for QTL3, and confer when present in combination with Tm-1, resistance or enhanced tolerance to TBRFV.

The tissue culture will preferably be capable of regenerating plants having the physiological and morphological characteristics of the foregoing tomato plant, and of regenerating plants having substantially the same genotype as the foregoing tomato plant. The present invention also provides tomato plants regenerated from the tissue cultures of the invention.

The invention also provides a protoplast of the plant defined above, or from the tissue culture defined above, said protoplast containing the combination of the Tm-1 gene and the tolerance QTLs conferring the TBRFV resistance.

According to another aspect, the present invention is also directed to the use of a tomato plant of the invention, comprising preferably homozygously at least one of the QTLs of the invention and also comprising the Tm-1 gene, also preferably homozygously, as a breeding partner in a breeding program for obtaining *S. lycopersicum* plants having TBRFV resistance. Indeed, such a breeding partner harbors homozygously in its genome at least one of the tolerance QTLs. By crossing this plant with a tomato plant, especially a line, it is thus possible to transfer one, two or the three tolerance QTLs, as well as the Tm-1 gene, to the progeny. A plant according to the invention can thus be used as a breeding partner for introgressing the tolerance QTLs and the Tm-1 gene into a *S. lycopersicum* plant or germplasm. Although a plant or seed bearing the tolerance QTLs or the Tm-1 gene heterozygously, can also be used as a breeding partner as detailed above, the segregation of the phenotype is likely to render the breeding program more complex.

The introgressed tolerance QTLs and Tm-1 gene will advantageously be introduced into varieties that contain other desirable genetic traits such as resistance to disease, especially resistance to TMV/ToMV, early fruit maturation, drought tolerance, fruit shape, and the like.

The invention is also directed to the use of a plant or seed comprising at least one of the tolerance QTLs, preferably homozygously as for example a plant or seed of *S. lycopersicum*, deposited at the NCIMB under the accession number NCIMB 42758, or progeny thereof, bearing homozygously the QTLs conferring the tolerance to TBRFV infection, as a breeding partner in a breeding program with *S. lycopersicum* plants comprising the Tm-1 gene. Such a breeding program allows to obtain *S. lycopersicum* plant or seed resistant to TBRFV.

In such a breeding program, the selection of the progeny displaying the desired phenotype of TBRFV resistance, or bearing at least one of the tolerance QTLs and the Tm-1 gene, can advantageously be carried out on the basis of the alleles of the SNP markers, especially the SNP markers disclosed above.

A progeny of the plant is preferably selected on the presence of allele T of TO-0005197 and/or allele C of TO-0145581 for the presence of QTL1 on chromosome 6, allele G of TO-0180955, allele C of TO-0196724, allele G of TO-0145125 and/or allele G of TO-0196109 for the presence of QTL2 on chromosome 9, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and/or allele T of TO-0162427 for the presence of QTL3 on chromosome 11. The progeny of the plant is preferably selected on the presence of the same allele on both homologues of each chromosome.

With respect to the presence of the Tm-1 gene, a progeny is preferably selected on the basis of allele A of TO-0200838.

The selection can alternatively be made on the basis of the presence of any one of the alleles of the 18 SNPs linked to tolerance QTLs, or a combination of these alleles, in addition to the selection on the presence of the Tm-1 gene. Such selection will be made on the presence of the alleles of interest in a genetic material sample of the plant to be selected. The presence of these alleles indeed confirms the presence of the tolerance QTLs at the loci defined by said SNPs. Moreover, further to point mutation or recombination event, it is conceivable that at least 1 or 2 of these alleles is lost, the remaining of the chromosomal fragment bearing the tolerance QTLs.

A plant according to the invention, is thus particularly valuable in a marker assisted selection for obtaining commercial tomato lines and varieties, having the improved phenotype of the invention.

The invention is also directed to a method for identifying, detecting and/or selecting *S. lycopersicum* plants resistant to TBRFV, capable of inhibiting, reducing or delaying the replication of the virus and/or reducing the virus titer in the plant. Such a method comprises the step of detecting, in a plant to be tested or selected, the combination of the Tm-1 gene and at least one of the tolerance QTLs, wherein said QTL(s) is preferably present homozygously. The method may thus comprise the detection of at least one of the following markers: allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 or allele T of TO-0162427, preferably in homozygous state, in a genetic material sample of the plant to be identified and/or selected, as well as the detection of the Tm-1 gene. Preferably, the tolerance QTL is QTL3 and it is detected by the presence of T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and allele T of TO-0162427, preferably in homozygous state.

Advantageously, the method comprises the detection of two tolerance QTLs, at least one being heterozygous, and preferably at least one being homozygous.

The invention is also directed to a method for detecting or selecting S. lycopersicum plants having at least one of the tolerance QTL in combination with the Tm-1 gene, i.e. having the marker alleles disclosed in this description, wherein the detection or selection is made on condition of TBRFV infection comprising inoculation of TBRFV on the plants to be tested, and detection of the inhibition, reduction or delay of the viral replication and/or reduction of the virus titer in the plant.

The invention is further directed to a method for detecting and or selecting S. lycopersicum plants having the Tm-1 gene and at least one of the tolerance QTLs, wherein the detection of the tolerance QTL is based on the detection of any molecular marker revealing the presence of said QTLs. Indeed, the identification and then the use of molecular markers, distinct from the 18 SNPs disclosed above, can be easily done by the skilled artisan. The tolerance QTLs can thus be identified through the use of different, alternative markers.

The invention is thus also directed to a method for detecting and/or selecting S. lycopersicum plants resistant to TBRFV, inhibiting, reducing or delaying the replication of the virus, said method comprising the steps of:
a) Assaying tomato plant for the combination in its genome of
   the presence of the Tm-1 resistance gene on chromosome 2, and
   the presence of at least one genetic marker genetically linked to a tolerance QTL chosen from QTL3 on chromosome 11, QTL1 on chromosome 6 and QTL2 on chromosome 9,
b) Selecting a plant comprising in its genome the Tm-1 gene and the genetic marker, and the tolerance QTL linked to said genetic marker,
wherein the chosen QTL and the genetic marker are to be found, for QTL1, on chromosome 6, within the chromosomal region delimited by TO-0005197 (SEQ ID No:1) and TO-015581 (SEQ ID No:2), for QTL2, on chromosome 9, within the chromosomal region delimited by TO-0180955 (SEQ ID No:3) and TO-0196109 (SEQ ID No:6) and for QTL3, on chromosome 11, within the chromosomal region delimited by TO-0122252 (SEQ ID No:7) and TO-0162427 (SEQ ID No:18).

The genetic marker under consideration is preferably a SNP marker. The tolerance QTLs are as defined in this description, and as found in the genome of a plant of the seeds HAZTBRFVRES1 NCIMB accession number 42758.

According to a still another aspect, the invention also concerns methods or processes for the production of S. lycopersicum plants having TBRFV resistance, especially commercial plants and inbred parental lines. The present invention is indeed also directed to transferring one or more of the tolerance QTLs and/or the Tm-1 gene, in order to confer TBRFV resistance, to other tomato varieties, or other species or inbred parental lines, especially resistance to the Israeli strain of TBRFV, and is useful for producing new types and varieties of tomatoes. These methods comprise the transfer of at least one tolerance QTL and Tm-1 gene to another plant, as well as transfer of at least one tolerance QTL to another Tm-1 bearing plant.

A method or process for the production of a plant having these features may for example comprise the following steps:

a) Crossing a plant grown from a deposited seeds NCIMB 42758, or progeny thereof, bearing QTL1, QTL2 and/or QTL3 conferring TBRFV tolerance, and a S. lycopersicum plant, preferably devoid of said QTL(s), and bearing the Tm-1 gene,
b) Selecting a plant in the progeny thus obtained, bearing one, two or three of the tolerance QTL1, QTL2 and/or QTL3 in combination with the Tm-1 gene;
c) Optionally self-pollinating one or several times the plant obtained at step b) and selecting in the progeny thus obtained a plant having resistance to TBRFV.

The TBRFV resistance delays, reduces or inhibits the replication or multiplication of the TBRF virus, and/or reduces the virus titer in the plant.

Alternatively, the method or process may comprise instead of step a) the following steps:
a1) Crossing a plant grown from the deposited seeds NCIMB 42758 or progeny thereof, bearing QTL1, QTL2 and/or QTL3 conferring TBRFV tolerance, and a S. lycopersicum plant, preferably devoid of said QTL(s), and bearing the Tm-1 gene, thus generating F1 hybrids,
a2) Increasing the F1 hybrid by means of selfing to create F2 population, In the above methods or processes, SNPs markers are preferably used in steps b) and/or c), for selecting plants bearing the tolerance QTL and/or the Tm-1 gene.

The SNP markers for the tolerance QTLs are preferably one or more of the 18 SNP markers already disclosed in the present description, including all combinations thereof as mentioned elsewhere in the application.

According to a preferred embodiment, the selection for plants having a tolerance QTL is made on the basis of TO-0182276, or on the basis of at least one of TO-0142294, TO-0142303, TO-0142306, TO-0182276, TO-0181040, TO-0123057, TO-0125528.

By selecting a plant on the basis of the allele of one or more SNPs, it is to be understood that the plant is selected as having a tolerance QTL when the allele of the SNP(s) is (are) the allele corresponding to the allele of the HAZT-BRFVRES1 parent for this SNP and not the allele of the initial S. lycopersicum plant devoid of said QTLs. For example, a plant can be selected as having the tolerance QTLs of the invention, when allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and/or allele T of TO-0162427 is detected.

Preferably, the S. lycopersicum plant of step a) or a1) is an elite line, used in order to obtain a plant with commercially desired traits or desired horticultural traits. This plant has preferably been previously modified in order to incorporate the Tm-1 gene. According to an embodiment, this plant is susceptible to TBRFV. This plant preferably comprises the Tm-1 gene, and preferably also the Tm-2 gene, or its Tm-$2^2$ allele.

The selection of plants bearing the Tm-1 gene is preferably carried out by detection of allele A of SNP TO-0200838.

A method or process as defined above may advantageously comprise backcrossing steps, preferably after step c), in order to obtain plants having all the characterizing features of *S. lycopersicum* plants.

Consequently, a method or process for the production of a plant having these features may also comprise the following additional steps:
d) Backcrossing the resistant plant selected in step b) or c) with a *S. lycopersicum* plant;
e) Selecting a plant bearing one, two or three of the tolerance QTL1, QTL2 and/or QTL3 in combination with the Tm-1 gene.

The plant used in step a), namely the plant corresponding to the deposited seeds can be a plant grown from the deposited seeds; it may alternatively be any plant according to the $1^{st}$ aspect of the invention, bearing the QTLs conferring the phenotype, preferably bearing at least one of these sequences homozygously. In such a case, the plant is crossed in step a) with a *S. lycopersicum* plant, preferably devoid of said QTL(s), but not necessarily bearing the Tm-1 gene.

At step e), SNPs markers can be used for the selection of plants bearing a tolerance QTL and a Tm-1 gene; the SNP markers which can be used are for example those described in the previous sections of this description.

It is to be noted that, when plants having homozygously at least one tolerance QTL are to be selected, the selection is to be made on the basis of one or more of the SNPs linked to the tolerance QTLs, on the presence of the alleles representative of the QTLs, namely the alleles of the HAZTBRFVRES1 parent, coupled to the absence of the alleles representative of the recurrent susceptible *S. lycopersicum* parent. When plants having heterozygously at least one tolerance QTL are to be selected, the selection is to be made on the basis of one or more of the SNPs linked to the tolerance QTLs, on the presence of both alleles of the SNPs, i.e. the allele of the HAZTBRFVRES1 parent, and the allele of the recurrent susceptible *S. lycopersicum* parent.

The plant selected at step b), c) or e) is preferably a commercial plant, especially a plant having fruits which weigh at least 25 g, at least 100 g or at least 200 g at full maturity in normal culture conditions. Preferably, steps d) and e) are repeated at least twice and preferably three times, not necessarily with the same *S. lycopersicum* plant. Said *S. lycopersicum* plant is preferably a breeding line.

Resistance to nematode trait or resistance to ToMV may additionally be selected, at each selection step of the processes disclosed above.

The self-pollination and backcrossing steps may be carried out in any order and can be intercalated, for example a backcross can be carried out before and after one or several self-pollinations, and self-pollinations can be envisaged before and after one or several backcrosses.

The selection of the progeny having the desired TBRFV resistance, which delays, reduces and/or inhibits the replication of the virus, and/or reduces the virus titer in the plant, can also be made on the basis of the comparison of the Tomato Brown Rugose Fruit virus resistance from the *S. lycopersicum* parent, through protocols as disclosed inter alia in the examples.

The method used for allele detection can be based on any technique allowing the distinction between two different alleles of a SNP, on a specific chromosome.

The present invention also concerns a plant obtained or obtainable by such a method. Such a plant is indeed a *S. lycopersicum* plant having the TBRFV resistance according to the first aspect of the invention.

In all the methods and processes according to the invention, the initial TBRFV-susceptible *S. lycopersicum* plant can be determinate, indeterminate or semi-determinate.

As already disclosed, the tomato plants according to the invention are preferably also resistant to Tomato Mosaic Virus, to nematodes, and to *Fusarium* and *Verticillium*. In order to obtain such plants in the processes and methods of the invention, the *S. lycopersicum* parents used in the breeding schemes are preferably bearing sequences conferring resistance to Tomato Mosaic Virus, to nematodes, and to *Fusarium* and *Verticillium*; and the selection steps are carried out to select plants having these resistance sequences, in addition to the tolerance QTL(s) and Tm-1 gene.

The invention is also directed to a method for breeding *S. lycopersicum* plants having resistance to TBRFV, comprising the steps of crossing a plant grown from the deposited seeds NCIMB 42758 or progeny thereof bearing QTL1, QTL2 and/or QTL3 conferring TBRFV tolerance, with a *S. lycopersicum* plant bearing the Tm-1 gene.

The present invention is also directed to a *S. lycopersicum* plant and seed obtainable by any of the methods and processes disclosed above.

Any *S. lycopersicum* seed of the invention is preferably coated or pelleted with individual or combined active species such as plant nutrients, enhancing microorganisms, or products for disinfecting the environment of the seeds and plants. Such species and chemicals may be a product that promotes the growth of plants, for example hormones, or that increases their resistance to environmental stresses, for example defense stimulators, or that stabilizes the pH of the substrate and its immediate surroundings, or alternatively a nutrient.

They may also be a product for protecting against agents that are unfavorable toward the growth of young plants, including herein viruses and pathogenic microorganisms, for example a fungicidal, bactericidal, hematicidal, insecticidal or herbicidal product, which acts by contact, ingestion or gaseous diffusion; it is, for example, any suitable essential oil, for example extract of thyme. All these products reinforce the resistance reactions of the plant, and/or disinfect or regulate the environment of said plant. They may also be a live biological material, for example a nonpathogenic microorganism, for example at least one fungus, or a bacterium, or a virus, if necessary with a medium ensuring its viability; and this microorganism, for example of the *pseudomonas, bacillus, trichoderma, clonostachys, fusarium, rhizoctonia*, etc. type stimulates the growth of the plant, or protects it against pathogens.

In all the previous methods and processes, the identification of the plants bearing homozygously the tolerance QTLs could be done by the detection of at least one of the alleles linked with each of the QTLs, but also in combination with the absence of the other allelic form of the SNPs of the present invention. As such, the identification of a plant bearing homozygously QTL3 of the present invention will be based on the identification of allele T of TO-0122252, and/or allele C of TO-0144317, and/or allele T of TO-0142270, and/or allele G of TO-0142294, and/or allele A of TO-0142303, and/or allele A of TO-0142306, and/or allele G of TO-0182276, and/or allele G of TO-0181040, and/or allele G of TO-0123057, and/or allele A of TO-0125528, and/or allele C of TO-0162432 and/or allele T of TO-0162427 as well as the absence of allele A of TO-0122252, allele T of TO-0144317, allele C of TO-0142270, allele A of TO-0142294, allele C of TO-0142303, allele G of TO-0142306, allele A of TO-0182276, allele A of TO-0181040, allele T of TO-0123057, allele G of TO-0125528, allele T of TO-0162432 and allele C of TO-0162427.

When plants bearing heterozygously one of the tolerance QTL, preferably bearing heterozygously the tolerance QTL2 are to be selected, the identification implies the detection of allele G of TO-0180955 and/or allele C of TO-0196724 and/or allele G of TO-0145125 and/or allele G of TO-0196109 as well as, simultaneously the detection of allele A of TO-0180955, allele T of TO-0196724, allele A of TO-0145125 and allele T of TO-0196109.

In view of the ability of the resistant plants of the invention to restrict the damages caused by TBRFV infection, to reduce the virus titer and to delay, reduce and/or inhibit the viral replication, and thus its propagation, they are advantageously grown in an environment infested or likely to be infested or infected by TBRFV, especially the Israeli strain or isolate; in these conditions, the resistant plants of the invention produce more marketable tomatoes than susceptible plants. They moreover restrict the spread of the virus to other fields, thus protect less resistant plants, therefore indirectly improving also their yield.

The invention is thus also directed to a method for improving the yield of tomato plants in an environment infested, or likely to be infected by TBRFV, especially the Israeli strain or isolate, comprising growing TBRFV-resistant tomato plants according to the invention, thus comprising in their genome at least one tolerance QTL, i.e. QTL1, QTL2, and/or QTL3 as defined in WO2018/219941 on chromosome 6, 9 and 11 respectively, in combination with the Tm-1 gene, either homozygously or heterozygously. Preferably at least one of the tolerance QTL is present homozygously. According to another embodiment, at least one is present heterozygously, preferably with another one present homozygously. Preferably, the method comprises a first step of choosing or selecting a tomato plant having at least one of the tolerance QTLs and the Tm-1 gene. The method can also be defined as a method of increasing the productivity of a tomato field, tunnel, greenhouse or glasshouse.

As disclosed in the preceding aspect, the tomato plant to be grown preferably also comprises a Tm-2 or Tm-$2^2$ allele, preferably heterozygously. The preferred genotypes of the tomato plant or seed to be grown are illustrated in table 1.

According to a preferred embodiment, the method comprises growing a tomato plant comprising QTL3 as defined above on chromosome 11, preferably homozygously, and a Tm-1 gene. The invention is also directed to a method for reducing the loss on tomato production in condition of TBRFV infestation or infection, comprising growing a TBRFV-resistant tomato plant as defined above.

These methods are particularly valuable for a population of tomato plants, either in a field, in tunnels, greenouses or in glasshouses.

Alternatively, said methods for improving the yield or reducing the loss on tomato production may comprise a first step of identifying tomato plants resistant to TBRFV and comprising in their genome a tolerance QTL on chromosome 6, 9 and/or 11, homozygously or heterozygously, in combination with a Tm-1 gene, and then growing said resistant plants in an environment infested or likely to be infested by the virus. Preferably, the plants comprise homozygously a tolerance QTL on chromosome 11 in combination with the Tm-1 gene, the tolerance QTL on chromosome 9 heterozygously and the Tm-2 or Tm-$2^2$ allele heterozygously.

According to a preferred embodiment, the plants to be identified at the first step comprise allele G of TO-0182276.

The resistant plants of the invention are also able to restrict and even inhibits the growth of TBRFV, especially the Israeli isolate or strain of TBRFV, thus limiting the infection of further plants and the propagation of the virus. Accordingly, the invention is also directed to a method of protecting a field, tunnel, greenhouse or glasshouse, or any other type of plantation, from TBRFV infestation, or of at least limiting the level of infestation by TBRFV of said field, tunnel, greenhouse or glasshouse or of limiting the spread of TBRFV in a field, tunnel, greenhouse or glasshouse, especially in a tomato field. Such a method preferably comprises the step of growing a resistant plant of the invention, i.e. a plant comprising in its genome a tolerance QTL on chromosome 6, 9 and/or 11, preferably homozygously, and the Tm-1 gene. The plant of the invention to be used preferably comprises QTL3 on chromosome 11; more preferably the plant exhibits allele G of TO-0182276. Other preferred resistant plants have one of the genomic combinations disclosed in table 1.

Preferably, the method comprises a first step of choosing or selecting a tomato plant having a tolerance QTL, especially QTL3 on chromosome 11, and Tm-1 resistance gene.

The methods may also comprise a subsequent step of harvesting tomatoes.

The invention also concerns the use of a plant resistant to TBRFV for controlling TBRFV infection or infestation in a field, tunnel, greenhouse or glasshouse, or other plantation; such a plant is a plant of the invention, comprising in its genome at least one of the tolerance QTL as defined above, preferably homozygously, on chromosomes 6, 9 and/or 11 and the Tm-1 gene. In a preferred embodiment, the plant comprises in its genome two tolerance QTLs, at least one heterozygously, for example one heterozygously and one homozygously.

According to this use, the plants of the invention are therefore used for protecting a field, tunnel, greenhouse or glasshouse from TBRFV infestation. The plants of the invention to be used preferably comprises QTL3 on chromosome 11; more preferably they exhibit allele G of TO-0182276. Other preferred resistant plants have one of the genomic combinations disclosed in table 1. The TBRFV is according to a preferred embodiment the Israeli strain or isolate of TBRFV.

The tolerance QTLs are preferably those present in the genome of a plant of the seed HAZTBRFVRES1 NCIMB 42758.

LEGEND OF FIGURES

FIG. 1: Results of the first ELISA tests conducted at 45 DPI ("Microlab" $1^{st}$ scoring at 45 DPI) illustrating the presence or absence of TBRFV coat protein in leaves of tested plants.

This figure reports the optical density, as measured at 405 nm in the ELISA test, for 4 different plants.

Figure 2:
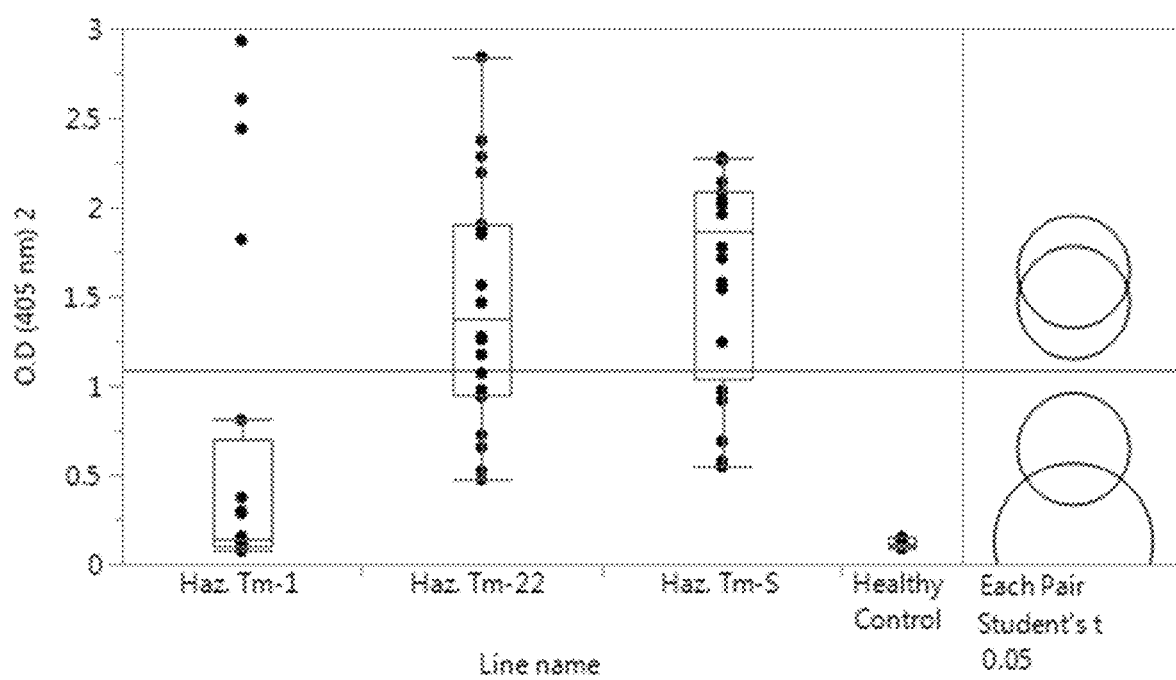

FIG. 2: Results of the ELISA tests conducted at 75 DPI ("Microlab" $2^{nd}$ scoring at 75 DPI) illustrating the presence or absence of TBRFV coat protein in leaves of tested plants.

This figure reports the optical density, as measured at 405 nm in the ELISA test, for 4 different plants.

Figure 3:
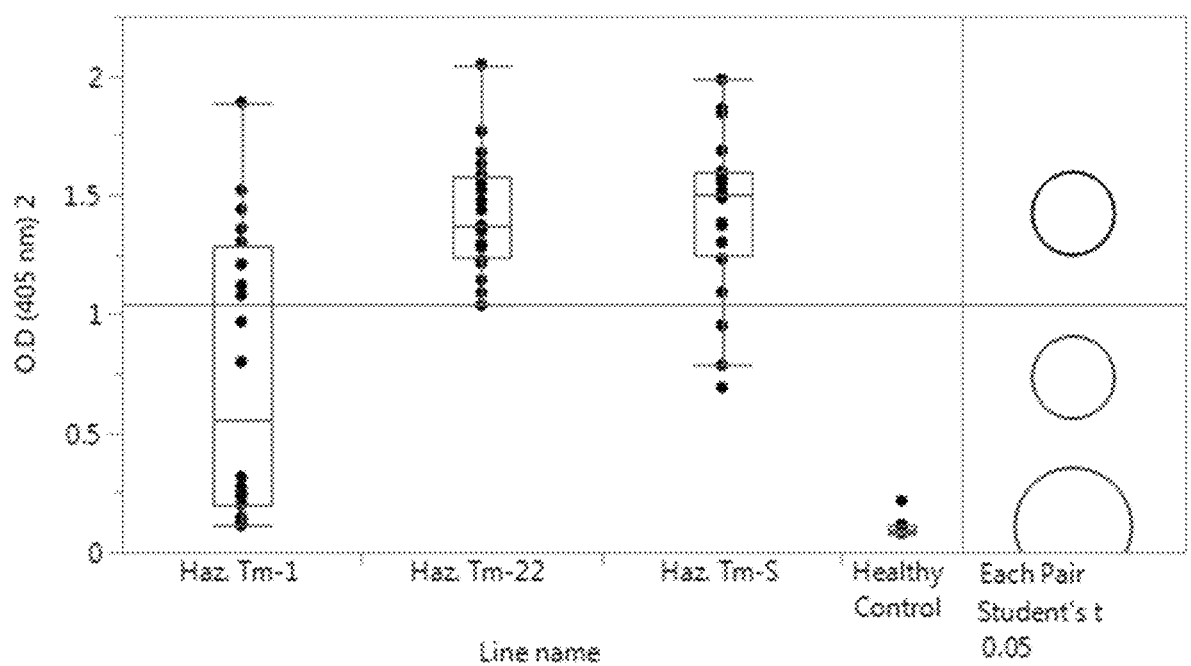

FIG. 3: Results of the ELISA tests conducted at around 110 DPI illustrating the presence or absence of TBRFV coat protein in leaves of tested plants.

This figure reports the optical density, as measured at 405 nm in the ELISA test, for 4 different plants.

Figure 4:
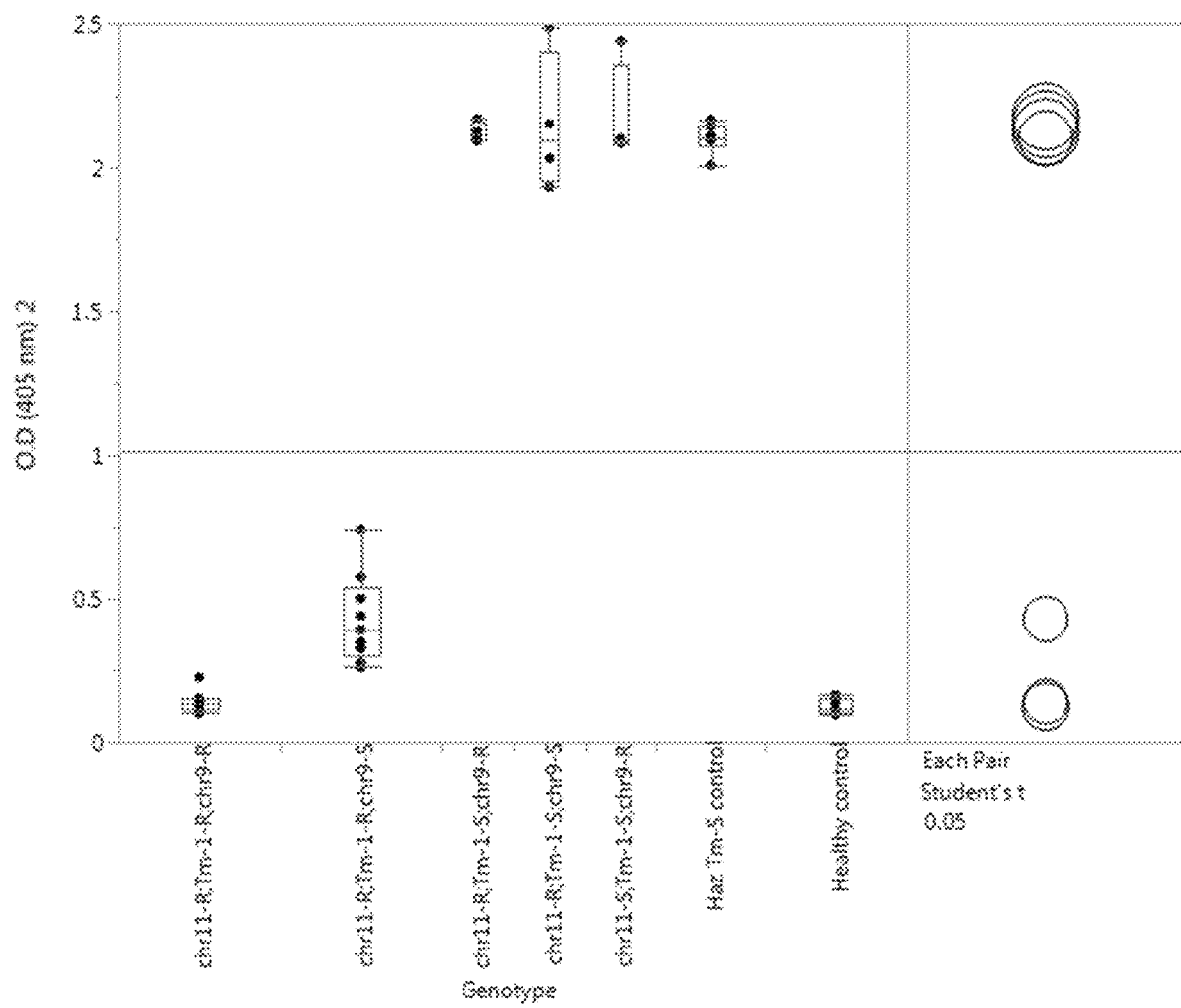

FIG. 4: Results of the ELISA tests conducted at 70 DPI on different QTLs combinations, illustrating the presence or absence of TBRFV coat protein in leaves of tested plants.

Figure 5:
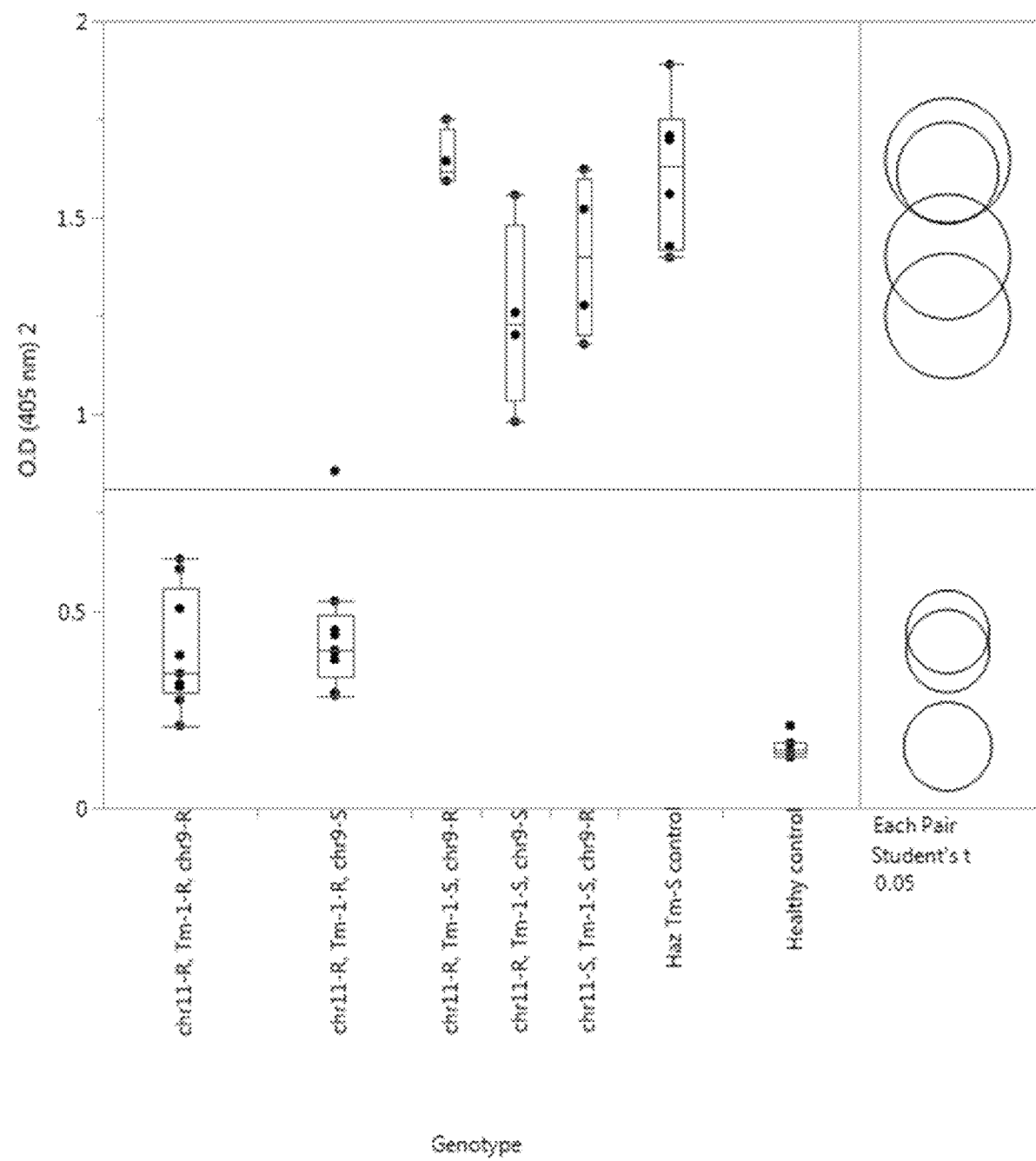

FIG. 5: Results of the ELISA tests conducted at 91 DPI on different QTLs combinations, illustrating the presence or absence of TBRFV coat protein in leaves of tested plants.

EXAMPLES

Example A: Identification of Resistance

The inventors have screened their tomato breeding genetic material in a naturally infected greenhouse in the Southern part of Israel, in the Bsor region, which is the major tomato crop production area in Israel. About 443 different tomatoes were screened. Each tomato was planted in two repeats, 10 plant per repeat in different locations in the greenhouse.

Each row in the greenhouse contained 120 plants. At each row, a susceptible line control of 10 plants was planted. In order to spread the controls in the different places in the greenhouse, the controls were positioned in diagonal along the different rows in the greenhouse.

In this screening, a few tomatoes showed no foliar TBRFV symptoms and very little fruit symptoms. Out of these, two symptomless tomatoes and two susceptible tomatoes were chosen for the next stage.

The results of these experiments are shown in table. A. The 2 susceptible tomatoes that have been chosen are representative of the 441 susceptible tomatoes in the sense that they are considered susceptible to the Tomato Brown Rugose fruit virus.

Hazera no. 1 (or HAZ1) is an indeterminate tomato of the loose type with regular, round and dark red fruits of about 170 gr. The plant has a dark green foliage and is resistant to *Verticillium* dahlia, *Meloidogyne incognita*, Tomato yellow leaf curl virus and *Stemphylium solani*.

Hazera no. 2 (or HAZ2) is an indeterminate tomato of the beef type with regular and intermediate flat, dark intense red fruits of about 280 gr. The plant is resistant to *Verticillium* dahlia, *Fusarium oxysporum* f.sp. *lycopersici* 1,2, Tomato mosaic virus, *Fulvia fulva*, *Meloidogyne incognita*, Tomato spotted wilt virus.

Hazera no. 3 (or HAZ3) is an indeterminate tomato of the beef type with intermediate flat red fruits of about 270 gr. The plant is resistant to Tomato spotted wilt virus, *Verticillium* dahlia *Fusarium oxysporum* f.sp. *lycopersici* 1,2 and *Stemphylium solani*.

Hazera no. 4 (or HAZ4) is an indeterminate tomato of the minibeef type with round red fruits of about 180 gr. The plant is resistant to Tobacco mosaic virus, Tomato yellow leaf curl virus, *Cladosporium fulvum* (C F9) *Verticillium* dahlia and *Fusarium oxysporum* f.sp. *lycopersici* 1,2.

TABLE A plants tested for resistance to TBRFV:

| Tomato | Total number of plants | Nb of plants without TBRFV foliar and fruit symptoms | Nb of plants with significant TBRFV foliar and fruit symptoms | Conclusion |
|---|---|---|---|---|
| Hazera no. 1 | 20 | 20 | 0 | Tolerant/Resistant |
| Hazera no. 2 | 20 | 0 | 20 | Susceptible |
| Hazera no. 3 | 20 | 20 | 0 | Tolerant/Resistant |
| Hazera no. 4 | 20 | 0 | 20 | Susceptible |

Example B: Confirmation of Resistance

In order to better understand the genetics underlying the tolerance/resistance phenotype as well as to validate the leads identified during the first screening, the present inventors have made a second screening under similar conditions as the ones of the first screening: each row in the greenhouses under natural infection contained 120 plants and at each row, a susceptible control (10 plants) was planted. In order to spread the controls in the different places in the greenhouse, the controls were positioned in diagonal along the different rows in the greenhouse.

In addition to the resistant tomatoes identified during the first screening, their F1 obtained from the cross of a resistant plant with a susceptible line were also included in the trial, as well as their F2s:

Table B shows the result of the second screening regarding the foliar evaluation: plants were considered as susceptible as soon as they had some mosaic and distortions in the apex of the shoots. Tolerant/Resistant plants have no symptoms in the apex of the shoots.

TABLE B

Foliar evaluation of second screening

| Tomato | Total number of plants | Number of plants without TBRFV foliar symptoms | Number of plants with significant TBRFV foliar symptoms | Conclusion |
|---|---|---|---|---|
| Hazera no. 1 | 20 | 20 | 0 | Tolerant/Resistant |
| Hazera no. 2 | 20 | 0 | 20 | Susceptible |
| F1 Hazera no. 1 × Hazera no. 2 | 20 | 0 | 20 | Susceptible |
| F2 Hazera no. 1 × Hazera no. 2 | 247 | 60 | 187 | Segregating |
| Hazera no. 3 | 20 | 20 | 0 | Tolerant/Resistant |
| Hazera no. 4 | 20 | 0 | 20 | Susceptible |
| F1 Hazera no. 3 × Hazera no. 4 | 20 | 0 | 20 | Susceptible |
| F2 Hazera no. 3 × Hazera no. 4 | 248 | 63 | 185 | Segregating |

The phenotyping data of the F1 and F2 plants tend to demonstrate that the foliar tolerance and or resistance to the Tomato Brown Rugose fruit virus is controlled in a recessive manner by one single gene or QTL.

Table C shows the result of the second screening regarding the fruit evaluation: plants are scored on a 1 to 4 scale whereby plants with 1 to 3 scores will be considered as susceptible, having for the plants graded 1 severe symptom of typical fruit lesions and some fruit deformation, for the plants graded 2 moderate lesions in some of the fruits only and 3 light symptoms. Only plants having 3.5 and 4, i.e. without symptoms on the fruits would be considered as resistant.

TABLE C

Fruit evaluation of second screening

| Line | Total number of plants | Number of plants With a fruit rating of symptoms | | | | | | Conclusion |
|---|---|---|---|---|---|---|---|---|
| | | 1 | 1.5 | 2 | 2.5 | 3 | 3.5 | |
| Hazera no. 1 | 20 | 0 | 0 | 0 | 0 | 0 | 20 | Tolerant |
| Hazera no. 2 | 20 | 20 | 0 | 0 | 0 | 0 | 0 | Susceptible |
| F2 Haz1 × Haz2 | 238 | 101 | 28 | 21 | 12 | 21 | 55 | Segregating |

The phenotyping data of the F2 plants tend to demonstrate that the fruit tolerance and/or resistance to the Tomato Brown Rugose fruit virus is controlled in a recessive manner by a few, one or two QTLs.

Example C: Association Analysis for Gene Mapping

The tomato plants Hazera no. 1 and Hazera no. 2 were used to build an F2 bi-parental mapping population. The tomato plant Hazera no. 1 showing a resistant phenotype (fruit and foliar) to Tomato Brown Rugose Fruit virus was crossed with the susceptible plant in order to create an F1 which was used later to generate an F2 segregating population. Additional bi-parental population used for validation (foliar QTL) based on Hazera no. 3 and Hazera no. 4 was developed in the same manner (see example E).

DNA Extraction: DNA was extracted from leaves ground using NucleoMag® Plant kit (Macherey-Nagel) according to the manufacturer's procedures. DNA purification was based on Magnetic-bead technology for the isolation of genomic DNA from plant tissue. DNA concentrations were quantified with a NanoDrop spectrophotometer.

The genotyping of the F2 population (based on Hazera no. 1 and Hazera no. 2) was done using a custom made Affymetrix Axium chip array containing approximatively 9500 SNPs for tomatoes (multiplex genotyping technology).

Tomatoes SNP markers were selected and discovered from different sources including public domain, LVS projects and collaborations. All SNPs were validated in pre-screen (previous experience on other technologies) and were selected according the following:
Polymorphic/Allele frequency
Representing world wide variation
SNP clusters removal
SNPs placed evenly according to physical map distance
Lower representation in heterochromatin (pericentromeric) regions—high LD Genotyping with the Affymetrix Axiom chip array was made using the standard protocol recommended by the manufacturer. The procedure includes the following steps: DNA amplification, fragmentation, precipitation, resuspension and hybridization preparation, hybridization to chip, wash, ligation, stain and scan. Two last steps are performed by Affymetrix's GeneTitan instrument. The analysis is performed by an automatic algorithm of clustering developed by Affymetrix.

A mixed linear model association was used independently for both fruit and foliar symptoms.

The mapping results revealed one candidate QTL associated with the foliar tolerance and/or resistance to Tomato Brown rugose Fruit virus located on chromosome 11 and two candidate QTLs associated with fruit tolerance and/or resistance to Tomato Brown rugose Fruit virus located on chromosomes 6 and chromosome 9.

Markers significantly linked with the various QTLs for foliar and/or fruit tolerance/resistance to Tomato Brown rugose Fruit virus and their position on the tomato genome are summarized in Table D. The sequence of the SNPs, including the flanking sequences are reported in table 4 and accompanying sequence listing part of the application.

Results showed that one QTL (QTL1 of the present invention) responsible for the fruit tolerance and or resistance to Tomato Brown rugose Fruit virus was located on chromosome 6, between position 33 932 438 and position 33 933 905, and that the second QTL (QTL2 of the present invention) responsible for the fruit tolerance and/or resistance to Tomato Brown rugose Fruit virus was located on chromosome 9, between position 4 800 680 and position 59 014 540, such physical positions on the genome being based on the version 2.40 of the tomato genome (Bombarely 2011). The region of chromosome 9 is a region of low recombination rate.

The region of chromosome 6 is a region prone to introgression and several genes of interest have already been mapped in this region, inter alia introgression of genes involved in salt tolerance from S. lycopersicoides, S. pennellii and S. pimpinellifolium (Li et al, Euphytica (2011) 178: 403), introgression of genes involved in powdery mildew resistance from S. habrochaites and S. neorickii (Seifi et al, Eur J Plant Pathol (2014) 138: 641) and introgression of genes involved in Pepino Mosaic Virus (WO2013/064641).

Results showed that the QTL responsible for the foliar tolerance and/or resistance to Tomato Brown rugose Fruit virus was located on chromosome 11, between position 9 548 029 and position 10 015 478, such physical position on the genome being based on the version 2.40 of the tomato genome (Bombarely 2011).

A further analysis was conducted with additional markers in order to better characterize the QTL on chromosome 11 responsible for the foliage resistance. The results are presented in table E and the sequences of the SNPs are reported in table 4.

These additional results allow to define, on the basis of the p-value and $R^2$ values, and on the variation of these values along chromosome 11, that the QTL responsible for the foliar tolerance to Tomato Brown rugose Fruit virus was broadly located on chromosome 11, between the SNPs TO-0122252 and TO-0162427, i.e. between position 8 090 264 and position 10 018 811, such physical positions on the genome being based on the version 2.40 of the tomato genome. The SNPs TO-0122252 and TO-0162427 flanking the broader definition of the QTL locus are mentioned by an asterisk (*) in table E. A narrower definition of the location of the QTL on chromosome 11 is the region defined by the SNPs TO-0142270 and TO-0162432. These flanking markers of the narrower definition of the locus are mentioned by (**) in table E. The SNPs having the more significant association with the QTL conferring foliar resistance/tolerance are mentioned by "+" in table E, namely TO-0181040, TO-0123057 and TO 60/125,528.

TABLE D list of SNPs, their position and the alleles found in susceptible plants ($1^{st}$ nucleotide mentioned: S allele) vs. the alleles of the markers linked to the tolerance/resistance ($2^{nd}$ nucleotide mentioned: T allele).

| SNP | R2 | Pvalue | Chromosome | Position SL2.40 | S/T allele |
|---|---|---|---|---|---|
| TO-0005197 | 0.33402601 | 5.61E−08 | 6 | 33932438 | C/T |
| TO-0145581 | 0.33402601 | 5.61E−08 | 6 | 33933905 | T/C |
| TO-0180955 | 0.33863743 | 1.68E−11 | 9 | 4800680 | A/G |

TABLE D-continued list of SNPs, their position and the alleles found in susceptible plants (1$^{st}$ nucleotide mentioned: S allele) vs. the alleles of the markers linked to the tolerance/resistance (2$^{nd}$ nucleotide mentioned: T allele).

| SNP | R2 | Pvalue | Chromosome | Position SL2.40 | S/T allele |
|---|---|---|---|---|---|
| TO-0196724 | 0.351965936 | 4.96E−12 | 9 | 5203457 | T/C |
| TO-0145125 | 0.347544015 | 6.03E−12 | 9 | 40025769 | A/G |
| TO-0196109 | 0.33402601 | 2.09E−11 | 9 | 59014540 | T/G |
| TO-0182276 |  |  | 11 | 9548029 | A/G |
| TO-0181040 | 0.848753 | 2.35E−50 | 11 | 9797143 | A/G |
| TO-0123057 | 0.8477487 | 5.33945E−51 | 11 | 9825111 | T/G |
| TO-0125528 | 0.8477487 | 5.33945E−51 | 11 | 9837711 | G/A |
| TO-0162432 | 0.7216998 | 8.88E−34 | 11 | 10015478 | T/C |

TABLE E additional flanking markers - association analysis mapping foliage resistance based on F2 population of HAZ1. The alleles found in susceptible plants (S allele) and the alleles of the markers linked to the tolerance/resistance (2$^{nd}$ nucleotide mentioned: T allele) are reported.

| SNP | R$^2$ | Pvalue | Position on chromosome 11 SL2.40 | Flanking markers | S/T allele |
|---|---|---|---|---|---|
| TO-0122252 | 0.7758002 | 1.16E−40 | 8090264 | * | A/T |
| TO-0144325 | 0.8101493 | 9.62E−45 | 8140310 |  |  |
| TO-0144322 | 0.8001583 | 1.10E−42 | 8163278 |  |  |
| TO-0144317 | 0.8051598 | 2.07E−44 | 8334467 |  |  |
| TO-0101684 | 0.8051598 | 2.07E−44 | 8345699 |  |  |
| TO.0197358 | 0.8051598 | 2.07E−44 | 8357644 |  |  |
| TO-0144313 | 0.8051598 | 2.07E−44 | 8410749 |  |  |
| TO-0144309 | 0.8249175 | 1.65E−46 | 8412924 |  |  |
| TO-0144308 | 0.8051598 | 2.07E−44 | 8414574 |  |  |
| TO-0144303 | 0.8051598 | 2.07E−44 | 8419932 |  |  |
| TO-0121816 | 0.797688 | 2.30E−42 | 8626324 |  |  |
| TO-0142268 | 0.7613548 | 5.39E−39 | 8631287 |  |  |
| TO-0142270 | 0.8064465 | 1.37E−44 | 8633469 | ** | C/T |
| TO-0142294 | 0.8474345 | 6.06e-51 | 8764030 |  |  |
| TO-0142299 | 0.8474345 | 6.06e-51 | 8891489 |  |  |
| TO-0142301 | 0.8474345 | 6.06E−51 | 8900707 |  |  |
| TO-0142302 | 0.8474345 | 6.06E−51 | 8902922 |  |  |
| TO-0142303 | 0.8474345 | 6.06E−51 | 8903092 |  |  |
| TO-0142305 | 0.8474345 | 6.06E−51 | 8963512 |  |  |
| TO.0142306 | 0.8474345 | 6.06E−51 | 9318832 |  |  |
| TO-0142307 | 0.8474345 | 6.06E−51 | 9318930 |  |  |
| TO-0162436 | 0.7855676 | 7.54E−41 | 9789608 |  |  |
| TO-0181040 | 0.848753 | 2.35E−50 | 9797143 | + | A/G |
| TO-0123057 | 0.8477487 | 5.34E−51 | 9825111 | + | T/G |
| TO-0125528 | 0.8477487 | 5.34E−51 | 9837711 | + | G/A |
| TO-0162432 | 0.7216998 | 8.88E−34 | 10015478 | ** | T/C |
| TO-0162427 | 0.7459438 | 2.53E−37 | 10018811 | * | C/T |

Example D: Further Marker Validation

One most associated marker to foliar tolerance to TBRF virus was defined at the edge of the QTL3 region to be the candidate marker close to the resistance gene. This SNP was designed to SNP monoplex KASPar technology: KASPar assay used for validation was preformed based on KASP method from KBioscience (LGC Group, Teddington, Middlesex, UK).

Primers for the KASP SNP assays were designed using LGC's primer picker software. Due to a SNP, two allele-specific forward primers and one common reverse primer per SNP assay were designed. KASP genotyping assays are based on competitive allele-specific PCR and enable bi-allelic scoring of SNPs at specific loci. To summarize, the SNP-specific KASP assay mix and the universal KASP Master mix were added to DNA samples, a thermal cycling reaction was then performed, followed by an end-point fluorescent read. Biallelic discrimination was achieved through the competitive binding of two allele-specific forward primers, each with a unique tail sequence that corresponded with two universal FRET (fluorescence resonant energy transfer) cassettes, one of which was labelled with FAM™ dye and the other of which was labelled with VIC™ dye (LGC, www.lgcgroup.com).

A volume of 3 μl of DNA was pipetted into black 384 well hard shell PCR plates and dried down at room temperature. When the genotyping was performed, the DNA was suspended by adding a 3 μl PCR mix, according to the manufacturer's protocol (KBioscience). Genotyping PCR results were analyzed using the software KlusterCaller (KBioscience). The marker used in this study is the TO-0182276 (SEQ ID NO:13).

HAZ3×HAZ4 F2 population (table B) was used for this marker validation. The F2 plants were genotyped using this marker and also phenotyped for foliar symptoms as described in example B. The association was 100% based on a data of 251 plants.

The summary data of phenotyping foliar symptoms and candidate marker genotyping is presented in table F:R marker means homozygous to resistance/tolerance allele, S marker means homozygous to susceptible allele, H marker means heterozygous comprising of the two alleles:

TABLE F

| | Number of plants | Number of plants with foliar TBRFV tolerance or resistance symptoms | Number of plants with foliar TBRFV susceptibility symptoms |
|---|---|---|---|
| R marker | 67 | 67 | 0 |
| S marker | 62 | 0 | 62 |
| H marker | 122 | 0 | 122 |

Example E: Association Analysis for Gene Mapping

The tomato plants Hazera no. 3 and Hazera no. 4 were used to build an F2 bi-parental mapping population. The tomato plant Hazera no. 3 showing a foliar resistance phenotype to Tomato Brown Rugose Fruit virus was crossed with the susceptible plant Hazera no. 4 in order to create an F1 which was used later to generate an F2 segregating population.

Crosses, phenotyping and associations were performed as described in example C, with HAZ1 and HAZ2.

The QTL for foliar resistance and the most significant associated markers were identified on chromosome 11, as detailed in table G.

As in example C, the broader definition of the locus comprising the QTL is defined by flanking markers with an asterisk in table G, namely SNPs TO-012252 and TO0162427. These SNPs are the same as those flanking the broader definition of the QTL position as deduced from the results obtained with the other tolerance source, namely HAZ1. This point strongly corroborates the conclusion that the QTL for foliar tolerance is the same for HAZ1 and HAZ3.

HAZ1 corresponds to the seeds HAZTBRFVRES1 deposited at the NICMB under the accession number 42758.

A narrower definition of the locus of the QTL, as deduced from the results on HAZ3 population is defined by the flanking makers TO-0144317 and TO-0125528 on chromosome 11 (markers ** in table G). The markers with the most significant association to TBRFV foliar tolerance/resistance are the markers mentioned with (+), namely TO-0142303, TO-0142306 and TO60142294.

TABLE G list of additional SNPs, their position and the alleles found in susceptible plants (1$^{st}$ nucleotide mentioned: S allele) vs. the alleles of the markers linked to the tolerance/resistance (2$^{nd}$ nucleotide mentioned: T allele)

| SNP | $R^2$ | Pvalue | Position chromosome 11 SL2.40 | Flanking markers | S/T allele |
|---|---|---|---|---|---|
| TO-0122252 | 0.81927235 | 1.55E-60 | 8090264 | * | A/T |
| TO-0144317 | 0.854230073 | 6.90E-69 | 8334467 | ** | T/C |
| TO-0142303 | 0.884698061 | 3.46E-77 | 8903092 | + | C/A |
| TO-0142305 | 0.884698061 | 3.468-77 | 8963512 | | |
| TO-0142306 | 0.884698061 | 3.46E-77 | 9318832 | + | G/A |
| TO-0142307 | 0.884698061 | 3.46E-77 | 9318930 | | |
| TO-0142294 | 0.884698061 | 3.46E-77 | 8764030 | + | A/G |
| TO-0142299 | 0.884698061 | 3.468-77 | 8891489 | | |
| TO-0142301 | 0.884698061 | 3.46E-77 | 8900707 | | |
| TO.0142302 | 0.884698061 | 3.46E-77 | 8902922 | | |
| TO-0144308 | 0.854199247 | 7.02E-69 | 8414574 | | |
| TO-0144303 | 0.854199247 | 7.02E-69 | 8419932 | | |
| TO-0142268 | 0.854144413 | 7.24E-89 | 8631287 | | |
| TO-0142270 | 0.854144413 | 7.24E-69 | 8633469 | | |
| TO-0121816 | 0.854144413 | 7.24E-69 | 8626324 | | |
| TO-0144313 | 0.853890923 | 2.18E-68 | 8410749 | | |
| TO-0181040 | 0.851931696 | 2.47E-68 | 9797143 | | |
| TO-0123057 | 0.851931696 | 2.47E-68 | 9825111 | | |
| TO-0125528 | 0.851931696 | 2.47E-68 | 9837711 | ** | G/A |
| TO-0144309 | 0.853578274 | 6.78E-68 | 8412924 | | |
| TO-0162436 | 0.851618235 | 7.62E-68 | 9789608 | | |
| TO-0197358 | 0.848638959 | 9.808-67 | 8357644 | | |
| TO-0101684 | 0.831991299 | 7.32E-64 | 8345699 | | |
| TO-0144325 | 0.821665121 | 9.468-62 | 8140310 | | |
| TO-0144322 | 0.822371998 | 1.62E-61 | 8163278 | | |
| TO-0162427 | 0.789778057 | 6.28E-56 | 10018811 | * | C/T |

Taken together, these results confirm the presence of a QTL conferring foliar tolerance, broadly located within the chromosomal region delimited by TO-012252 and TO0162427 and more precisely by TO-0144317 and TO-0125528.

In view of the results of example C, these results thus demonstrate that the location of this QTL can advantageously been defined as between TO-0142270 and TO-0125528.

Example 1: Material and Methods

Lines Description:
Line Haz-Tm1:

This line is a commercial indeterminate tomato of loose type with regular round and red fruits of about 120 g. The plant has light green foliage and is resistant to TMV race 0.

Test resistance: Line Haz-Tm1 was tested in 2 repeats of 10 plants each (total of 20 plants) for TBRFV resistance. The susceptible controls used were as follow (table 2):

TABLE 2

| Susceptible control name | Rep. | No. of plants | Foliar symptoms | Fruit symptoms |
|---|---|---|---|---|
| HA-29628 | 1 | 10 | Severe | Light |
| HA-29628 | 2 | 10 | Severe | Light |
| HA-29406 | 1 | 10 | Severe | Severe |
| HA-29406 | 2 | 10 | Severe | Severe |

"Rep" is the number of the repeat
"No. of plants" is the number of plants in the repeat.

Line NB2: Used to Make the Population

This line is an indeterminate tomato of loose type with globe and intense red fruits of about 160 gr. The plant has dark green foliage and is resistant to Stemphylium, Verticillium, Nematode, Fol race 1 race 2, TMV race 2.

Symptoms:

The symptoms of TBRFV infection are as follows:

Mild foliar symptoms: usually mosaic which is not severe, without significant distortion of the leaflets shape.

Severe foliar symptoms: leaflets are distorted, in many cases there is also "shoestrings" symptoms, almost always mosaic is severe.

Mild fruit symptoms: some yellow lesions (sometimes looks like "blotchy" symptoms), but no misshapen, distorted fruits.

Severe fruit symptoms: typical misshapen fruits, sometimes also "chocolate spots".

TBRFV symptoms Scoring: 4 scoring values, as described in WO2018/219941, with 4 corresponding to the absence of symptoms and 1 corresponding to severe symptoms.

ELISA Protocol:

Each sample containing 1-2 tomato leaves is crushed with homogenizer. 3 ml buffer SEB (Sample Extraction Buffer) were added and the sample is homogenized with bag mixer for 30 seconds.

The ToMV prime ELISA protocol of PrimeDiagnostics was then followed; this diagnostic test was chosen as it allows the detection of ToBRFV infection, although designed for ToMV infection.

Student's t-Test

The t-test is used to determine if the means of two sets of data are significantly different from each other.

In the comparison circles graph (see Figures), the position of the circles corresponds to the means of the various groups. The distance between the circles' centers represents the actual difference.

The outside angle of intersection of the comparison circles is informative about whether the group means are significantly different.

Circles for means that are significantly different either do not intersect, or intersect slightly, so that the outside angle of intersection is less than 90 degrees.

Markers:

The SNP markers suitable for detection of tolerance QTLs are disclosed below.

Table 3: list of SNPs, their position and the alleles found in susceptible plants (1$^{st}$ nucleotide mentioned: S allele) vs. the alleles of the markers linked to the tolerance (2$^{nd}$ nucleotide mentioned: T allele). Table 4: sequences of the SNPs.

TABLE 3

| SNP | Chromosome | Position SL2.40 | S/T allele |
| --- | --- | --- | --- |
| TO-0005197 | 6 | 33932438 | C/T |
| TO-0145581 | 6 | 33933905 | T/C |
| TO-0180955 | 9 | 4800680 | A/G |
| TO-0196724 | 9 | 5203457 | T/C |
| TO-0145125 | 9 | 40025769 | A/G |
| TO-0196109 | 9 | 59014540 | T/G |
| TO-0122252 | 11 | 8090264 | A/T |
| TO-0144317 | 11 | 8334467 | T/C |
| TO-0142270 | 11 | 8633469 | C/T |
| TO-0142294 | 11 | 8764030 | A/G |
| TO-0142303 | 11 | 8903092 | C/A |
| TO-0142306 | 11 | 9318832 | G/A |
| TO-0182276 | 11 | 9548029 | A/G |
| TO-0181040 | 11 | 9797143 | A/G |
| TO-0123057 | 11 | 9825111 | T/G |
| TO-0125528 | 11 | 9837711 | G/A |
| TO-0162432 | 11 | 10015478 | T/C |
| TO-0162427 | 11 | 10018811 | C/T |

TABLE 4

Sequences of the SNPs linked to the tolerance QTLs

| | SEQ ID | Sequence of the SNPs: the allele associated with the Tomato Brown rugose Fruit virus tolerance is mentioned second in the bracket |
| --- | --- | --- |
| TO-0005197 | 1 | GTCGGACCAAGAAACCATATTTGGTAACGGGTTCGAGTTGCTGCCTGAAC CTTTTAGCCC[C/T]TTGCAATATTTGTGAAGTGATATTCCTTTGTGTTATTAA TAATTTTTCGTTTTGAGTTTT |
| TO-0145581 | 2 | TTCAGAGAGCAACACTCCTGCAAGACCAACTCGGAGTAATTCAGTAACT CGACCTTCCAT[T/C]TCTAGCTCTCAGTATAGTACTTACTCAAATAAATCA GGCTCTATTCTAAACACAAGCTCT |
| TO-0180955 | 3 | TTCCGAAATGAGGACGATCCATCAGCTTCTTCAGCTGAGAGCCCCTGG TC[A/G]ACATACCAGAATTCTGTTTTTCTAAAACTGTCCAAAATCTCCTGT AAAGA |
| TO-0196724 | 4 | GATTTGAATGCCTTGCCACACGCCAGAGGATGACGA[T/C]GAGATTTTT GGACAACAATTAGAAGATGAACCACA |
| TO-0145125 | 5 | AGAGAATGATATCACTGCCTTAGTTTCTCAATTAAAAGTTGTGCAAAA ACAAAACACACA[A/G]CTAGATGAAGAAAACAGAGCATTCGCCTCAA AGCTTCAGACAAAAGAAGTTGAGAACAAC |
| TO-0196109 | 6 | TACAATACCTTCTGGCATCCCTTTCCGCAAAACGA[T/G]AGATCTTTAG TATCAAAACCGAGAGCACTGTCACC |
| TO-0122252 | 7 | ATGGCAATAGTGAACTGCAGATACAACTGAAATTGCAGAACACCCTTAAA [A/T]ATAGAATCAATAGAAAGTTGCAACAATATTTGAATGATGAAGCAACAAAG |
| TO-0144317 | 8 | AGCCATTGTGATTGTGTCTGTTGTACATTACCAAAATTCTCTAGAGAAAG [T/C]GATACACATGCCAGCCCTATCGATATAAAGCAACGCAAGGTGGATTCTGC |
| TO-0142270 | 9 | AACACCAGGTAGAGAGCACAGCGAAACAATGGCCTCAGGAAGATCTACTT[C/T] GCGAAGTGCAGCAAGCCACTCCATACCTCCACCAGGCTTTGATTTCAGTG |
| TO-0142294 | 10 | TCAACTGCAACTTTAACAGCTGATTCAACTTCTTCTTCTTTCGAAACATC [A/G]CATTGAATGTAACGACCTCCAATAGATTCAGCTAAACTTGTACCTACTTC |
| TO-0142303 | 11 | GAGGAGCTATCAACTTCATAGTCAGATTCAGAAAATGATTCAGATGAGGA [C/A]GTGGCTGATTCTTCTTGTTTTCTTTTCTTCCTTCTGCTCGAACTCTCTCC |

TABLE 4-continued

Sequences of the SNPs linked to the tolerance QTLs

| | SEQ ID | Sequence of the SNPs: the allele associated with the Tomato Brown rugose Fruit virus tolerance is mentioned second in the bracket |
|---|---|---|
| TO-0142306 | 12 | CAGAAATAATAGAAAATCAGAAAGAAAAATCAGCTTTCTAAATGGAAAAG[G/A]CGATGGCACTATGTTTGAAGTTTTAAGCAACTTTTCTGAAGTCCCAAAAG |
| TO-0182276 | 13 | CTCCTATTGAACATCCTGAAAACTTGTGTCTACATCATGAGAAGATGCAGGCCAATTC[A/G]CTCAGTACATGGAATGCACGAGCATGTTAGGGGAATTCTAACGCAAAGCATAAGCTTGATACTTGAATAAAAGATGAAACATACTTACTTCTTCTCAAACT |
| TO-0181040 | 14 | CTCTTGGTGACAAACCACTGGCTCAATTTCTTCGCGAAGCTAAAGCTATC[A/G]CTGATGAGCTTGTCACGGCAGGCACACGTGTCTCCTGATGAATTCAATGC |
| TO-0123057 | 15 | CATTACTGTTGAGATATCTCATCGGCAACCCCTGGAGCTTGCCCACCCGC[T/G]TGTCCTCCAGGATCTGATTTCAGAAAGGATGAATAGTAACTGTGTTTCAG |
| TO-0125528 | 16 | CAAGAACCCAACGACTTCTTCTTCTTTGCTTATTGAAAAACTTGGTTTTGAAATGAAAGG[G/A]ATCGAGAAATTGGATACTCAGTGGTTCTCTACTACTAAACCTTCTCCTGATTTTAAGAAA |
| TO-0162432 | 17 | TGATCGACAATTCTTGTTGTTGTTGAAACTCTGCAAGTGAGAGAGGGATG[T/C]ATATAG AGAAAGGATATTGGTAAAGGACAATTCTAGAAGGGTCTAGGGAA |
| TO-0162427 | 18 | GCACCAGTTATAGTAATGTCCTGCTTCTTTCCTGTACCCTTATCAGTAGC[C/T]GTGACAGAAAGAATACCGTTGGTGTCAATGTCGAACTTCACTTCAATCTG |

For Tm-1, a marker was developed based on information of Ishibashi et al, 2007:

Four in-gene SNPs were defined, KASPar assays were developed and only one was found to be suitable.

Marker code: TO-0200838

Sequence of the SNP: the allele associated with the virus resistance is mentioned first (i.e. A) in the bracket:

(SEQ ID No: 21)
CAAAGCTCTT/GGAAACTTTCCTAAGTAT/AAGCTAATG[A/G]TGAACA

GAATCTTGCTGGAGTA/GATTGGCCTTGGGGGTAGTGGAGGAACA.

KASPar Marker primers:
Primer forward Fam:
(SEQ ID No: 22)
GAAGGTGACCAAGTTCATGCTCAATYACTCCAGCAAGATTCTGTTCAT Primer forward Vic:
(SEQ ID No: 23)
GAAGGTCGGAGTCAACGGATTACTCCAGCAAGATTCTGTTCAC Primer reverse common:
((SEQ ID No: 24)
CAAAGCTCTKGAAACTTTCCTAAGTA Example 2: Resistance Sources First Resistance Source The inventors have first identified a cultivated tomato (*Solanum lycopersicum*) line—line Haz-Tm1 as having high level of foliar resistance to TBRFV. This line was also known to contain the gene Tm-1.

According to the literature and known to the skilled breeder, the Tm-1 was initially introgressed from a wild tomato species *Solanum habrochaites* P1126445 into the cultivated tomato species *Solanum lycopersicum* view a view to imparting ToMV/TMV resistance. Resistance by this gene to ToMV was however broken within a year of its introduction to commercial tomato cultivars in 1960s. Therefore, this gene is rarely, if any, found in the currently commercial varieties and can no longer be considered as a resistance gene to ToMV or TMV.

A marker for Tm-1 gene (on chromosome 2) was developed based on the public gene sequence. Four SNPs were defined, KASPar assays were developed and only one was found to be suitable.

The inventors first found that line Haz-Tm1 was highly resistant to TBRFV, in two trials under artificial laboratory test.

The inventors then later also screened the line Haz-Tm1 for fruit resistance under field conditions in greenhouse trial (natural infection). The trial was transplanted in a 4 dunam (corresponding to 4,000 m$^2$) greenhouse. The results showed that line Haz-Tm1 exhibited mild symptoms of TBRFV on the fruits, mostly at the latest stages of the plant growth. It was concluded that line Haz-Tm1 probably has high resistance to foliar symptoms and mild and insufficient resistance to fruit symptoms.

Line Haz-Tm1 was then re-tested in tests, including ELISA test, which included:
(1) sowing in "54" trays,
(2) mechanical inoculation of young seedlings
(3) scoring—observation of Tobamoviruses symptoms
(4) Checking presence/absence of the virus with an Immunostrip kit (AGDIA) and with an ELISA test in three-point times
(5) plantlets planted in the greenhouse to full growing cycle.

Sowing in nursery trays on 9$^{th}$ October
Mechanical inoculation: on 31$^{st}$ October
Transplanting part of the trial in Brurim (greenhouses GH 3 and 4): 5$^{th}$ November
Transplanting part of the trial in Mivtahim greenhouse: 13$^{th}$ November 1st Scoring and sampling for ELISA test: 16th and 17th December
2nd Scoring and sampling for ELISA test: 14th January
3rd Scoring and sampling for ELISA test: 19th February.

The results of the 1st scoring, around 45 days post inoculation (DPI) are detailed in table 5. At this stage, there are no fruits, thus only the foliar resistance is assayed.

TABLE 5

1st scoring of foliar symptoms at 45 DPI

| No. | Line name | Location | Total no. of plants | Healthy (score 4) | mild symptoms (score 2 or 3) | Severe symptoms (score 1) | Remarks |
|---|---|---|---|---|---|---|---|
| 1 | Haz. Tm-S | GH.3 | 5 | | | 5 | Typical |
| | | GH.4 | 5 | | | 5 | "shoestrings" |
| | | Mivtahim | 10 | | | 10 | |
| 4 | Haz. Tm-1 | GH.3 | 5 | 5 | | | |
| | | GH.4 | 5 | 5 | | | |
| | | Mivtahim | 10 | 9 | | 1 | |
| 5 | Haz. Tm-22 | GH.3 | 5 | | | 5 | Typical severe |
| | | GH.4 | 5 | | | 5 | mosaic |
| | | Mivtahim | 10 | | | 10 | |

The results of the ELISA test are illustrated in FIG. 1.

2nd Scoring

The phenotypic scoring of the 2nd scoring gave similar results as obtained in the 1st scoring. The results of the ELISA test are illustrated in FIG. 2.

3rd Scoring

The results of the 3rd scoring, around 110 DPI are detailed in table 6. At this stage, there are fruits, thus foliar and fruit resistance are scored.

TABLE 6

3rd scoring of foliar symptoms at 110 DPI

| | | | | Foliar symptoms | | | Fruit symptoms | | |
|---|---|---|---|---|---|---|---|---|---|
| No. | Line name | Location | Total no. of plants | No symp. (score 4) | Mild symp. (score 2 or 3) | Severe symp. (score 1) | No symp. (score 4) | Mild symp. (score 2 or 3) | Severe symp. (score 1) |
| 1 | Haz. Tm-S | GH.3 | 5 | | 5 | | | 5 | |
| | | GH.4 | 5 | | 5 | | | 5 | |
| | | Mivtahim | 10 | | 10 | | | 10 | |
| 4 | Haz. Tm-1 | GH.3 | 5 | 5 | | | 5 | | |
| | | GH.4 | 5 | 5 | | | 5 | | |
| | | Mivtahim | 10 | | 10 | | 10 | | |
| 5 | Haz. Tm-22 | GH.3 | 5 | | 5 | | | | 5 |
| | | GH.4 | 5 | | 5 | | | | 5 |
| | | Mivtahim | 10 | | 10 | | | | 10 |

The results of the ELISA test are illustrated in FIG. 3.

The ELISA results suggest that line Haz. Tm-1 has a defense mechanism that delays the virus reproduction in the plant.

Second Resistance Source

WO2018219941 discloses tolerance QTL to TBRFV, essentially a foliar tolerance QTL, QTL3, on chromosome 11 and two fruit tolerance QTLs, QTL1 and 2, on chromosomes 6 and 9 respectively.

Example 3: Combining by Crossing the Two Sources

Population Creation:

A cross between line Haz-Tm1 and line-NB2 was done to produce F1 seeds, the F1 was later self pollinated to produce F2 seeds. F2 seeds were sown in trays and selection for homozygous to tolerance QTL3 (i.e. QTL on chromosome 11) was done using one representative marker such as TO-0142306; these plants were advanced to produce F3 seeds, which are referred in the examples as population 1 (see table 7).

Plant Genotyping and Selection:

F3 seeds (population 1) were sown in trays, around 500 plantlets were obtained. From each F3 plantlet a leaf disc was sampled for DNA extraction and DNA was used for molecular marker analysis.

For selection, two molecular markers were used, one for the TM-1 gene on chromosome 2 and the 10 second representative of the QTL on chromosome 9 (QTL2), QTL for chromosome 11 (tolerance QTL3) was already fixed in the F2 as homozygote resistant (see population creation).

Results:

Crosses were made between line Haz. Tm-1 and one breeding line NB2 that contains the QTLs on chromosome 11 and QTL on chromosome 9. F3 seeds were obtained as disclosed above.

F3 plants were preselected in the tray using molecular markers linked to the tolerance QTLs and Tm-1 gene and the selected plants were mechanically inoculated at young seedlings level, plantlets were planted in the greenhouse in Bsor and grown in greenhouse.

Molecular marker analysis included one marker per QTL. Tables 7 and 9 present different F3 plants from the population 1 containing different genotypes at the 3 loci (QTL2, QTL3 and Tm-1), the resistance based on phenotypic scoring and ELISA results of each plant. Controls are also indicated. The healthy controls were not infected.

Table 7 presents the results at 70 DPI and table 9 at 91 DPI.

Some of the foliar symptoms reported in the tables might have been increased due to the presence of pepinovirus in the greenhouse as well as severe temperature conditions. It is indeed well known that symptoms of tobamovirus infection are increased when temperature is increased. This means that the medium to severe symptoms observed in this assay, could, in milder conditions, be considered as mild symptoms only. This assay was indeed designed to be discriminative between resistant plants on one side and tolerant or susceptible plants on the other side, and not between resistant/tolerant plants and susceptible plants.

TABLE 7

ELISA results at 70 DPI, and symptoms scoring of F3 plants. R stands for Resistant homozygote genotype, i.e. marker allele which is linked to resistance (or tolerance for the tolerance QTLs), S stands for "susceptible homozygote genotype". O.D.1 and O.D.2 correspond to the results of two distinct assays. Chr11 QTL refers to tolerance QTL3; Chr9 QTL refers to tolerance QTL2.

| Code | Detail | Chr11 QTL | Tm-1 Gene | Chr9 QTL | O.D (405 nm) 1 | O.D (405 nm) 2 | ELISA result | foliar symptoms |
|---|---|---|---|---|---|---|---|---|
| Blank | ELISA control | | | | 0.093 | 0.095 | | |
| Positive control | ELISA control | | | | 1.475 | 2.196 | | |
| Negative control | ELISA control | | | | 0.096 | 0.110 | | |
| Cut-off (2*NegCntr) | Calculation | | | | 0.192 | 0.219 | | |
| H-1 | Healthy control | | | | 0.092 | 0.105 | negative | N.A. |
| H-2 | Healthy control | | | | 0.091 | 0.095 | negative | N.A. |
| H-3 | Healthy control | | | | 0.102 | 0.115 | negative | N.A. |
| H-4 | Healthy control | | | | 0.089 | 0.101 | negative | N.A. |
| H-5 | Healthy control | | | | 0.133 | 0.166 | negative | N.A |
| H-6 | Healthy control | | | | 0.128 | 0.156 | negative | N.A. |
| H-7 | Healthy control | | | | 0.099 | 0.116 | negative | N.A. |
| H-8 | Healthy control | | | | 0.116 | 0.141 | negative | N.A. |
| 6305 | population 1 | R | R | R | 0.172 | 0.227 | Slightly positive | no |
| 6328 | population 1 | R | R | R | 0.112 | 0.127 | negative | no |
| 6381 | population 1 | R | R | R | 0.088 | 0.100 | negative | no |
| 6415 | population 1 | R | R | R | 0.131 | 0.154 | negative | no |
| 6429 | population 1 | R | R | R | 0.093 | 0.105 | negative | no |
| 6450 | population 1 | R | R | R | 0.120 | 0.149 | negative | no |
| 6464 | population 1 | R | R | R | 0.116 | 0.143 | negative | no |
| 6470 | population 1 | R | R | R | 0.112 | 0.136 | negative | no |
| 6472 | population 1 | R | R | R | 0.111 | 0.134 | negative | no |
| 6317 | population 1 | R | R | S | 0.342 | 0.502 | slightly positive | no |
| 6338 | population 1 | R | R | S | 0.311 | 0.443 | slightly positive | no |
| 6339 | population 1 | R | R | S | 0.401 | 0.576 | slightly positive | no |
| 6344 | population 1 | R | R | S | 0.254 | 0.352 | slightly positive | no |
| 6368 | population 1 | R | R | S | 0.514 | 0.742 | slightly positive | no |
| 6373 | population 1 | R | R | S | 0.289 | 0.393 | slightly positive | no |
| 6386 | population 1 | R | R | S | 0.200 | 0.279 | slightly positive | no |
| 6414 | population 1 | R | R | S | 0.175 | 0.262 | slightly positive | no |
| 6432 | population 1 | R | R | S | 0.226 | 0.327 | slightly positive | no |
| 6314 | population 1 | R | S | S | 1.365 | 2.030 | positive | mild |
| 6321 | population 1 | R | S | S | 1.307 | 1.930 | positive | mild |
| 6324 | population 1 | R | S | S | 1.444 | 2.153 | positive | mild |
| 6327 | population 1 | R | S | S | 1.689 | 2.488 | positive | mild |
| 6300 | population 1 | R | S | R | 1.462 | 2.171 | positive | Medium-severe |
| 6333 | population 1 | R | S | R | 1.402 | 2.126 | positive | Medium-severe |
| 6378 | population 1 | R | S | R | 1.405 | 2.091 | positive | Medium-severe |
| 6380 | population 1 | R | S | R | 1.397 | 2.099 | positive | Medium-severe |
| 1409--1 | population 1 | S | S | R | 1.389 | 2.086 | positive | severe |
| 1409--2 | population 1 | S | S | R | 1.434 | 2.099 | positive | severe |
| 1409--3 | population 1 | S | S | R | 1.369 | 2.084 | positive | severe |
| 1409--4 | population 1 | S | S | R | 1.642 | 2.441 | positive | severe |
| Blank | ELISA control | | | | 0.148 | 0.185 | | |
| Positive control | ELISA control | | | | 1.504 | 2.228 | | |

TABLE 7-continued

ELISA results at 70 DPI, and symptoms scoring of F3 plants. R stands for Resistant homozygote genotype, i.e. marker allele which is linked to resistance (or tolerance for the tolerance QTLs), S stands for "susceptible homozygote genotype". O.D.1 and O.D.2 correspond to the results of two distinct assays. Chr11 QTL refers to tolerance QTL3; Chr9 QTL refers to tolerance QTL2.

| Code | Detail | Chr11 QTL | Tm-1 Gene | Chr9 QTL | O.D (405 nm) 1 | O.D (405 nm) 2 | ELISA result | foliar symptoms |
|---|---|---|---|---|---|---|---|---|
| Negative control | ELISA control | | | | 0.127 | 0.162 | | |
| Cut-off (2*NegCnrl) | Calculation | | | | 0.254 | 0.324 | | |
| Haz Tm-S-1 | Susceptible control | | | | 1.328 | 2.007 | positive | severe |
| Haz Tm-S-2 | Susceptible control | | | | 1.421 | 2.142 | positive | severe |
| Haz Tm-S-3 | Susceptible control | | | | 1.457 | 2.168 | positive | severe |
| Haz Tm-S-4 | Susceptible control | | | | 1.394 | 2.094 | positive | severe |
| Haz Tm-S-5 | Susceptible control | | | | 1.375 | 2.094 | positive | severe |
| Haz Tm-S-6 | Susceptible control | | | | 1.386 | 2.109 | positive | severe |

TABLE 8

ELISA means of the reads at 70 DPI for the different QTLs combination and controls:

| Genotype | No of Plants | Mean | Std Error | Lower 95% | Upper 95% |
|---|---|---|---|---|---|
| Haz Tm-S control | 6 | 2.10233 | 0.04735 | 2.0064 | 2.1983 |
| Healthy control | 8 | 0.12438 | 0.04101 | 0.0413 | 0.2075 |
| chr11-R; Tm-1-R; chr9-R | 9 | 0.14167 | 0.03866 | 0.0633 | 0.2200 |
| chr11-R; Tm-1-R; chr9-S | 9 | 0.43067 | 0.03866 | 0.3523 | 0.5090 |
| chr11-R; Tm-1-S; chr9-R | 4 | 2.12175 | 0.05799 | 2.0042 | 2.2393 |
| chr11-R; Tm-1-S; chr9-S | 4 | 2.15025 | 0.05799 | 2.0327 | 2.2678 |
| chr11-S; Tm-1-S; chr9-R | 4 | 2.17750 | 0.05799 | 2.0600 | 2.2950 |

FIG. 4 illustrates the results of the ELISA test for the different QTLs combinations and controls, at 70 DPI.

It can be deduced that the combination of the Tm-1 gene and at least one of the tolerance QTL gives rise to a large decrease in the detection level of ToBRFV virus coat protein in the plants, and that the combination of the Tm-1 gene with two tolerance QTLs gives a ToBRFV detection level as low as the level found in non-infected healthy plants (Chr1-R, Tm-1-R, Chr9-R).

TABLE 9

ELISA results at 91 DPI, and symptoms scoring of F3 plants. R stands for Resistant homozygote genotype, i.e. marker allele which is linked to resistance (or tolerance for the tolerance QTLs), S stands for "susceptible homozygote genotype". O.D.1 and O.D.2 correspond to the results of two distinct assays. Chr11 QTL refers to tolerant QTL3; Chr9 QTL refers to tolerant QTL2.

| Code | Detail | Chr11 QTL | Tm-1 Gene | Chr9 QTL | O.D (405 nm) 1 | O.D (405 nm) 2 | ELISA result | foliar symptoms | Fruit symptoms | Remarks |
|---|---|---|---|---|---|---|---|---|---|---|
| Blank | ELISA control | | | | 0.097 | 0.110 | | | | |
| Positive control | ELISA control | | | | 1.717 | 2.711 | | | | |
| Negative control | ELISA control | | | | 0.117 | 0.137 | | | | |
| Cut-off (2*NegCntr) | Calculation | | | | 0.232 | 0.271 | | | | |
| H-1 | Healthy control | | | | 0.128 | 0.165 | negative | na | na | Control for ELISA |
| H-2 | Healthy control | | | | 0.154 | 0.209 | negative | na | na | Control for ELISA |
| H-3 | Healthy control | | | | 0.111 | 0.139 | negative | na | na | Control for ELISA |
| H-4 | Healthy control | | | | 0.107 | 0.129 | negative | na | na | Control for ELISA |
| H-5 | Healthy control | | | | 0.118 | 0.146 | negative | na | na | Control for ELISA |
| H-6 | Healthy control | | | | 0.131 | 0.166 | negative | na | na | Control for ELISA |
| H-7 | Healthy control | | | | 0.119 | 0.147 | negative | na | na | Control for ELISA |
| H-8 | Healthy control | | | | 0.117 | 0.146 | negative | na | na | Control for ELISA |
| 6305 | population 1 | R | R | R | 0.385 | 0.608 | Slightly positive | no | no | No clear symptoms but has some blotchy |
| 6328 | population 1 | R | R | R | 0.327 | 0.507 | Slightly positive | no | no | No clear symptoms but has some blotchy |

TABLE 9-continued

ELISA results at 91 DPI, and symptoms scoring of F3 plants. R stands for Resistant homozygote genotype, i.e. marker allele which is linked to resistance (or tolerance for the tolerance QTLs), S stands for "susceptible homozygote genotype". O.D.1 and O.D.2 correspond to the results of two distinct assays. Chr11 QTL refers to tolerant QTL3; Chr9 QTL refers to tolerant QTL2.

| Code | Detail | Chr11 QTL | Tm-1 Gene | Chr9 QTL | O.D (405 nm) 1 | O.D (405 nm) 2 | ELISA result | foliar symptoms | Fruit symptoms | Remarks |
|---|---|---|---|---|---|---|---|---|---|---|
| 6381 | population 1 | R | R | R | 0.229 | 0.342 | Slightly positive | no | no | No clear symptoms but has some blotchy |
| 6415 | population 1 | R | R | R | 0.193 | 0.275 | Slightly positive | no | no | No clear symptoms but has some blotchy |
| 6429 | population 1 | R | R | R | 0.264 | 0.388 | Slightly positive | no | no | No clear symptoms but has some blotchy |
| 6450 | population 1 | R | R | R | 0.156 | 0.209 | Slightly positive | no | no | No clear symptoms but has some blotchy |
| 6464 | population 1 | R | R | R | 0.214 | 0.308 | Slightly positive | no | no | No clear symptoms but has some blotchy |
| 6470 | population 1 | R | R | R | 0.216 | 0.316 | Slightly positive | no | no | No clear symptoms but has some blotchy |
| 6472 | population 1 | R | R | R | 0.407 | 0.633 | Slightly positive | no | no | No clear symptoms but has some blotchy |
| 6317 | population 1 | R | R | S | 0.543 | 0.856 | Slightly positive | no | no | No clear symptoms but has some blotchy |
| 6338 | population 1 | R | R | S | 0.260 | 0.400 | Slightly positive | no | no | No clear symptoms but has some blotchy |
| 6339 | population 1 | R | R | S | 0.263 | 0.396 | Slightly positive | no | no | No clear symptoms but has some blotchy |
| 6344 | population 1 | R | R | S | 0.206 | 0.293 | Slightly positive | no | no | No clear symptoms but has some blotchy |
| 6368 | population 1 | R | R | S | 0.346 | 0.526 | Slightly positive | no | no | No clear symptoms but has some blotchy |
| 6373 | population 1 | R | R | S | 0.251 | 0.377 | Slightly positive | no | no | No clear symptoms but has some blotchy |
| 6386 | population 1 | R | R | S | 0.195 | 0.286 | Slightly positive | no | no | No clear symptoms but has some blotchy |
| 6414 | population 1 | R | R | S | 0.280 | 0.439 | Slightly positive | no | no | No clear symptoms but has some blotchy |
| 6432 | population 1 | R | R | S | 0.296 | 0.453 | Slightly positive | no | no | No clear symptoms but has some blotchy |
| 6314 | population 1 | R | S | S | 0.801 | 1.259 | positive | severe | Medium | Some distortion on fruit with pointed blossom end |
| 6321 | population 1 | R | S | S | 0.631 | 0.982 | positive | severe | Medium | Some distortion on fruit with pointed blossom end |
| 6324 | population 1 | R | S | S | 0.760 | 1.203 | positive | severe | Medium | Some distortion on fruit with pointed blossom end |
| 6327 | population 1 | R | S | S | 0.978 | 1.558 | positive | severe | Medium | Some distortion on fruit with pointed blossom end |
| 6300 | population 1 | R | S | R | 0.978 | 1.593 | positive | severe | Mild | No significant distortion, no pointed blossom end |
| 6333 | population 1 | R | S | R | na | na | na | na | na | Dead plant |
| 6378 | population 1 | R | S | R | 0.985 | 1.594 | positive | severe | Mild | No significant distortion, no pointed blossom end |
| 6380 | population 1 | R | S | R | 1.083 | 1.751 | positive | severe | Mild | No significant distortion, no pointed blossom end |
| 1409--1 | population 1 | S | S | R | 1.012 | 1.623 | positive | severe | No | |
| 1409--2 | population 1 | S | S | R | 0.803 | 1.278 | positive | severe | No | |
| 1409--3 | population 1 | S | S | R | 0.754 | 1.180 | positive | severe | No | |
| 1409--4 | population 1 | S | S | R | na | na | na | na | na | Dead plant |
| Blank | ELISA control | | | | 0.109 | 0.128 | | | | |
| Positive control | ELISA control | | | | 1.919 | 2.830 | | | | |
| Negative control | ELISA control | | | | 0.131 | 0.161 | | | | |
| Cut-off (2*NegCnrl) | Calculation | | | | 0.263 | 0.321 | | | | |
| Haz Tm-S-1 | Susceptible control | | | | 1.144 | 1.698 | positive | severe | | Mild-Med. Sym |
| Haz Tm-S-2 | Susceptible control | | | | 1.280 | 1.890 | positive | severe | | Mild-Med. Sym |
| Haz Tm-S-3 | Susceptible control | | | | 1.148 | 1.709 | positive | severe | | Mild-Med. Sym |
| Haz Tm-S-4 | Susceptible control | | | | 1.049 | 1.560 | positive | severe | | Mild-Med. Sym |

TABLE 9-continued

ELISA results at 91 DPI, and symptoms scoring of F3 plants. R stands for Resistant homozygote genotype, i.e. marker allele which is linked to resistance (or tolerance for the tolerance QTLs), S stands for "susceptible homozygote genotype". O.D.1 and O.D.2 correspond to the results of two distinct assays. Chr11 QTL refers to tolerant QTL3; Chr9 QTL refers to tolerant QTL2.

| Code | Detail | Chr11 QTL | Tm-1 Gene | Chr9 QTL | O.D (405 nm) 1 | O.D (405 nm) 2 | ELISA result | foliar symptoms | Fruit symptoms | Remarks |
|---|---|---|---|---|---|---|---|---|---|---|
| Haz Tm-S-5 | Susceptible control | | | | 0.929 | 1.399 | positive | severe | Mild-Med. Sym | |
| Haz Tm-S-6 | Susceptible control | | | | 0.953 | 1.428 | positive | severe | Mild-Med. Sym | |

TABLE 10

ELISA means of the reads for the different QTLs combination and controls (91DPI)

| Genotype | No of Plants | Mean | Std Error | Lower 95% | Upper 95% |
|---|---|---|---|---|---|
| Haz Tm-S control | 6 | 1.61400 | 0.06391 | 1.4845 | 1.7435 |
| Healthy control | 8 | 0.15588 | 0.05535 | 0.0437 | 0.2680 |
| chr11-R, Tm-1-R, chr9-R | 9 | 0.39844 | 0.05218 | 0.2927 | 0.5042 |
| chr11-R, Tm-1-R, chr9-S | 9 | 0.44733 | 0.05218 | 0.3416 | 0.5531 |
| chr11-R, Tm-1-S, chr9-R | 4 | 1.64550 | 0.07827 | 1.4869 | 1.8041 |
| chr11-R, Tm-1-S, chr9-S | 4 | 1.25050 | 0.07827 | 1.0919 | 1.4091 |
| chr11-S, Tm-1-S, chr9-R | 4 | 1.40075 | 0.07827 | 1.2422 | 1.5593 |

FIG. 5 illustrates the results of the ELISA test for the different QTLs combinations and controls, at 91 DPI.

Results presented in table 9 and table 10 confirm the resistance of the plants comprising Tm-1 and at least one tolerance QTL, and demonstrates that this resistance is still present 3 months after infection, thus protecting the plants from foliar and fruit damages.

Example 4: Genetic Modification of Tomato Seeds by Ethyl Methane Sulfonate (EMS)

Seeds of a tomato varieties are to be treated with EMS by submergence of approximately 2000 seeds per variety into an aerated solution of either 0.5% (w/v) or 0.7% EMS for 24 hours at room temperature.

Approximately 1500 treated seeds per variety per EMS dose are germinated and the resulting plants are grown, preferably in a greenhouse, for example, from May to September, to produce seeds.

Following maturation, M2 seeds are harvested and bulked in one pool per variety per treatment. The resulting pools of M2 seeds are used as starting material to identify the individual M2 seeds and the plants with a fruit and/or a foliar tolerance to Tomato Brown Rugose Fruit virus.

The invention claimed is:

1. A *Solanum lycopersicum* plant resistant to Tomato Brown Rugose Fruit virus (TBRFV) comprising in its genome the combination of:
   a) the Tm-1 resistance gene on chromosome 2, and
   b) at least one quantitative trait locus (QTL) chosen from QTL3 on chromosome 11, QTL1 on chromosome 6 and QTL2 on chromosome 9, that independently confer to the plant foliar and/or fruit tolerance to TBRFV, wherein said QTLs are present in the genome of a plant, seeds of which designated HAZTBRFVRES1 have been deposited with NCIMB under accession number 42758,
   wherein said QTLs are to be found, for QTL1, on chromosome 6, within the chromosomal region delimited by TO-0005197 (SEQ ID NO:1) and TO-015581 (SEQ ID NO:2), for QTL2, on chromosome 9, within the chromosomal region delimited by TO-0180955 (SEQ ID NO:3) and TO-0196109 (SEQ ID NO:6) and for QTL3, on chromosome 11, within the chromosomal region delimited by TO-0122252 (SEQ ID NO:7) and TO-0162427 (SEQ ID NO:18).

2. A *S. lycopersicum* plant according to claim 1 comprising in its genome the combination of:
  a) the Tm-1 resistance gene on chromosome 2,
  b) said QTL3 on chromosome 11 homozygously, and
  c) said QTL2 on chromosome 9 heterozygously.

3. A *S. lycopersicum* plant according to claim 1 comprising in its genome the combination of the Tm-1 resistance gene and at least two QTLs chosen from QTL1, QTL2 and QTL3, wherein at least one of said QTLs is heterozygous.

4. A *S. lycopersicum* plant according to claim 1 comprising homozygously in its genome the combination of:
  a) the Tm-1 resistance gene on chromosome 2, and
  b) said QTL3 on chromosome 11.

5. A *S. lycopersicum* plant according to claim 1, wherein said plant delays, reduces or inhibits the replication or multiplication of the virus or reduces the virus titer in the plant.

6. A *S. lycopersicum* plant according to claim 1, wherein said TBRFV virus is the Israeli strain of TBRFV.

7. A *S. lycopersicum* plant according to claim 1, further comprising the Tm-2 resistance gene.

8. The *S. lycopersicum* plant according to claim 1, characterized by the presence in the genome of said *S. lycopersicum* plant of at least one of the following alleles:
  a) allele T of TO-0005197 and/or
  b) allele C of TO-0145581 for QTL1,
  c) allele G of TO-0180955 and/or
  d) allele C of TO-0196724 and/or
  e) allele G of TO-0145125 and/or
  f) allele G of TO-0196109 for QTL2,
  g) allele T of TO-0122252 and/or
  h) allele C of TO-0144317 and/or
  i) allele T of TO-0142270 and/or
  j) allele G of TO-0142294 and/or
  k) allele A of TO-0142303 and/or,
  l) allele A of TO-0142306 and/or
  m) allele G of TO-0182276 and/or
  n) allele G of TO-0181040 and/or
  o) allele G of TO-0123057 and/or
  p) allele A of TO-0125528 and/or
  q) allele C of TO-0162432 and/or
  r) allele T of TO-0162427 for QTL3,
  in combination with allele A of SNP marker TO-0200838 (SEQ ID No: 21).

9. The plant according to claim 1, wherein said plant is a progeny of an hybrid between a plant grown from the seeds of HAZTBRFVRES1 (NCIMB accession number 42758) and a *S. lycopersicum* plant bearing the Tm-1 gene.

10. A cell of a *S. lycopersicum* plant according to claim 1, comprising in its genome the combination of the Tm-1 gene and at least one QTL chosen from said QTL1 on chromosome 6, said QTL2 on chromosome 9 and said QTL3 on chromosome 11, wherein said combination confers the resistance to TBRF virus.

11. A plant part of a *S. lycopersicum* plant according to claim 1, in particular seeds, explants, reproductive material, scion, cutting, seed, fruit, root, rootstock, pollen, ovule, embryo, protoplast, leaf, anther, stem, petiole or flowers, wherein said plant part comprises cells according to claim 10.

12. A seed of a *S. lycopersicum* plant, which develops into a plant resistant to TBRFV according to claim 1.

13. A tissue culture of cells of the plant according to claim 1, wherein the cells are derived from embryos, protoplasts, meristematic cells, callus, pollen, leaves, anthers, stems, petioles, roots, root tips, seeds, flowers, cotyledons, and/or hypocotyls, and contain in their genome said QTL1 on chromosome 6, and/or said QTL2 on chromosome 9 and/or said QTL3 on chromosome 11 independently conferring fruit or foliar tolerance to TBRF virus, in combination with the Tm-1 gene.

14. A method for detecting *S. lycopersicum* plants according to claim 1, inhibiting, reducing or delaying the replication of the virus, comprising the steps of:
  a) detecting at least one of the following markers: allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and allele T of TO-0162427, and
  b) detecting the homozygous presence of the Tm-1 gene.

15. A method for selecting *S. lycopersicum* plants according to claim 1, inhibiting, reducing or delaying the replication of the virus, said method comprising the steps of:
  a) assaying tomato plants for the combination in its genome of
    i) the Tm-1 resistance gene on chromosome 2, and
    ii) at least one genetic marker genetically linked to a QTL chosen from QTL3 on chromosome 11, QTL1 on chromosome 6 and QTL2 on chromosome 9, independently conferring to the plant foliar and/or fruit tolerance to TBRFV, and
  b) selecting a plant comprising the Tm-1 gene and the genetic marker and the chosen QTL conferring foliar and/or fruit tolerance to TBRFV,
    wherein the chosen QTL and the genetic marker are to be found, for QTL1, on chromosome 6, within the chromosomal region delimited by TO-0005197 (SEQ ID NO:1) and TO-015581 (SEQ ID NO:2), for QTL2, on chromosome 9, within the chromosomal region delimited by TO-0180955 (SEQ ID NO:3) and TO-0196109 (SEQ ID NO:6) and for QTL3, on chromosome 11, within the chromosomal region delimited by TO-0122252 (SEQ ID NO:7) and TO-0162427 (SEQ ID NO:18).

16. A method for breeding *S. lycopersicum* plants having resistance to TBRFV, comprising the steps of crossing a plant grown from the deposited seeds NCIMB 42758 or progeny thereof bearing QTL1 and/or QTL2 and/of QTL3 conferring TBRFV tolerance, with a *S. lycopersicum* plant bearing the Tm-1 gene, wherein said QTL1, if present, is to be found on chromosome 6, within the chromosomal region delimited by TO-0005197 (SEQ ID NO:1) and TO-015581 (SEQ ID NO:2), said QTL2, if present, is to be found on chromosome 9, within the chromosomal region delimited by TO-0180955 (SEQ ID NO:3) and TO-0196109 (SEQ ID NO:6) and said QTL3, if present, is to be found on chromosome 11, within the chromosomal region delimited by TO-0122252 (SEQ ID NO:7) and TO-0162427 (SEQ ID NO:18).

17. A method according to claim 16, comprising the steps of:
  a) crossing a plant grown from the deposited seeds NCIMB 42758, or progeny thereof, bearing QTL1 and/or QTL2 and/or QTL3 conferring TBRFV tolerance, and a *S. lycopersicum* plant, preferably devoid of said QTL(s), and bearing the Tm-1 gene, b) selecting a plant in the progeny thus obtained, bearing one, two or three of the QTL1, QTL2 and QTL3 in combination with the Tm-1 gene;

c) self-pollinating one or several times the plant obtained at step b) and selecting in the progeny thus obtained a plant having resistance to TBRFV, wherein said resistance delays, reduces or inhibits the replication or multiplication of the virus.

18. A method according to claim 16, comprising the steps of:

a1) crossing a plant grown from the deposited seeds NCIMB 42758 or progeny thereof, bearing QTL1 and/or QTL2 and/or QTL3 conferring TBRFV tolerance, and a *S. lycopersicum* plant, preferably devoid of said QTL(s), and bearing the Tm-1 gene, thus generating F1 hybrids, a2) selfing the F1 hybrids to create F2 population, b) selecting individuals in the progeny thus obtained having resistance to TBRFV, wherein said resistance delays, reduces or inhibits the replication of the virus.

19. The method of claim 17, wherein SNPs markers are used in steps b) and/or c) for selecting plants bearing QTL1 and/or QTL2 and/or QTL3 conferring TBRFV tolerance and/or for selecting plants bearing the Tm-1 gene.

20. A *S. lycopersicum* plant obtained by the method according to claim 16, wherein said QTL1, if present, is to be found on chromosome 6, within the chromosomal region delimited by TO-0005197 (SEQ ID NO:1) and TO-015581 (SEQ ID NO:2), said QTL2, if present, is to be found on chromosome 9, within the chromosomal region delimited by TO-0180955 (SEQ ID NO:3) and TO-0196109 (SEQ ID NO:6) and said QTL3, if present, is to be found on chromosome 11, within the chromosomal region delimited by TO-0122252 (SEQ ID NO:7) and TO-0162427 (SEQ ID NO:18).

* * * * *

SEQUENCE LISTING

```
<160> NUMBER OF SEQ ID NOS: 26

<210> SEQ ID NO 1
<211> LENGTH: 121
<212> TYPE: DNA
<213> ORGANISM: Lycopersicon esculentum
<220> FEATURE:
<221> NAME/KEY: polymorphism
<222> LOCATION: (61)..(61)
<223> OTHER INFORMATION: susceptible = C; tolerant = T

<400> SEQUENCE: 1
gtcggaccaa gaaaccatat ttggtaacgg gttcgagttg ctgcctgaac cttttagccc      60
yttgcaatat ttgtgaagtg atattccttt gtgttattaa taattttcg ttttgagttt     120 t                                                                    121

<210> SEQ ID NO 2
<211> LENGTH: 121
<212> TYPE: DNA
<213> ORGANISM: Lycopersicon esculentum
```

```
<220> FEATURE:
<221> NAME/KEY: polymorphism
<222> LOCATION: (61)..(61)
<223> OTHER INFORMATION: susceptible = T; tolerant = C

<400> SEQUENCE: 2
ttcagagagc aacactcctg caagaccaac tcggagtaat tcagtaactc gaccttccat    60
ytctagctct cagtatagta cttactcaaa taaatcaggc tctattctaa acacaagctc   120
t                                                                   121

<210> SEQ ID NO 3
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = A; tolerant = G

<400> SEQUENCE: 3
ttccgaaatg aggacgatcc atcagcttct tcagctgaga gcccctggtc racataccag    60
aattctgttt ttctaaaact gtccaaaatc tcctgtaaag a                      101

<210> SEQ ID NO 4
<211> LENGTH: 71
<212> TYPE: DNA
<213> ORGANISM: Lycopersicon esculentum
<220> FEATURE:
<221> NAME/KEY: polymorphism
<222> LOCATION: (36)..(36)
<223> OTHER INFORMATION: susceptible = T; tolerant = C

<400> SEQUENCE: 4
gatttgaatg ccttgccaca gccagaggat gacgaygaga ttttggaca acaattagaa    60 gatgaaccac a                                                        71

<210> SEQ ID NO 5
<211> LENGTH: 121
<212> TYPE: DNA
<213> ORGANISM: Lycopersicon esculentum
<220> FEATURE:
<221> NAME/KEY: polymorphism
<222> LOCATION: (61)..(61)
<223> OTHER INFORMATION: susceptible = A; tolerant = G

<400> SEQUENCE: 5
agagaatgat atcactgcct tagtttctca attaaaagtt gtgcaaaaac aaaacacaca    60
rctagatgaa gaaaacagag cattcgcctc aaagcttcag acaaaagaag ttgagaacaa   120
c                                                                   121

<210> SEQ ID NO 6
<211> LENGTH: 71
<212> TYPE: DNA
<213> ORGANISM: Lycopersicon esculentum
<220> FEATURE:
<221> NAME/KEY: polymorphism
<222> LOCATION: (36)..(36)
<223> OTHER INFORMATION: susceptible = T; tolerant = G

<400> SEQUENCE: 6
tacaatacct tctggcatcc ctttccgcaa aacgakagat ctttagtatc aaaaccgaga    60
gcactgtcac c                                                        71
```

<210> SEQ ID NO 7
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = A; tolerant = T

<400> SEQUENCE: 7
atggcaatag tgaactgcag atacaactga aattgcagaa cacccttaaa watagaatca      60
atagaaagtt gcaacaatat ttgaatgatg aagcaacaaa g                         101

<210> SEQ ID NO 8
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = T; tolerant = C

<400> SEQUENCE: 8
agccattgtg attgtgtctg ttgtacatta ccaaaattct ctagagaaag ygatacacat      60
gccagcccta tcgatataaa gcaacgcaag gtggattctg c                         101

<210> SEQ ID NO 9
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = C; tolerant = T

<400> SEQUENCE: 9
aacaccaggt agagagcaca gcgaaacaat ggcctcagga agatctactt ygcgaagtgc      60
agcaagccac tccatacctc caccaggctt tgatttcagt g                         101

<210> SEQ ID NO 10
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = A; tolerant = G

<400> SEQUENCE: 10
tcaactgcaa ctttaacagc tgattcaact tcttcttctt tcgaaacatc rcattgaatg      60
taacgacctc caatagattc agctaaactt gtacctactt c                         101

<210> SEQ ID NO 11
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = C; tolerant = A

<400> SEQUENCE: 11
gaggagctat caacttcata gtcagattca gaaaatgatt cagatgagga mgtggctgat      60
tcttcttgtt ttcttttctt ccttctgctc gaactctctc c                         101

<210> SEQ ID NO 12
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = G; tolerant = A

<400> SEQUENCE: 12
cagaaataat agaaaatcag aagaaaaat cagctttcta aatggaaaag rcgatggcac     60
tatgtttgaa gttttaagca acttttctga agtcccaaaa g                       101

<210> SEQ ID NO 13
<211> LENGTH: 160
<212> TYPE: DNA
<213> ORGANISM: Lycopersicon esculentum
<220> FEATURE:
<221> NAME/KEY: polymorphism
<222> LOCATION: (59)..(59)
<223> OTHER INFORMATION: susceptible = A; tolerant = G

<400> SEQUENCE: 13
ctcctattga acatcctgaa aacttgtgtc tacatcatga gaagatgcag gccaattcrc     60
tcagtacatg gaatgcacga gcatgttagg ggaattctaa cgcaaagcat aagcttgata   120
cttgaataaa agatgaaaca tacttacttc ttctcaaact                         160

<210> SEQ ID NO 14
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = A; tolerant = G

<400> SEQUENCE: 14
ctcttggtga caaaccactg gctcaatttc ttcgcgaagc taaagctatc rctgatgagc     60
ttgtcacggc aggcacacgt gtctcctgat gaattcaatg c                       101

<210> SEQ ID NO 15
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = T; tolerant = G

<400> SEQUENCE: 15
cattactgtt gagatatctc atcggcaacc cctggagctt gcccacccgc ktgtcctcca     60
ggatctgatt tcagaaagga tgaatagtaa ctgtgtttca g                       101

<210> SEQ ID NO 16
<211> LENGTH: 121
<212> TYPE: DNA
<213> ORGANISM: Lycopersicon esculentum
<220> FEATURE:
<221> NAME/KEY: polymorphism
<222> LOCATION: (61)..(61)
<223> OTHER INFORMATION: susceptible = G; tolerant = A

<400> SEQUENCE: 16
caagaaccca acgacttctt cttctttgct tattgaaaaa cttggttttg aaatgaaagg     60
ratcgagaaa ttggatactc agtggttctc tactactaaa ccttctcctg attttaagaa    120
a                                                                    121

<210> SEQ ID NO 17
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = T; tolerant = C

<400> SEQUENCE: 17
tgatcgacaa ttcttgttgt tgttgaaact ctgcaagtga gagagggatg yatatagaga     60
aaggatattg gtaaaggaca attctagaag ggtctaggga a                        101

<210> SEQ ID NO 18
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = C; tolerant = T

<400> SEQUENCE: 18
gcaccagtta tagtaatgtc ctgcttcttt cctgtaccct tatcagtagc ygtgacagaa     60
agaataccgt tggtgtcaat gtcgaacttc acttcaatct g                        101

<210> SEQ ID NO 19
<211> LENGTH: 754
<212> TYPE: PRT
<213> ORGANISM: Lycopersicon esculentum

<400> SEQUENCE: 19

Met Ala Thr Ala Gln Ser Asn Ser Pro Arg Val Phe Cys Ile Gly Thr
1               5                   10                  15

Ala Asp Thr Lys Phe Asp Glu Leu Arg Phe Leu Ser Glu His Val Arg
            20                  25                  30

Ser Ser Leu Asn Ser Phe Ser Asn Lys Ser Ser Phe Lys Val Gly Val
        35                  40                  45

Thr Val Val Asp Val Ser Thr Ser Trp Lys Glu Thr Asn Ser Cys Ala
    50                  55                  60

Asp Phe Asp Phe Val Pro Ser Lys Asp Val Leu Ser Cys His Thr Leu
65                  70                  75                  80

Gly Glu Glu Thr Met Gly Thr Phe Ala Asp Ile Arg Gly Leu Ala Ile
                85                  90                  95

Ala Ile Met Ser Lys Ala Leu Glu Thr Phe Leu Ser Ile Ala Asn Asp
            100                 105                 110

Glu Gln Asn Leu Ala Gly Val Ile Gly Leu Gly Gly Ser Gly Gly Thr
        115                 120                 125

Ser Leu Leu Ser Ser Ala Phe Arg Ser Leu Pro Ile Gly Ile Pro Lys
    130                 135                 140

Val Ile Ile Ser Thr Val Ala Ser Gly Gln Thr Glu Ser Tyr Ile Gly
145                 150                 155                 160

Thr Ser Asp Leu Val Leu Phe Pro Ser Val Val Asp Ile Cys Gly Ile
                165                 170                 175

```
Asn Asn Val Ser Lys Val Val Leu Ser Asn Ala Gly Ala Ala Phe Ala
            180                 185                 190

Gly Met Val Ile Gly Arg Leu Glu Ser Ser Lys Glu His Ser Ile Thr
        195                 200                 205

Asn Gly Lys Phe Thr Val Gly Val Thr Met Phe Gly Val Thr Thr Pro
        210                 215                 220

Cys Val Asn Ala Val Lys Glu Arg Leu Val Lys Glu Gly Tyr Glu Thr
225                 230                 235                 240

Leu Val Phe His Ala Thr Gly Val Gly Gly Arg Ala Met Glu Asp Leu
            245                 250                 255

Val Arg Gly Gly Phe Ile Gln Gly Val Leu Asp Ile Thr Thr Thr Glu
        260                 265                 270

Val Ala Asp Tyr Val Val Gly Gly Val Met Ala Cys Asp Ser Ser Arg
    275                 280                 285

Phe Asp Ala Ile Leu Glu Lys Lys Ile Pro Leu Val Leu Ser Val Gly
290                 295                 300

Ala Leu Asp Met Val Asn Phe Gly Pro Lys Thr Thr Ile Pro Pro Glu
305                 310                 315                 320

Phe Gln Gln Arg Lys Ile His Glu His Asn Glu Gln Val Ser Leu Met
                325                 330                 335

Arg Thr Thr Val Gly Glu Asn Lys Lys Phe Ala Ala Phe Ile Ala Glu
            340                 345                 350

Lys Leu Asn Lys Ala Ser Ser Ser Val Cys Val Cys Leu Pro Glu Lys
        355                 360                 365

Gly Val Ser Ala Leu Asp Ala Pro Gly Lys Asp Phe Tyr Asp Pro Glu
    370                 375                 380

Ala Thr Ser Cys Leu Thr Arg Glu Leu Gln Met Leu Leu Glu Asn Asn
385                 390                 395                 400

Glu Arg Cys Gln Val Lys Val Leu Pro Tyr His Ile Asn Asp Ala Glu
                405                 410                 415

Phe Ala Asn Ala Leu Val Asp Ser Phe Leu Glu Ile Ser Pro Lys Ser
            420                 425                 430

Arg His Val Glu Cys Gln Pro Ala Glu Ser Lys Ser Ile Gln Asp Ile
        435                 440                 445

Gln Asn Asp Asn Ala Val Leu Glu Lys Tyr Pro Ser Cys Asn Gly Lys
    450                 455                 460

Asn Phe Ser Arg Leu Asn Asp Phe Pro Asn Ala Lys Pro Glu Thr Leu
465                 470                 475                 480

Gln Lys Arg Thr Val Ile Leu Gln Lys Leu Lys Asp Gln Ile Ser Lys
                485                 490                 495

Gly Lys Pro Ile Ile Gly Ala Gly Ala Gly Thr Gly Ile Ser Ala Lys
            500                 505                 510

Phe Glu Glu Ala Gly Gly Val Asp Leu Ile Val Leu Tyr Asn Ser Gly
        515                 520                 525

Arg Phe Arg Met Ala Gly Arg Gly Ser Leu Ala Gly Leu Leu Pro Phe
    530                 535                 540

Ala Asp Ala Asn Ala Ile Val Leu Glu Met Ala Asn Glu Val Leu Pro
545                 550                 555                 560

Val Val Lys Glu Val Ala Leu Ala Gly Val Cys Ala Thr Asp Pro
                565                 570                 575

Phe Arg Arg Met Asp Asn Phe Leu Lys Gln Leu Glu Ser Val Gly Phe
            580                 585                 590

Cys Gly Val Gln Asn Phe Pro Thr Val Gly Leu Phe Asp Gly Asn Phe
```

```
                    595                 600                 605
Arg Gln Asn Leu Glu Glu Thr Gly Met Gly Tyr Gly Leu Glu Val Glu
        610                 615                 620
Met Ile Ala Ala Ala His Arg Met Gly Leu Leu Thr Thr Pro Tyr Ala
625                 630                 635                 640
Phe Cys Pro Asp Glu Ala Val Ala Met Ala Glu Ala Gly Ala Asp Ile
                645                 650                 655
Ile Val Ala His Met Gly Leu Thr Thr Ser Gly Ser Ile Gly Ala Lys
            660                 665                 670
Thr Ala Val Ser Leu Glu Glu Ser Val Thr Cys Val Gln Ala Ile Ala
        675                 680                 685
Asp Ala Thr His Arg Ile Tyr Pro Asp Ala Ile Val Leu Cys His Gly
    690                 695                 700
Gly Pro Ile Ser Ser Pro Glu Glu Ala Ala Tyr Val Leu Lys Arg Thr
705                 710                 715                 720
Thr Gly Val His Gly Phe Tyr Gly Ala Ser Ser Met Glu Arg Leu Pro
                725                 730                 735
Val Glu Gln Ala Ile Thr Ala Thr Val Gln Gln Tyr Lys Ser Ile Ser
            740                 745                 750
Met Glu
```

<210> SEQ ID NO 20
<211> LENGTH: 2718
<212> TYPE: DNA
<213> ORGANISM: Lycopersicon esculentum

<400> SEQUENCE: 20

```
gactttttta tttatttaat attaaatatt aatattgctc catcggaata aaaataaaaa      60
taaaaatgga acctctccac ttgacggttg ttgccgcctc tctgtccaac cgttgccggt     120
gatctttcat cgtcgagatt ccagaagcta caactttct aatcttctca ccattctcac      180
actgagttac actctatcgt ccattttgaa atctcgattg taacacgaat tgtatcattt     240
tgtttgagga aaatggcaac tgcacagagt aattctcctc gagttttctg tatcggaaca     300
gctgatacaa aattcgacga gcttcgtttc ctctccgagc atgtgagatc cagtcttaac     360
agcttctcca ataaatcctc attcaaggta ggagtgacag ttgttgatgt ctcaaccagc     420
tggaaggaga caaatagttg tgctgatttt gattttgtac cgagtaagga tgtgctgtca     480
tgccatacac tagggaaga aactatgggc acgtttgcag atattagagg cctagctatt      540
gcaatcatga gcaaagctct tgaaactttc ctaagtatag ctaatgatga acagaatctt     600
gctggagtaa ttggccttgg gggtagtgga ggaacatctc tattgtcatc tgccttccga     660
tctcttccaa ttgggatccc aaaagttata atatctacag ttgccagtgg tcaaactgaa     720
tcttatattg gaacatcaga cttggtattg tttccttcag ttgtagatat ttgtgggatt     780
aacaatgtca gtaaggttgt tctatctaat gcgggtgcag catttgctgg aatggtgatc     840
gggaggcttg aaagttcaaa agagcatagc atcactaatg gaaagtttac agttggtgta     900
actatgtttg gggttacgac tccttgtgtt aatgctgtca agaaagatt agtgaaagaa      960
ggatatgaga ctttggtgtt ccatgccacg ggtgtcgggg cagggccat ggaggatctt     1020
gttagaggag gttttataca gggtgtgctg atattacga caactgaggt tgcagattac     1080
gtagttggag gagtaatggc atgtgatagt tcccgatttg atgcaatatt agagaagaaa    1140
attcctttgg ttctgagtgt gggagcactg gatatggtga attttggtcc taaaactacc    1200
```

```
atacctcctg agtttcaaca agaaagatc catgaacata atgagcaggt ttccctaatg   1260
cgtactacag taggtgaaaa taagaaattt gctgcattta tagcagaaaa gttgaacaag   1320
gcatcatcaa gtgtatgtgt ttgcttgcca gagaaaggcg tgtctgcatt ggatgcaccc   1380
gggaaagact tttatgatcc tgaggcaact agttgtctta cacgtgaact acagatgctt   1440
cttgaaaata tgaacgttg tcaggttaag gtcctcsectt accatatcaa tgatgcggag   1500
tttgcaaatg ctttagttga ttcattcttg gaaatctctc cgaaatctag acacgtagaa   1560
tgtcagccag ctgagtccaa atctatccaa gacattcaga atgataatgc tgttctagag   1620
aaatatccct catgcaacgg gaaaaacttt tctcgcctga atgactttcc aaatgcaaaa   1680
ccagaaactt tgcagaaaag aactgtgata ctgcagaaat tgaagatca aataagtaag   1740 ggcaagccta ttattggggc tggtgctggt acaggtattt ctgctaagtt tgaggaagct   1800
ggtggtgtag atttgattgt cttgtacaac tcagggcgct ttaggatggc aggaagggga   1860
tccttagctg gtctactgcc ctttgctgat gcaaatgcca ttgtacttga gatggccaac   1920
gaagtattgc ctgtggttaa ggaagtggca gttctggctg gagtttgtgc tactgatcct   1980
ttccgcagga tggacaactt cctgaagcag ttggaatccg ttggattctg tggggtgcaa   2040
aactttccaa ctgttggtct gtttgacggt aacttcagac aaaatttgga agagactgga   2100
atgggttatg gcttggaggt tgagatgatt gcagcagctc acaggatggg ccttttgaca   2160
accccatatg ctttctgccc agatgaagca gttgctatgg cagaagctgg tgccgacatc   2220
atagttgctc atatggggct tacaacatct ggttcaattg gtgcaaaaac agccgtctca   2280
ttggaggaaa gtgtaacttg cgttcaagct attgcagatg ctactcatag gatatatcct   2340
gatgcaattg tgctctgcca tggaggccct atatcttccc ctgaagaagc agcatatgta   2400
ctgaagagaa ccacaggagt tcatggattt tatggcgctt caagcatgga aagactacca   2460
gttgagcaag ctataactgc aactgtccag cagtacaagt ctatttctat ggagtgagat   2520
gcagtggatt ttggttcttt aaatgtccga acctatatgt atggtcttca cctctttctt   2580
tatgtatgat catgtccagg gctcctctgt actcatctag caacttgaaa cactacagca   2640
ctgctgctgc agtttttatc tgtccatatg atatcaattt caacaagtta tatcttttcg   2700
tcaaaaaaaa aaaaaaaa                                                 2718
```

<210> SEQ ID NO 21
<211> LENGTH: 88
<212> TYPE: DNA
<213> ORGANISM: Lycopersicon esculentum
<220> FEATURE:
<221> NAME/KEY: polymorphism
<222> LOCATION: (38)..(38)
<223> OTHER INFORMATION: susceptible = G; resistant = A

<400> SEQUENCE: 21

```
caaagctctt ggaaactttc ctaagtataa gctaatgrtg aacagaatct tgctggagta   60
gattggcctt gggggtagtg gaggaaca                                      88
```

<210> SEQ ID NO 22
<211> LENGTH: 48
<212> TYPE: DNA
<213> ORGANISM: Lycopersicon esculentum

<400> SEQUENCE: 22

```
gaaggtgacc aagttcatgc tcaatyactc cagcaagatt ctgttcat                48
```

```
<210> SEQ ID NO 23
<211> LENGTH: 43
<212> TYPE: DNA
<213> ORGANISM: Lycopersicon esculentum

<400> SEQUENCE: 23
gaaggtcgga gtcaacggat tactccagca agattctgtt cac                    43

<210> SEQ ID NO 24
<211> LENGTH: 26
<212> TYPE: DNA
<213> ORGANISM: Lycopersicon esculentum

<400> SEQUENCE: 24
caaagctctk gaaactttcc taagta                                       26

<210> SEQ ID NO 25
<211> LENGTH: 6393
<212> TYPE: DNA
<213> ORGANISM: Tomato Brown Rugose Fruit virus

<400> SEQUENCE: 25 gtattttgt tttacaacat ataccaacaa caacaaacaa caaacaacaa cattacaatt    60
actatttaca actacaatgg catacacaca gacagctacc acatccgctt tgctcgacac   120
tgtccgaggt aacaatacct tggtcaacga tcttgcgaag cggcgtcttt atgacacagc   180
ggtcgacgag ttcaacgctc gtgatcgcag gcccaaagta aattttttcca agtaataag   240 tgaggaacag acgcttattg ctactagggc atatccagaa ttccagataa ccttctataa   300
tacgcagaac gccgtgcatt cgcttgccgg tggactacga tccttagaac tggaatatct   360
aatgatgcag atcccgtacg atcactcac atatgatata ggtgggaatt ttgcatctca    420
tctgttcaaa ggacgggcat atgttcactg ctgtatgccc aatcttgatg tccgcgacat   480
aatgcggcac gaaggccaga agacagtat agaattatac ctttccaggc ttgagcgggg   540
caacaaagtt gtcccaaatt ccaaaagga agcttttgac agatacgctg aaacgccaga   600
cgaagttgtc tgtcacagta ccttccaaac gtgtacgcac cagcaggtgg aaaacacagg   660
cagggtgtat gctattgcat tgcacagtat atacgatata cctgctgatg aattcggagc   720 ggcacttta aggaaaaatg tccatgtttg ttacgccgcc ttccactttt ccgagaattt    780
acttctcgaa gattcacacg tcaaccttga cgaaatcaac gcgtgttttt cgcgtgatgg   840
agacaagctg acttttttctt tcgcatctga gagcacttta aattattgtc atagttattc   900
taatatttta aaatacgtgt gcaaaactta cttcccggca tctaatagag aggtctacat   960
gaaggagttt ttggtcacca gggttaacac ctggttttgt aagttttcta ggatagatac  1020 tttttttatta tacaagggg tagcccacaa aggtgtaaat agtgagcaat ttacagcgc   1080 aatggaagat gcatggcact acaaaagac tcttgcaatg tgtaacagcg agaggattct  1140
tcttgaagat tcctcatcgg tcaattactg gttcccaaaa atgagagata tggtcatagt  1200
tcctctattc gacatatctc tcgacaccag taaaaggacc cgcaaagaag tcttagtgtc  1260 aaaggattt gtattcacag ttttaaatca cattcgcact tatcaagcca aggcacttac   1320
atactccaat gttttatcct ttgtcgaatc aattcgttca agggtaatta tcaacggagt  1380
gactgccagg tctgagtggg atgttgacaa atctcttttg caatccttgt ccatgacatt  1440
tttcttgcat actaagcttg ccgttttaaa agacgaattg ttaatcagca gtttagttt    1500 ggggccaaaa tcagtaagcc agcatgtatg ggatgagatt tccctggctt ttggaaacgc  1560
```

```
atttccatcg atcaaggaga gactgctaaa tcggaaacta attaaagtgt cgggagacgc   1620
attagaaatc agggtgcctg atttatatgt gacttttcac gatagattag tgactgagta   1680
caaaacatcg gtggatatgc cagtgcttga tatcagaaag agaatggagg agactgaggt   1740
tatgtacaat gcattgtctg agctatctgt gctcaaggag tcggacaagt tcgacgttga   1800
tgttttttcc cggatgtgcc agactttgga ggtagaccca atgactgcag caaaggttat   1860
tgtggcagtg atgagcaacg agagcggact gactcttaca ttcgaacagc caactgaagc   1920
aaatgtcgca ttggcactta agattcaga aaaagcctct gagggtgcac tagtggttac   1980
ttctagagat gttgaagaac catccatgaa gggttcaatg gcaagaggag agttacaatt   2040
ggccggtctg tctggagacc aaccagagtc ttcctatact cggaacgagg aaatagagtc   2100
attagagcaa ttccacatgg caacggctag ttcgttaatt cggaaacaga tgagttcgat   2160
tgtgtacacg ggccccatta agttcagca atgaaaaac tttattgata gcctggtagc   2220
atcactctct gctgcggtgt cgaacctagt caagatccta aaggatacag ctgctataga   2280
tctcgaaacc cgtcagaagt ttggagtctt agatgttgcg accaaaagat ggttaattaa   2340
acctttagcc aagaatcacg catggggcgt tattgaaaca catgctagga agtaccacgt   2400
tgcacttttg gagtatgatg agcatggagt ggtaacttgc gacagttgga gaagggtggc   2460
cgtgagttct gagtcaatgg tttattctga tatggcaaag ctcagaacac tgaggagatt   2520
attaagagat ggtgagcctc atgtcagcag tgctaaagtc gtcctagttg acggtgtccc   2580
gggttgtgga aagacaaaag agattctctc gaaagtaaat tttgaggaag atctaatctt   2640
agtaccgggt aagcaggctg ctgaaatgat aaagaggcgt gctaatgcgt caggaataat   2700
tcaagccaca agagataatg ttcgtactgt tgattcattt ataatgaatt acggtaaagg   2760
aacacgctgt cagttcaaaa ggttatttat cgacgaaggt ctgatgttgc acactggttg   2820
tgtgaatttt cttgtttcta tgtctctgtg cgaaattgca tatgtttatg gagacacaca   2880
acaaattcca tacatcaaca gagtatccgg ttttccgtac cctgcacatt ttgcaaaaat   2940
agaggttgat gaggtggaaa ctcgcagaac tacgctgcgt tgtccagccg acattaccca   3000
ctatcttaac agaaggtacg aaggatatgt catgtgtaca tcgtcggtta aaaagtcagt   3060
ttctcaggaa atggtgagcg gggccgcaat gatcaatcct gtatctaagc cattgaatgg   3120
gaaagttttg actttcactc agtctgataa agaggcgctg ctttctcgag atatacggo   3180 cgtccataca gtacatgagg tacaaggtga gacatatgca gatgtgtcgt tggtcagatt   3240
gactccgaca cctgtatcta tcatcgcagg agatagtccg cacgttctcg tagctttgtc   3300
aaggcatacc caaacattga agtattacac cgtagtgatg gatcctcttg taagtataat   3360
tagggattta gaaaaactta gttcttactt gttagatatg tataaagtag atgcagggac   3420
ccaatagcaa ttacaggtag actccgtgtt taaaggttct aatctttttg ttgcagcacc   3480
aaagactgga gatatctcag atatgcaatt ttactatgat aagtgtctcc caggtaatag   3540
caccatgtta ataactatg atgctgttac catgaggttg actgacattt ctcttaatgt   3600
caaagattgc atattggatt tctctaagtc tgtggctgca ccgaaggatc cgatcaaacc   3660
actgattccg atggtacgaa cggcggcaga atgccacgc cagactggac tattggaaaa   3720
tttggtggcg atgatcaaaa gaaactttaa ttcaccggag ttatcaggaa taatcgacat   3780
tgagaatact gcatctttag tagtagataa attttttgat agttacttgc ttaaagaaaa   3840
aagaaaacca aataaaaatg tttctttatt ttgtagagag tctctcaata gatggttaga   3900
gaagcaggag caagtgacca ttggtcagct tgcagatttt gattttgtgg atcttcctgc   3960
```

-continued

```
cgttgatcag tacaggcata tgattaaagc gcaacctaag cagaagctgg atacatcaat    4020
tcaaagcgaa tatccggcct tgcagacgat tgtgtatcat tcgaaaaaga tcaacgcaat    4080
cttcggtcct ttgttcagtg agctcacaag gcaaatgctc gaaagcatag actcaagtaa    4140 gttttgttc tttacaagga agacgccagc tcaaattgag gatttcttcg gagatctcga    4200
tagccatgtc cctatggata tcttggagtt ggatatttcg aagtatgaca atctcagaa    4260 cgagttccac tgtgcagtag agtatgaaat atggagaaga cttggattag aagattttct    4320
gggagaagtt tggaaacaag gccacaggaa aactactctt aaagattaca cagctggtat    4380
taaaacgtgt ttatggtacc agagaaagag tggggacgtt acaacattca tcggtaatac    4440
ggtgattatt gctgcttgtt tagcttccat gttgcccatg gagaaaataa tcaaggtgc     4500 attttgcgga gatgacagtt tactatactt cccaaaaggt tgtgagtttc ctgacataca    4560
gcatacagcc aaccttatgt ggaatttcga ggctaagcta ttcagaaagc agtatggtta    4620
tttctgtgga aggtacgtga tacatcatga cagagggtgt attgtttatt atgacccttt    4680
gaagttgatt tctaaacttg gtgctaaaca catcaaggat tgggatcact tagaagagtt    4740
cagaagatcc ctttgtgatg ttgcaaattc gttgaacaac tgtgcgtatt acacgcagtt    4800
ggacgacgct gtgagtgagg tccataaaac cgcaccccg ggttcgtttg tatataaaag     4860
tttagttaaa tatctgtccg ataaggttct ttttagaagt ttgtttatag atggctcttg    4920
ttaagggtaa agtcaatatt aatgagttca tagacttgtc aaaatcagaa aaatttcttc    4980
cgtctatgtt cacacctgtt aagagtgtca tgatctccaa ggttgataag atattggttc    5040
atgaagatga atctttgtcc gaagtcaatt tactcaaagg tgtaaaactc attgatggtg    5100
gctatgtaca tcttgctggt cttgtggtga caggtgaatg gaatttgcca gataattgtc    5160
gtggtggtgt cagtgtctgt ttggtcgata agagaatgga gagagcggac gaggcaactc    5220
ttgcttcata ctataccgca gcggctaaga aaaggtttca gttcaaagtc gttccaaatt    5280
acaacatcac taccaaggac gcagaaaagg cagtttggca agtactagtt aatattagaa    5340
atgttaaaat tgctgcgggt tactgtccgc tgtcattaga atttgtgtca gtgtgtattg    5400
tttataaaaa tattataaaa ctcggtttga gagagaaaat tacgagcgtc acggatggag    5460
ggcccatgga actatcagaa gaagttgttg atgagttcat ggaagaagtc ccgatgtctg    5520
taaggcttgc aaaatttcgt tcgaagaccg gaaaaaagtt tagtagtaaa agtgagaata    5580
atagtggtaa aataggccg aaaccagaca aaaaccaaag gaaggaaaag ggtttaaaag     5640
ttagggttga gaaggataat ttaattgata atgaattgga gacttacgtc gccgattcag    5700
attcgtatta aatatgtctt acacaatcgc aactccatcg caatttgtgt ttttgtcatc    5760
agcatgggcc gaccctatag aattaataaa tttatgtact aattcactag gtaatcagtt    5820
ccaaacacaa caagctagaa caaccgttca acggcaattt agcgaagtgt ggaaacctgt    5880
ccctcaagtc actgttaggt ttcctgacag tggttttaag gtgtataggt acaatgcggt    5940
actagatcct ctagttactg ctttgttagg agctttcgat actagaaata ggattataga    6000
agtcgaaaat caggcgaacc cgacaaccgc cgaaacgtta dacgctactc gtagagtaga    6060
tgacgcaacg gtggctataa ggagcgctat aaataattta gtagtagaat ggtcaaagg     6120 aacaggtttg tacaatcaga gcacatttga aagtgcatcc ggtttacaat ggtcctctgc    6180
acctgcatct tgagataatc gagatgctta aataacagat tgtgtctgca aacacacgtg    6240
gtacgtacga taacgtatag tgttttccc tccacttaaa tcgaagggta gtgtcttgga     6300
```
gcgcgcggga caaatgtgta tggttcatac acatccgtag gcacgtaata aagcgaggga    6360
ttcgaattcc cccggaaccc ccggagggc cca                                 6393

<210> SEQ ID NO 26
<211> LENGTH: 6392
<212> TYPE: DNA
<213> ORGANISM: Tomato Brown Rugose Fruit virus

<400> SEQUENCE: 26
gtgtattttt tacaacatat accaacaaca acaaacaaca aacaacaaca ttacaattac      60
tatttacaac tacaatggca tacacacaga cagctaccac atccgctttg ctcgacactg     120
tccgaggtaa caataccttg gtcaacgatc ttgcgaagcg gcgtctttat gacacagcgg     180
tcgacgagtt caacgctcgt gatcgcaggc caaagtaaaa tttttccaaa gtaataagtg     240
aggaacagac gcttattgct actagggcat atccagaatt ccagataacc ttctataata     300
cgcagaacgc cgtgcattcg cttgccggtg gactacgatc cttagaactg gaatatctaa     360
tgatgcagat cccgtacgga tcactcacat atgatatagg tgggaatttt gcatctcatc     420
tgttcaaagg acgggcatat gttcactgct gtatgcccaa tcttgatgtc cgcgacataa     480
tgcggcacga aggccagaaa gacagtatag aattatacct ttccaggctt gagcggggca     540
acaaagttgt cccaaatttc caaaggaag cttttgacag atacgctgaa acgccagacg      600
aagttgtctg tcacagtacc ttccaaacgt gtacgcacca gcaggtggaa acacaggca      660 gggtgtatgc tattgcattg cacagtatat acgatatacc tgctgatgaa ttcggagcgg     720
cacttttaag gaaaaatgtc catgtttgtt acgccgcctt ccacttttcc gagaatttac     780
ttctcgaaga ttcacacgtc aaccttgacg aaatcaacgc gtgttttcg cgtgatggag      840 acaagctgac ttttctttc gcatctgaga gcactttaaa ttattgtcat agttattcta     900 atatttaaa atacgtgtgc aaaacttact cccggcatc taatagagag gtctacatga      960 aggagtttt ggtcaccagg gttaacacct ggttttgtaa gttttctagg atagatactt     1020
ttttattata caagggggta gcccacaaag gtgtaaatag tgagcaattt tacagcgcaa     1080
tggaagatgc atggcactac aaaaagactc ttgcaatgtg taacagcgag aggattcttc     1140
ttgaagattc ctcatcggtc aattactggt tcccaaaaat gagagatatg gtcatagttc     1200
ctctattcga catatctctc gacaccagta aaaggacccg caaagaagtc ttagtgtcaa     1260
aggattttgt attcacagtt ttaaatcaca ttcgcactta tcaagccaag gcacttacat     1320
actccaatgt tttatccttt gtcgaatcaa ttcgttcaag gtaattatc aacgagtga      1380 ctgccaggtc tgagtgggat gttgacaaat ctcttttgca atccttgtcc atgacatttt     1440
tcttgcatac taagcttgcc gttttaaaag acgaattgtt aatcagcaag tttagtttgg     1500
ggccaaaatc agtaagccag catgtatggg atgagatttc cctggctttt ggaaacgcat     1560
ttccatcgat caaggagaga ctgctaaatc ggaaactaat taagtgtcg ggagacgcat      1620 tagaaatcag ggtgcctgat ttatatgtga cttttcacga tagattagtg actgagtaca     1680
aaacatcggt ggatatgcca gtgcttgata tcagaaagag aatggaggag actgaggtta     1740
tgtacaatgc attgtctgag ctatctgtgc tcaaggagtc ggacaagttc gacgttgatg     1800
ttttttcccg gatgtgccag actttggagg tagacccaat gactgcagca aaggttattg     1860
tggcagtgat gagcaacgag agcggactga ctcttacatt cgaacagcca actgaagcaa     1920
atgtcgcatt ggcactttaaa gattcagaaa aagcctctga gggtgcacta gtggttactt     1980
ctagagatgt tgaagaacca tccatgaagg gttcaatggc aagaggagag ttacaattgg     2040

```
ccggtctgtc tggagaccaa ccagagtctt cctatactcg gaacgaggaa atagagtcat  2100
tagagcaatt ccacatggca acggctagtt cgttaattcg gaaacagatg agttcgattg  2160
tgtacacggg ccccattaaa gttcagcaaa tgaaaaactt tattgatagc ctggtagcat  2220
cactctctgc tgcggtgtcg aacctagtca agatcctaaa ggatacagct gctatagatc  2280
tcgaaacccg tcagaagttt ggagtcttag atgttgcgac caaaagatgg ttaattaaac  2340
ctttagccaa gaatcacgca tggggcgtta ttgaaacaca tgctaggaag taccacgttg  2400
cacttttgga gtatgatgag catggagtgg taacttgcga cagttggaga agggtggccg  2460
tgagttctga gtcaatggtt tattctgata tggcaaagct cagaacactg aggagattat  2520
taagagatgg agagcctcat gtcagcagtg ctaaagtcgt cctagttgac ggtgtcccgg  2580
gttgtggaaa gacaaaagag attctctcga agtaaatttt tgaggaagat ctaatcttag  2640
taccgggtaa gcaggctgct gaaatgataa agaggcgtgc taatgcgtca ggaataattc  2700
aagccacaag agataatgtt cgtactgttg attcatttat aatgaattac ggtaaaggaa  2760
cacgctgtca gttcaaaagg ttatttatcg acgaaggtct gatgttgcac actggttgtg  2820
tgaattttct tgtttctatg tctctgtgcg aaattgcata tgtttatgga gacacacaac  2880
aaattccata catcaacaga gtatccggtt ttccgtaccc tgcacatttt gcaaaaatag  2940
aggttgatga ggtggaaact cgcagaacta cgctgcgttg tccagccgac attacccact  3000
atcttaacag aaggtacgaa ggacatgtca tgtgtacatc gtcggttaaa aagtcagttt  3060
ctcaggaaat ggtgagcggg gccgcaatga tcaatcctgt atctaagcca ttgaatggga  3120
aagttttgac tttcactcag tctgataaag aggcgctgct ttctcgagga tatacggacg  3180
tccatacagt acatgaggta caaggtgaga catatgcaga tgtgtcgttg gtcagattga  3240
ctccgacacc tgtatctatc atcgcaggag atagtccgca cgttctcgta gctttgtcaa  3300
ggcatacccc aacattgaag tattacaccg tagtgatgga tcctcttgta agtataatta  3360
gggatttaga aaaacttagt tcttacttgt tagatatgta taaagtagat gcagggaccc  3420
aatagcaatt acaggtagac tccgtgttta aaggttctaa tcttttttgtt gcagcaccaa  3480 agactggaga tatctcagat atgcaatttt actatgataa gtgtctccca ggtaatagca  3540
ccatgttaaa taactatgat gctgttacca tgaggttgac tgacatttct cttaatgtca  3600
aagattgcat attggatttc tctaagtctg tggctgcacc gaaggatccg atcaaaccac  3660
tgattccaat ggtacgaacg gcggcagaaa tgccacgcca gactggacta ttggaaaatt  3720
tggtggcgat gatcaaaaga aactttaatt caccggagtt atcaggaata atcgacattg  3780
agaatactgc atctttagta gtagataaat ttttttgatag ttacttgctt aaagaaaaaa  3840
gaaaaccaaa taaaaatgtt tctttattt gtagagagtc tctcaataga tggttagaga  3900
agcaggagca agtgaccatt ggtcagcttg cagattttga ttttgtggat cttcctgccg  3960
ttgatcagta caggcatatg attaaagcgc aacctaagca gaagctggat acatcaattc  4020
aaagcgaata tccggccttg cagacgattg tgtatcattc gaaaaagatc aacgcaatct  4080
tcggtccttt gttcagtgag ctcacaaggc aaatgtctcga agcatagac tcaagtaagt  4140 ttttgttctt tacaaggaag acgccagctc aaattgagga tttcttcgga gatctcgata  4200
gccatgtccc tatggatatc ttggagttgg atatttcgaa gtatgacaaa tctcagaacg  4260
agttccactg tgcagtagag tatgaaatat ggagaagact tggattagaa gattttctgg  4320
gagaagtttg gaaacaaggc cacaggaaaa ctactcttaa agattacaca gctggtatta  4380
```

```
aaacgtgttt atggtaccag agaaagagtg gggacgttac aacattcatc ggtaatacgg    4440
tgattattgc tgcttgttta gcttccatgt tgcccatgga gaaaataatc aaaggtgcat    4500
tttgcggaga tgacagttta ctatacttcc caaaaggttg tgagtttcct gacatacagc    4560
atacagccaa ccttatgtgg aatttcgagg ctaagctatt cagaaagcag tatggttatt    4620
tctgtggaag gtacgtgata catcatgaca gagggtgtat tgtttattat gacccttga    4680 agttgatttc taaacttggt gctaaacaca tcaaggattg ggatcactta gaagagttca    4740
gaagatccct ttgtgatgtt gcaaattcgt tgaacaactg tgcgtattac acgcagttgg    4800
acgacgctgt gagtgaggtc cataaaaccg caccccggg ttcgtttgta tataaaagtt    4860
tagttaaata tctgtccgat aaggttcttt ttagaagttt gtttatagat ggctcttgtt    4920
aagggtaaag tcaatattaa tgagttcata gacttgtcaa aatcagaaaa atttcttccg    4980
tctatgttca cacctgttaa gagtgtcatg atctccaagg ttgataagat attggttcat    5040
gaagatgaat ctttgtccga agtcaattta ctcaaaggtg taaaactcat tgatggtggc    5100
tatgtacatc ttgctggtct tgtggtgaca ggtgaatgga atttgccaga taattgtcgt    5160
ggtggtgtca gtgtctgttt ggtcgataag agaatggaga gagcggacga ggcaactctt    5220
gcttcatact ataccgcagc ggctaagaaa aggtttcagt tcaaagtcgt tccaaattac    5280
aacatcacta ccaaggacgc agaaaaggca gtttggcaag tactagttaa tattagaaat    5340
gttaaaattg ctgcgggtta ctgtccgctg tcattagaat ttgtgtcagt gtgtattgtt    5400
tataaaaata ttataaaact cggtttgaga gagaaaatta cgagcgtcac ggatggaggg    5460
cccatggaac tatcagaaga agttgttgat gagttcatgg aagaagtccc gatgtctgta    5520
aggcttgcaa aatttcgttc gaagaccgga aaaaagttta gtagtaaaag tgagaataat    5580
agtggtaata ataggccgaa accaaacaaa aaccaaagga aggaaaaggg tttaaaagtt    5640
agggttgaga aggataattt aattgataat gaattggaga cttacgtcgc cgattcagat    5700
tcgtattaaa tatgtcttac acaatcgcaa ctccatcgca atttgtgttt ttgtcatcag    5760
catgggccga ccctatagaa ttaataaatt tatgtactaa ttcactaggt aatcagttcc    5820
aaacacaaca agctagaaca accgttcaac ggcaatttag cgaagtgtgg aaacctgtcc    5880
ctcaagtcac tgttaggttt cctgacagtg gtttttaaggt gtataggtac aatgcggtac    5940
tagatcctct agttactgct ttgttaggag cttcgatac tagaaatagg attatagaag    6000
tcgaaaatca ggcgaacccg acaaccgccg aaacgttaga cgctactcgt agagtagatg    6060
acgcaacggt ggctataagg agcgctataa ataatttagt agtagaattg gtcaaaggaa    6120
caggtttgta caatcagagc acatttgaaa gtgcatccgg tttacaatgg tcctctgcac    6180
ctgcatcttg agataatcga gatgcttaaa taacagattg tgtctgcaaa cacacgtggt    6240
acgtacgata acgtatagtg tttttccctc cacttaaatc gaagggtagt gtcttggagc    6300
gcgcgggaca aatgtgtatg gttcatacac atccgtaggc acgtaataaa gcgagggatt    6360
cgaattcccc cggaaccccc ggtaggggcc ca                                  6392
```